United States Patent
Won et al.

(10) Patent No.: US 10,712,199 B2
(45) Date of Patent: Jul. 14, 2020

(54) SPECTROMETRIC SENSING APPARATUS FOR DETECTING ONE OR MORE TYPES OF BIOMETRIC INFORMATION IN ELECTRONIC DEVICE AND METHOD THEREOF COMPRISING A PROCESSOR CONTROLLING A LIGHT EMITTING UNIT TO SELECTIVELY OUTPUT LIGHT OF A WAVELENGTH BAND CORRESPONDING TO AT LEAST ONE MODE

(71) Applicant: Samsung Electronics Co., Ltd., Gyeonggi-do (KR)

(72) Inventors: Jin-Hee Won, Gyeonggi-do (KR); Jaesung Lee, Gyeonggi-do (KR); Jongmin Choi, Seoul (KR); Taeho Kim, Chungcheongbuk-do (KR); Jeong-Min Park, Gyeonggi-do (KR)

(73) Assignee: Samsung Electronics Co., Ltd., Yeongtong-du, Suwon-si, Gyeonggi-do (KR)

( * ) Notice: Subject to any disclaimer, the term of this patent is extended or adjusted under 35 U.S.C. 154(b) by 69 days.

(21) Appl. No.: 15/701,794

(22) Filed: Sep. 12, 2017

(65) Prior Publication Data

US 2018/0094974 A1 Apr. 5, 2018

(30) Foreign Application Priority Data

Sep. 30, 2016 (KR) .................. 10-2016-0126382

(51) Int. Cl.
*G01J 3/02* (2006.01)
*G01J 3/10* (2006.01)
(Continued)

(52) U.S. Cl.
CPC ............ *G01J 3/027* (2013.01); *A61B 5/0075* (2013.01); *A61B 5/443* (2013.01); *A61B 5/6898* (2013.01);
(Continued)

(58) Field of Classification Search
CPC ... A61B 5/0075; A61B 5/6898; A61B 5/0095; G01B 11/14; G01N 21/31; G01V 8/12;
(Continued)

(56) References Cited

U.S. PATENT DOCUMENTS

| 8,731,618 B2 * | 5/2014 | Jarvis | ..................... F16F 1/027 267/164 |
|---|---|---|---|
| 2010/0208261 A1 | 8/2010 | Sens et al. | |

(Continued)

FOREIGN PATENT DOCUMENTS

| CN | 101997054 A | 3/2011 |
|---|---|---|
| EP | 3 301 894 A1 | 4/2018 |

(Continued)

OTHER PUBLICATIONS

European Search Report dated Jan. 31, 2018.
Chinese Search Report dated Jun. 28, 2019.
Chinese Search Report dated Mar. 3, 2020.

*Primary Examiner* — Que Tan Le
(74) *Attorney, Agent, or Firm* — Cha & Reiter, LLC.

(57) ABSTRACT

Disclosed is an electronic device includes a housing, a display within the housing, and exposed through a surface of the housing, a light emitting unit and a light receiving unit within the housing, and a processor electrically coupled with the display, the light emitting unit and the light receiving unit. The light emitting unit includes at least one light source for outputting light of at least one wavelength band. The light receiving unit includes at least one region for receiving the light of the at least one wavelength band. The processor is configured to control a function of the light emitting unit
(Continued)

and/or the light receiving unit based on at least one mode. Other embodiments are disclosed.

10 Claims, 47 Drawing Sheets

(51) Int. Cl.
| | |
|---|---|
| *G01N 21/31* | (2006.01) |
| *G01J 3/28* | (2006.01) |
| *H04M 1/725* | (2006.01) |
| *A61B 5/00* | (2006.01) |
| *G01B 11/14* | (2006.01) |
| *A61B 5/024* | (2006.01) |
| *A61B 5/021* | (2006.01) |
| *A61B 5/01* | (2006.01) |
| *A61B 5/145* | (2006.01) |

(52) U.S. Cl.
CPC ............ *A61B 5/7445* (2013.01); *G01B 11/14* (2013.01); *G01J 3/0272* (2013.01); *G01J 3/10* (2013.01); *G01J 3/2803* (2013.01); *G01N 21/31* (2013.01); *H04M 1/72522* (2013.01); *A61B 5/0082* (2013.01); *A61B 5/01* (2013.01); *A61B 5/021* (2013.01); *A61B 5/024* (2013.01); *A61B 5/14532* (2013.01); *A61B 2576/00* (2013.01); *G01N 2201/0221* (2013.01); *H04M 1/72519* (2013.01); *H04M 2250/12* (2013.01)

(58) Field of Classification Search
CPC ...... G01J 3/0272; G01J 3/2803; G01J 1/4204; G01J 3/027; H04M 1/72519; H04M 1/72569
USPC ...................................... 250/221, 205, 214 R
See application file for complete search history.

(56) References Cited

U.S. PATENT DOCUMENTS

| | | | |
|---|---|---|---|
| 2011/0042556 A1 | 2/2011 | Natsuaki | |
| 2015/0308896 A1 | 10/2015 | Darty | |
| 2017/0188852 A1* | 7/2017 | Sugita | A61B 5/026 |
| 2018/0136363 A1* | 5/2018 | Yoon | G01J 3/46 |
| 2018/0364869 A1* | 12/2018 | Lee | G06F 3/0421 |

FOREIGN PATENT DOCUMENTS

| | | |
|---|---|---|
| KR | 10-2010-0077018 A | 7/2010 |
| WO | 2013/184226 A1 | 12/2013 |
| WO | 2016/125164 A2 | 8/2016 |

\* cited by examiner

SPECTROMETRIC SENSING APPARATUS FOR DETECTING ONE OR MORE TYPES OF BIOMETRIC INFORMATION IN ELECTRONIC DEVICE AND METHOD THEREOF COMPRISING A PROCESSOR CONTROLLING A LIGHT EMITTING UNIT TO SELECTIVELY OUTPUT LIGHT OF A WAVELENGTH BAND CORRESPONDING TO AT LEAST ONE MODE

CLAIM OF PRIORITY

This application claims priority under 35 U.S.C. § 119(a) to a Korean Patent Application filed on Sep. 30, 2016 in the Korean Intellectual Property Office and assigned Serial number 10-2016-0126382, the entire disclosure of which is hereby incorporated by reference.

TECHNICAL FIELD

The present disclosure relates to a spectrometric sensing apparatus in an electronic device and a method thereof.

BACKGROUND

A spectrometric sensor may be defined as a sensor that can be configured to disperse a spectrum of light radiated from a light source, and quantitatively measure radiation intensities, etc. at many wavelength positions in the spectrum. Currently, spectrometric sensors are used in various fields such as research fields, medicine fields, etc.

The above information is presented as background information only to assist with an understanding of the present disclosure. No determination has been made, and no assertion is made, as to whether any of the above might be applicable as prior art with regard to the present disclosure.

SUMMARY

The spectrometric sensor is difficult to be designed to be compact due to its internal structure. Being relatively large, mounting the spectrometric sensor in a portable electronic device such as a smartphone may be difficult. To add the spectrometric sensor to the portable electronic device, a relatively large amount of free space within the housing of the portable electronic device is needed. However, since various electronic components are mounted in the limited spaces within the portable electronic device, finding the space necessary for the spectrometric sensor is difficult. Also, in case of adding the spectrometric sensor, the portable electronic device has to additionally have a through-hole or transmission region so that light can be transmitted through the housing of the portable electronic device. This can disrupt the external aesthetics of the portable electronic device. Aspects of the present disclosure are to address at least the above mentioned problems and/or disadvantages and to provide at least the advantages described below. Accordingly, an aspect of the present disclosure is to provide a spectrometric sensing apparatus in an electronic device and a method thereof, where the spectrometric sensing apparatus is miniaturized so that the overall size of the electronic device does not substantially increase. Another aspect of the present disclosure is to provide a spectrometric sensing apparatus in an electronic device and a method thereof, in which spectrometric sensing is made available using at least a part of an optical sensor of the electronic device.

In accordance with an aspect of the present disclosure, an electronic device is provided. The electronic device includes a housing, a display within the housing and exposed through a surface of the housing, a light emitting unit and a light receiving unit within the housing, and a processor electrically coupled with the display, the light emitting unit and the light receiving unit. The light emitting unit may include at least one light source for outputting light of at least one wavelength band. The light receiving unit may include at least one region for receiving the light of the at least one wavelength band. The processor may control a function of the light emitting unit and/or the light receiving unit based on at least one mode.

In accordance with another aspect of the present disclosure, a method for operating an electronic device is provided. The method includes selecting a detection mode based on the execution of an application and/or a user input, determining an output wavelength band of a light emitting unit based on the selected detection mode, outputting light of the determined output wavelength band via the light emitting unit, detecting, via a light receiving unit, at least a part of the outputted light that is scattered or reflected from an object, and acquiring information related with the selected detection mode based on the light detected by the light receiving unit.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1:
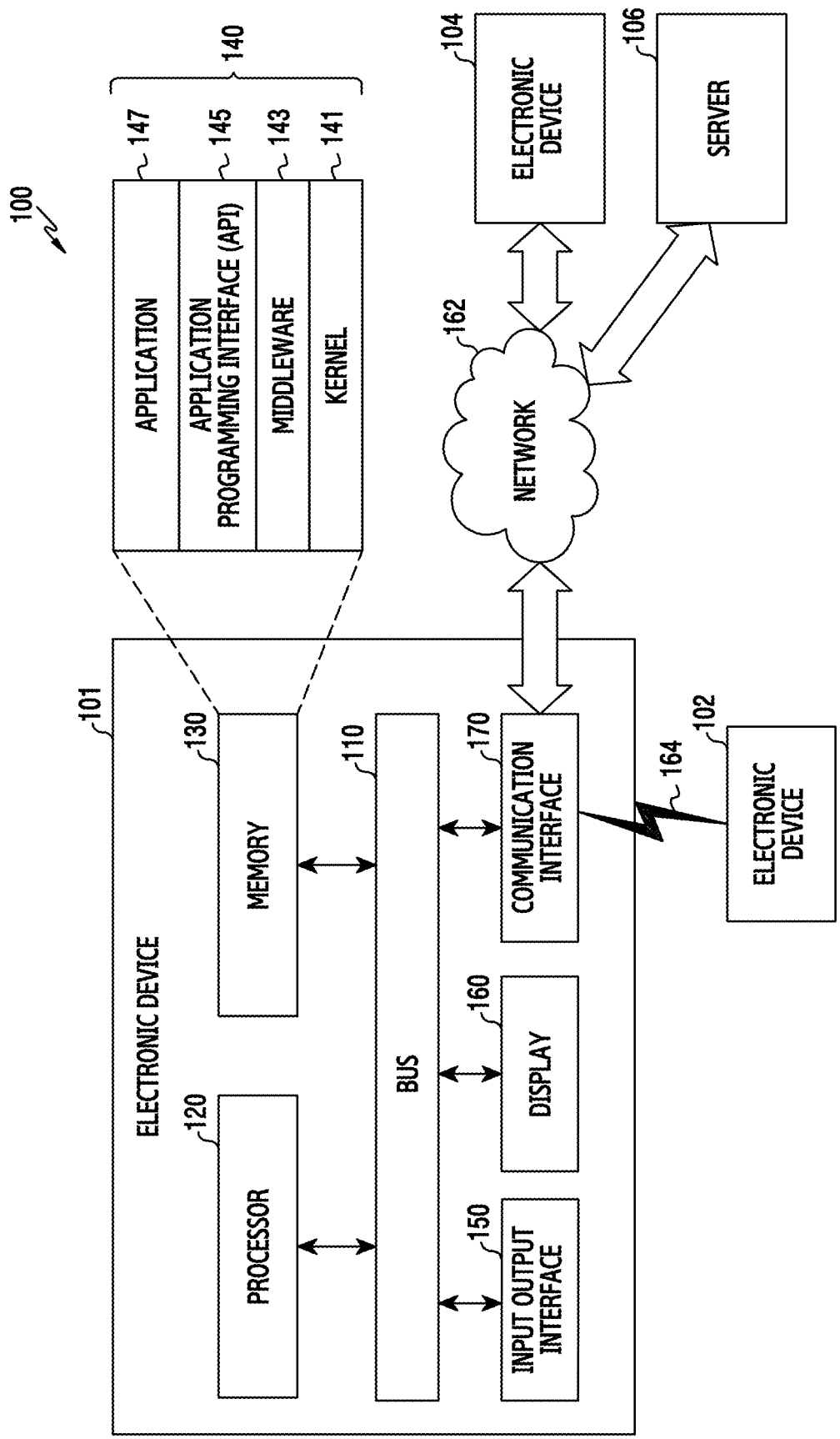
FIG. 1 is a block diagram of a network environment according to an embodiment of the present disclosure.

Various embodiments of the present document are mentioned below with reference to the accompanying drawings. An embodiment and the terms used in this do not intend to limit the technology mentioned in the present document to a specific embodiment form, and should be construed as including various changes of the corresponding embodiment, equivalents thereof, and/or alternatives thereof. In the drawings, like reference symbols may denote like constituent elements. The expression of a singular form may include the expression of a plural form unless otherwise dictating clearly in context. In the present document, the expressions "A or B", "at least one of A and/or B", etc. may include all available combinations of words enumerated together. The expressions "1st", "2nd", "first", "second", etc. may modify corresponding constituent elements irrespective of order and/or importance, and are just used to distinguish one constituent element from another constituent element and do not limit the corresponding constituent elements. When it is mentioned that any (e.g., 1st) constituent element is "(operatively or communicatively) coupled with/to" or is "connected to" another (e.g., 2nd) constituent element, the any constituent element may be directly coupled to the another constituent element, or be coupled through a further constituent element (e.g., a third constituent element).

The expression "configured (or set) to" used in the present document may be used interchangeably with, for example, "suitable for", "having the capacity to", "designed to", "adapted to", "made to", or "capable of" in a hardware or software manner in accordance to circumstances. In any situation, the expression "device configured to" may represent that the device is "capable of" together with other devices or components. For example, the phrase "processor configured (or set) to perform A, B and C" may represent an exclusive processor (e.g., embedded processor) for performing a corresponding operation, or a generic-purpose processor (e.g., a central processing unit (CPU) or an application processor (AP)) capable of performing corresponding operations by executing one or more software programs stored in a memory device.

An electronic device according to various embodiments of the present document may, for example, include at least one of a smartphone, a tablet personal computer (PC), a mobile phone, a video phone, an electronic book reader, a desktop PC, a laptop PC, a netbook computer, a workstation, a server, a portable digital assistant (PDA), a portable multimedia player (PMP), an MPEG-1 audio layer-3 (MP3) player, a medical device, a camera or a wearable device. The wearable device may include at least one of an accessory type (e.g., a watch, a ring, a wristlet, an anklet, a necklace, glasses, a contact lens or a head-mounted-device (HMD)), a fabric or clothing integrated type (e.g., electronic clothes), a human-body mount type (e.g., a skin pad or tattoo) or a bio implantation type (e.g., an implantable circuit). According to certain embodiment, the electronic device may, for example, include at least one of a television (TV), a digital versatile disc (DVD) player, an audio system, a refrigerator, an air conditioner, a cleaner, an oven, a microwave, a washing machine, an air cleaner, a set-top box, a home automation control panel, a security control panel, a media box (for example, Samsung HomeSync™, Apple TV™ or Google TV™), a game console (e.g., Xbox™ or PlayStation™), an electronic dictionary, an electronic locking system, a camcorder or an electronic frame.

In another embodiment, the electronic device may include at least one of various medical devices (e.g., various portable medical measurement devices (e.g., a blood glucose sensor, a heat rate sensor, a blood pressure monitor, a body temperature meter, etc.), magnetic resonance angiography (MRA), magnetic resonance imaging (MRI), computed tomography (CT), a imaging equipment, an ultrasonic instrument, etc.)), a navigation device, a global navigation satellite system (GNSS), an event data recorder (EDR), a flight data recorder (FDR), a car infotainment device, an electronic equipment for ship (e.g., a vessel navigation device, a gyro compass, etc.), avionics, a security device, a car head unit, an industrial or domestic robot, a drone, an automatic teller's machine (ATM) of a financial institution, point of sales (POS) of shops or an internet of things (IoT) device (e.g., an electric bulb, various sensors, a sprinkler device, a fire alarm, a thermostat, a streetlight, a toaster, an exerciser, a hot water tank, a heater, a boiler, etc.). According to certain embodiment, the electronic device may include at least one of a part of furniture, a building/structure or a car, an electronic board, an electronic signature receiving device, a projector or various metering devices (e.g., tap water, electricity, gas, radio wave metering devices or the like). In various embodiments, the electronic device may be flexible, or be a combination of two or more of the aforementioned various devices. The electronic device according to an embodiment of the present document is not limited to the aforementioned devices. In the present document, the term 'user' may denote a person who uses the electronic device or a device (e.g., an artificial-intelligent electronic device) which uses the electronic device.

FIG. 1 is a block diagram of a network environment according to an embodiment of the present disclosure.

Referring to FIG. 1, an electronic device 101 within a network environment 100 in various embodiments is described. The electronic device 101 may include a bus 110, a processor 120, a memory 130, an input output interface 150, a display 160, and a communication interface 170. In some embodiment, the electronic device 101 may omit at least one of the constituent elements or additionally have another constituent element. The bus 110 may, for example, include a circuit coupling the constituent elements 110, 120, 150, 160 and 170 with one another and forwarding communication (e.g., a control message or data) between the constituent elements. The processor 120 may include one or more of a central processing unit (CPU), an application processor (AP) or a communication processor (CP). The processor 120 may, for example, execute operation or data processing for control and/or communication of at least one another constituent element of the electronic device 101.

The memory 130 may include a volatile and/or non-volatile memory. The memory 130 may, for example, store a command or data related to at least one another constituent element of the electronic device 101. According to an embodiment, the memory 130 may store a software and/or program 140. The program 140 may, for example, include a kernel 141, a middleware 143, an application programming interface (API) 145, an application program (or "application") 147, and the like. At least some of the kernel 141, the middleware 143 or the API 145 may be called an operating system (OS). The kernel 141 may, for example, control or manage system resources (e.g., bus 110, processor 120, memory 130, and the like) that are used for executing operations or functions implemented in other programs (e.g., middleware 143, API 145 or application program 147). Also, the kernel 141 may provide an interface through which the middleware 143, the API 145 or the application program 147 may control or manage the system resources of the electronic device 101 by accessing the individual constituent element of the electronic device 101.

According to an embodiment, the application program 147 may include a thing analysis application for analyzing a thing using a spectrometric sensing apparatus (not shown). For example, the thing analysis application may use the spectrometric sensing apparatus, to acquire information about a skin moisture, a skin melanin, a skin erythema or the like of the user skin.

According to an embodiment, the memory 130 may include spectrometric sensing apparatus setting information for the control of at least one function of the light receiving unit and/or the light emitting unit of the spectrometric sensing apparatus, where the spectrometric sensing apparatus detects light in a spectrum. In the selected (or activated) detection mode, the processor 120 may control the light receiving unit and/or the light emitting unit based on the spectrometric sensing apparatus setting information of the memory 130.

The middleware 143 may, for example, perform a relay role of enabling the API 145 or the application program 147 to communicate and exchange data with the kernel 141. Also, the middleware 143 may process one or more work requests that are received from the application program 147, in accordance with priority. For example, the middleware 143 may grant priority capable of using the system resources (e.g., the bus 110, the processor 120, the memory 130 or the like) of the electronic device 101 to at least one of the application programs 147, and process one or more work requests. The API 145 is, for example, an interface enabling the application program 147 to control a function provided by the kernel 141 or the middleware 143 and may, for example, include at least one interface or function (e.g., an instruction) for file control, window control, image processing, character control or the like. The input output interface 150 may forward a command or data inputted from a user or another external device, to another constituent element(s) of the electronic device 101, or output a command or data received from the another constituent element(s) of the electronic device 101, to the user or another external device.

The display 160 may, for example, include a liquid crystal display (LCD), a light emitting diode (LED) display, an organic light emitting diode (OLED) display, a microelectromechanical systems (MEMS) display or an electronic paper display. The display 160 may, for example, display various contents (e.g., a text, an image, a video, an icon, a symbol and/or the like) to a user. The display 160 may include a touch screen. And, for example, the display 160 may receive a touch, gesture, proximity or hovering input that uses an electronic pen or a part of the user's body. The communication interface 170 may, for example, establish communication between the electronic device 101 and an external device (e.g., the first external electronic device 102, the second external electronic device 104 or the server 106). For example, the communication interface 170 may be coupled to a network 162 through wireless communication or wired communication, to communicate with the external device (e.g., the second external electronic device 104 or the server 106).

The wireless communication may, for example, include a cellular communication that uses at least one of long term evolution (LTE), LTE-advanced (LTE-A), code division multiple access (CDMA), wideband CDMA (WCDMA), universal mobile telecommunications system (UMTS), wireless broadband (WiBro), global system for mobile communications (GSM) and the like. According to an embodiment, the wireless communication may, for example, a short-range communication 164. The short-range communication 164 may for example, include at least one of wireless fidelity (WiFi), Bluetooth (BT), Bluetooth low energy (BLE), Zigbee, near field communication (NFC), magnetic secure transmission (MST), radio frequency (RF) or body area network (BAN). According to an embodiment, the wireless communication may include GNSS. The GNSS may, for example, be a global positioning system (GPS), a global navigation satellite system (Glonass), Beidou navigation satellite system (hereinafter, "Beidou")) or Galileo, the European global satellite-based navigation system. Hereinafter, the "GPS" may be used interchangeably with the "GNSS". The wired communication may, for example, include at least one of a universal serial bus (USB), a high definition multimedia interface (HDMI), a recommended standard-232 (RS-232), power line communication (PLC), a plain old telephone service (POTS), and the like. The network 162 may include, for example, at least one of a telecommunications network, a computer network (e.g., local area network (LAN) or wide area network (WAN)), the Internet or a telephone network.

Each of the first and second external electronic devices 102 and 104 may be a device of the same or different type from that of the electronic device 101. According to various embodiments, all or some of operations executed in the electronic device 101 may be executed in another one electronic device or a plurality of electronic devices (e.g., the external electronic devices 102 and 104 or the server 106). According to an embodiment, in case where the electronic device 101 performs some function or service automatically or in response to a request, the electronic device 101 may, instead of or additionally to executing the function or service in itself, send a request for execution of at least a partial function associated with this to another device (e.g., external electronic device 102, 104 or server 106). The another electronic device (e.g., external electronic device 102, 104 or server 106) may execute the requested function or additional function, and forward the execution result to the electronic device 101. The electronic device 101 may process the received result as it is or additionally, to provide the requested function or service. For this, a cloud computing, distributed computing or client-server computing technology may be used, for example.

Figure 2:
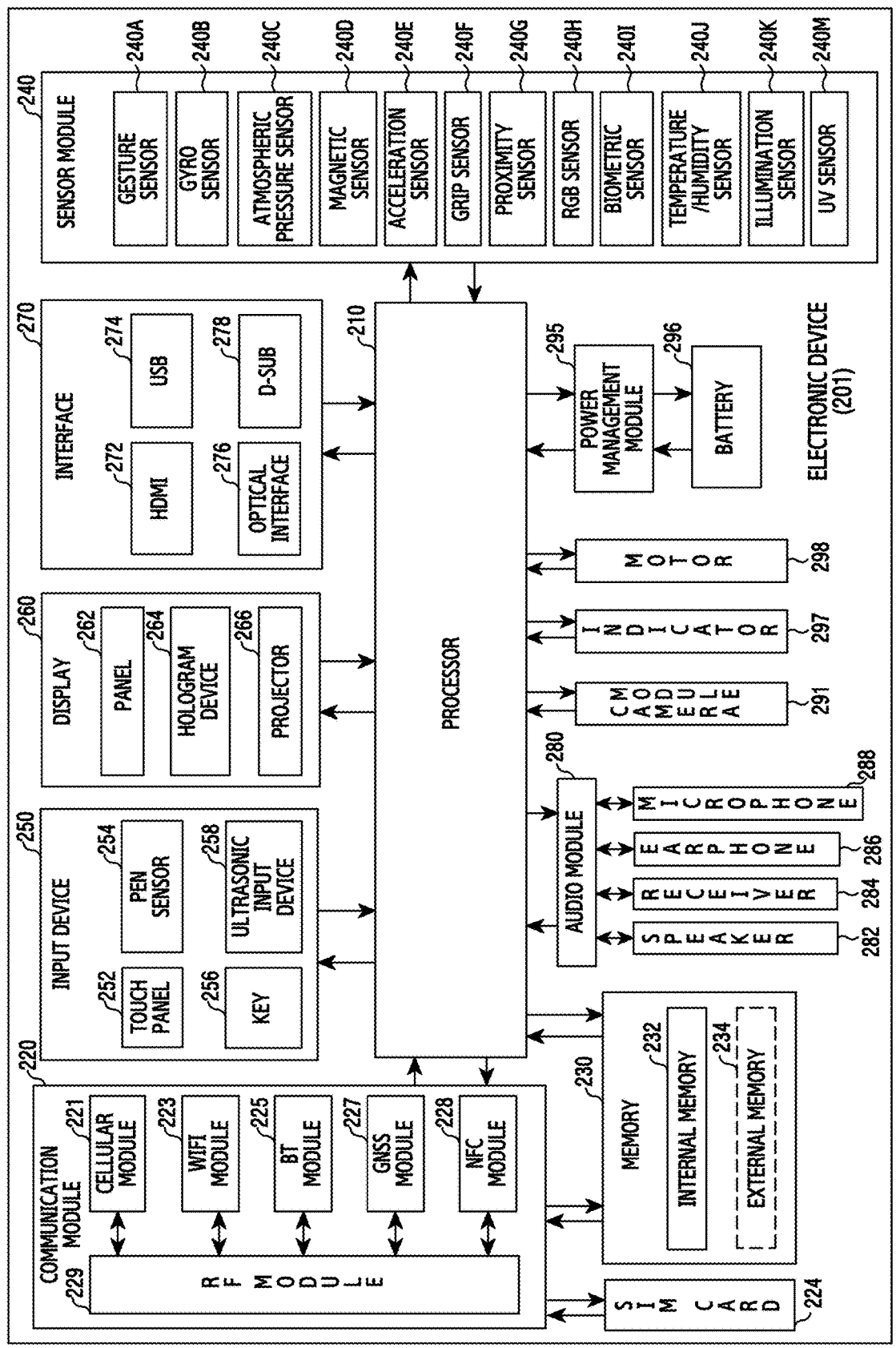
FIG. 2 is a block diagram of an electronic device according to an embodiment of the present disclosure.

FIG. 2 is a block diagram of an electronic device according to an embodiment of the present disclosure.

Referring to FIG. 2, an electronic device 201 may, for example, include the entire or part of the electronic device 101 illustrated in FIG. 1. The electronic device 201 may include one or more processors (e.g., application processor (APs)) 210, a communication module 220, a subscriber identification module 224, a memory 230, a sensor module 240, an input device 250, a display 260, an interface 270, an audio module 280, a camera module 291, a power management module 295, a battery 296, an indicator 297 and a motor 298.

The processor 210 may, for example, drive an operating system or an application program to control a plurality of hardware or software constituent elements coupled to the processor 210, and may perform various data processing and operations. The processor 210 may be, for example, implemented as a system on chip (SoC). According to an embodiment, the processor 210 may further include a graphic processing unit (GPU) and/or an image signal processor (ISP). The processor 210 may include at least some (e.g., cellular module 221) of the constituent elements illustrated in FIG. 2 as well. The processor 210 may load a command or data received from at least one of the other constituent elements (e.g., non-volatile memory), to a volatile memory, to process the loaded command or data, and store the result data in the non-volatile memory. The processor 210 may include a microprocessor or any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), a Graphical Processing Unit (GPU), a video card controller, etc. In addition, it would be recognized that when a general purpose computer accesses code for implementing the processing shown herein, the execution of the code transforms the general purpose computer into a special purpose computer for executing the processing shown herein. Any of the functions and steps provided in the Figures may be implemented in hardware, software or a combination of both and may be performed in whole or in part within the programmed instructions of a computer. No claim element herein is to be construed under the provisions of 35 U.S.C. 112, sixth paragraph, unless the element is expressly recited using the phrase "means for." In addition, an artisan understands and appreciates that a "processor" or "microprocessor" may be hardware in the claimed disclosure. Under the broadest reasonable interpretation, the appended claims are statutory subject matter in compliance with 35 U.S.C. § 101.

According to an embodiment, the processor 210 may control at least a partial function of the light emitting unit and/or the light receiving unit of a spectrometric sensing apparatus (not shown) that operates in one or more modes. For example, in one mode, the processor 210 may control the light emitting unit to selectively output light of a wavelength band. For another example, the light emitting unit may include a plurality of light sources for outputting light of mutually different wavelength bands, and the processor 210 may selectively activate one or more of the plurality of light sources in another mode. According to various embodiments, in one mode, the processor 210 may selectively activate a region of the light receiving unit. According to various embodiments, the processor 210 may acquire information based on light that is acquired through the light receiving unit, and display the acquired information through the display 260. According to various embodiments, the processor 210 may acquire the information based on the light that is acquired through the light receiving unit, and transmit the acquired information to another electronic device (e.g., 102, 104 or 106 of FIG. 1) through the communication module 220.

The communication module 220 may, for example, have the same or similar construction with the communication interface 170. The communication module 220 may, for example, include a cellular module 221, a WiFi module 223, a Bluetooth module 225, a GNSS module 227, a near field communication (NFC) module 228, and a radio frequency (RF) module 229. The cellular module 221 may, for example, provide voice telephony, video telephony, a text service, an Internet service or the like through a telecommunication network. According to an embodiment, the cellular module 221 may perform the distinction and authentication of the electronic device 201 within the telecommunication network, by using the subscriber identification module (e.g., SIM card) 224. According to an embodiment, the cellular module 221 may perform at least some functions among functions that the processor 210 may provide. According to an embodiment, the cellular module 221 may include a communication processor (CP). According to some embodiment, at least some (e.g., two or more) of the cellular module 221, the WiFi module 223, the Bluetooth module 225, the GNSS module 227 or the NFC module 228 may be included within one integrated chip (IC) or IC package. The RF module 229 may, for example, transceive a communication signal (e.g., RF signal). The RF module 229 may, for example, include a transceiver, a power amplifier module (PAM), a frequency filter, a low noise amplifier (LNA), an antenna or the like. According to another embodiment, at least one of the cellular module 221, the WiFi module 223, the Bluetooth module 225, the GNSS module 227 or the NFC module 228 may transceive an RF signal through a separate RF module. The subscriber identification module 224 may, for example, include a card including a subscriber identification module and/or an embedded SIM. And, the subscriber identification module 224 may include unique identification information (e.g., integrated circuit card identifier (ICCID)) or subscriber information (e.g., international mobile subscriber identity (IMSI)).

The memory 230 (e.g., memory 130) may, for example, include an internal memory 232 or an external memory 234.

The internal memory 232 may, for example, include at least one of a volatile memory (e.g., a dynamic random access memory (DRAM), a static RAM (SRAM), a synchronous dynamic RAM (SDRAM) or the like) and a non-volatile memory (e.g., one time programmable read only memory (OTPROM), a programmable ROM (PROM), an erasable PROM (EPROM), an electrically EPROM (EEPROM), a mask ROM, a flash ROM, a flash memory, a hard drive or a solid state drive (SSD)). The external memory 234 may include a flash drive, for example, a compact flash (CF), a secure digital (SD), a micro-SD, a mini-SD, an extreme Digital (xD), a Multi Media Card (MMC), a memory stick or the like. The external memory 234 may be operatively or physically coupled with the electronic device 201 through various interfaces.

The sensor module 240 may, for example, measure a physical quantity or sense an activation state of the electronic device 201, to convert measured or sensed information into an electrical signal. The sensor module 240 may, for example, include at least one of a gesture sensor 240A, a gyro sensor 240B, a barometer 240C, a magnetic sensor 240D, an acceleration sensor 240E, a grip sensor 240F, a proximity sensor 240G a color sensor 240H (e.g., a red, green, blue (RGB) sensor), a biometric sensor 240I, a temperature/humidity sensor 240J, an illuminance sensor 240K or an ultra violet (UV) sensor 240M. Additionally or alternatively, the sensor module 240 may, for example, include an E-nose sensor, an electromyography (EMG) sensor, an electroencephalogram (EEG) sensor, an electrocardiogram (ECG) sensor, an infrared (IR) sensor, an iris scan sensor and/or a finger scan sensor. The sensor module 240 may further include a control circuit for controlling at least one or more sensors belonging therein. In some embodiment, the electronic device 201 may further include a processor configured to control the sensor module 240 as a part of the processor 210 or separately, thereby controlling the sensor module 240 while the processor 210 is in a sleep state.

According to an embodiment, a spectrometric sensing apparatus (not shown) may include at least a part of an optical sensor (e.g., the gesture sensor 240A, the proximity sensor 240G or the RGB sensor 240H) of the sensor module 240. For example, the spectrometric sensing apparatus may use a light emitting unit (not shown) of the sensor module 240 that has at least one light source for outputting light of at least one wavelength band. The spectrometric sensing apparatus may also include a light receiving unit (not shown) of the sensor module 240 that has at least one region for receiving light of at least one wavelength band.

The input device 250 may, for example, include a touch panel 252, a (digital) pen sensor 254, a key 256 or an ultrasonic input device 258. The touch panel 252 may, for example, use at least one scheme among a capacitive overlay scheme, a pressure sensitive scheme, an infrared beam scheme or an ultrasonic scheme. Also, the touch panel 252 may further include a control circuit as well. The touch panel 252 may further include a tactile layer, to provide a tactile response to a user. The (digital) pen sensor 254 may, for example, be a part of the touch panel 252, or include a separate sheet for recognition. The key 256 may, for example, include a physical button, an optical key or a keypad. The ultrasonic input device 258 may sense an ultrasonic wave generated in an input tool, through a microphone (e.g., microphone 288), to confirm data corresponding to the sensed ultrasonic wave.

The display 260 (e.g., the display 160) may include a panel 262, a hologram device 264, a projector 266, and/or a control circuit for controlling them. The panel 262 may, for example, be implemented to be flexible, transparent, or wearable. The panel 262 may be constructed as one or more modules together with the touch panel 252. The hologram device 264 may show a three-dimensional image to the air using an interference of light. The projector 266 may project light onto a screen, to display an image. The screen may, for example, be located inside or outside the electronic device 201. The interface 270 may, for example, include an HDMI 272, a USB 274, an optical interface 276 or a D-subminiature (D-sub) 278. The interface 270 may, for example, be included in the communication interface 170 illustrated in FIG. 1. Additionally or alternatively, the interface 270 may, for example, include a Mobile High-definition Link (MHL) interface, an SD card/Multi Media Card (MMC) interface or an Infrared Data Association (IrDA) standard interface.

The audio module 280 may, for example, convert a sound and an electrical signal interactively. At least some constituent elements of the audio module 280 may be, for example, included in the input output interface 150 illustrated in FIG. 1. The audio module 280 may for example, process sound information that is inputted or outputted through a speaker 282, a receiver 284, an earphone 286, the microphone 288 or the like. The camera module 291 is, for example, a device able to photograph a still image and a video. According to an embodiment, the camera module 291 may include one or more image sensors (e.g., front sensor or rear sensor), a lens, an image signal processor (ISP) or a flash (e.g., an LED, a xenon lamp or the like). The power management module 295 may, for example, manage the electric power of the electronic device 201. According to an embodiment, the power management module 295 may include a power management integrated circuit (PMIC), a charger IC or a battery or fuel gauge. The PMIC may, for example, employ a wired and/or wireless charging scheme. The wireless charging scheme may, for example, include a magnetic resonance scheme, a magnetic induction scheme, an electromagnetic wave scheme or the like. And, the wireless charging scheme may further include a supplementary circuit for wireless charging, for example, a coil loop, a resonance circuit, a rectifier or the like. The battery gauge may, for example, measure a level of the battery 296, a voltage being in charge, an electric current or a temperature. The battery 296 may, for example, include a rechargeable battery and/or a solar battery.

The indicator 297 may display a specific state, for example, a booting state, a message state, a charging state or the like of the electronic device 201 or a part (e.g., processor 210) of the electronic device 201. The motor 298 may convert an electrical signal into a mechanical vibration, and may generate a vibration, a haptic effect or the like. The electronic device 201 may, for example, include a mobile TV support device (e.g., GPU) capable of processing media data according to the standards of digital multimedia broadcasting (DMB), digital video broadcasting (DVB), mediaFlo™ or the like. Each of the constituent elements described in the present document may consist of one or more components, and a name of the corresponding constituent element may be varied according to the kind of the electronic device. In various embodiments, the electronic device (e.g., electronic device 201) may omit some constituent elements, or further include additional constituent elements, or combine some of the constituent elements to configure one entity, but identically perform functions of corresponding constituent elements before combination.

Figure 3:
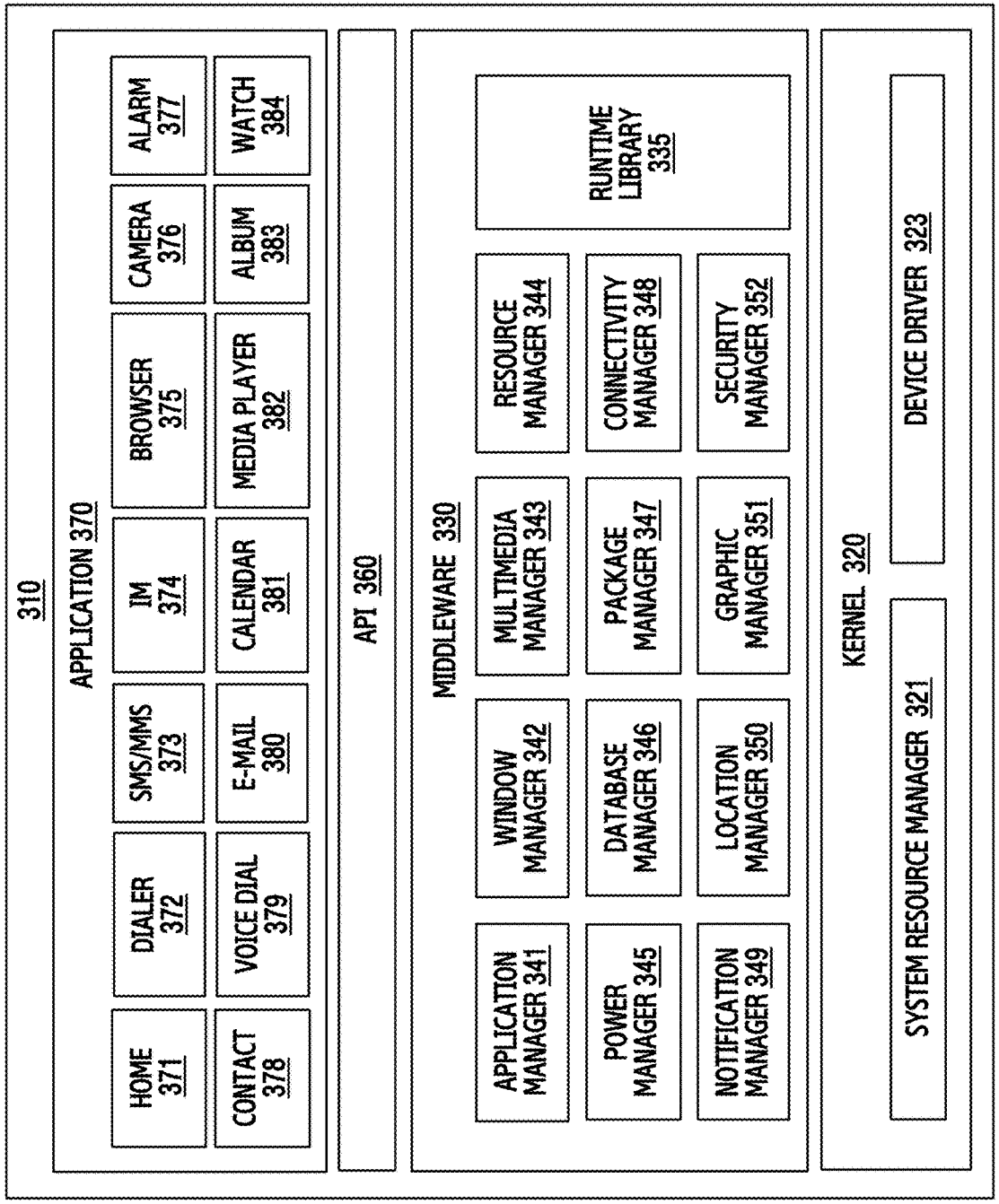
FIG. 3 is a block diagram of a program module according to an embodiment of the present disclosure.

FIG. 3 is a block diagram of a program module according to an embodiment of the present disclosure.

Referring to FIG. 3, a program module 310 (e.g., the program 140) may include an Operating System (OS) for controlling resources related to an electronic device (e.g., the electronic device 101) and/or various applications (e.g., the application program 147) driven on the operating system. The operating system may, for example, include Android™, iOS™, Windows™, Symbian™, Tizen™ or Bada™. Referring to FIG. 3, the program module 310 may include a kernel 320 (e.g., the kernel 141), a middleware 330 (e.g., the middleware 143), an API 360 (e.g., the API 145), and/or an application 370 (e.g., the application program 147). At least a part of the program module 310 may be preloaded onto an electronic device, or be downloaded from an external electronic device (e.g., the external electronic device 102, 104, the server 106, etc.).

The kernel 320 may, for example, include a system resource manager 321 and/or a device driver 323. The system resource manager 321 may perform control of a system resource, allocation thereof, recovery thereof or the like. According to an embodiment, the system resource manager 321 may include a process management unit, a memory management unit or a file system management unit. The device driver 323 may, for example, include a display driver, a camera driver, a Bluetooth driver, a shared memory driver, a USB driver, a keypad driver, a WiFi driver, an audio driver or an inter-process communication (IPC) driver. The middleware 330 may, for example, provide a function that the application 370 commonly needs, or provide various functions to the application 370 through the API 360 so that the application 370 may make use of restricted system resources within an electronic device. According to an embodiment, the middleware 330 may include at least one of a runtime library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351 or a security manager 352.

The runtime library 335 may, for example, include a library module that a compiler uses to add a new function through a programming language while the application 370 is executed. The runtime library 335 may perform input output management, memory management or arithmetic function processing. The application manager 341 may, for example, manage a lifecycle of the application 370. The window manager 342 may manage a graphic user interface (GUI) resource used by a screen. The multimedia manager 343 may detect a format required for playing media files, and perform encoding or decoding of the media file by using a codec suitable to the corresponding format. The resource manager 344 may manage a source code of the application 370 or a space of a memory. The power manager 345 may, for example, manage a battery capacity or a power supply, and provide power information required for an operation of an electronic device. According to an embodiment, the power manager 345 may interwork with a basic input/output system (BIOS). The database manager 346 may, for example, create, search or change a database that will be used by the application 370. The package manager 347 may manage installation or updating of an application that is distributed in a form of a package file.

The connectivity manager 348 may, for example, manage wireless connectivity. The notification manager 349 may, for example, provide events such as an arrival message, an appointment, a proximity notification, etc. to a user. The location manager 350 may, for example, manage location information of an electronic device. The graphic manager 351 may, for example, manage a graphic effect that will be provided to a user, or a user interface related with this. The security manager 352 may, for example, provide system security or user authentication. According to an embodiment, the middleware 330 may include a telephony manager for managing a voice or video telephony function of an electronic device, or a middleware module capable of forming a combination of functions of the aforementioned constituent elements. According to an embodiment, the middleware 330 may provide a module that is specialized based on the type of an operating system. The middleware 330 may dynamically delete some of the existing constituent elements or add new constituent elements. The API 360 is, for example, a set of API programming functions, and may be provided to have another construction in accordance with the operating system. For example, Android or iOS may provide one API set by platform, and Tizen may provide two or more API sets by platform.

The application 370 may, for example, include a home 371, a dialer 372, a short message service (SMS)/multimedia messaging service (MMS) 373, an instant message (IM) 374, a browser 375, a camera 376, an alarm 377, a contact 378, a voice dial 379, an electronic mail (e-mail) 380, a calendar 381, a media player 382, an album 383, a watch 384, health care (e.g., measuring a momentum, a blood sugar or the like), or an environment information (e.g., air pressure, humidity or temperature information) provision application. According to an embodiment, the application 370 may include an information exchange application that may support information exchange between an electronic device and an external electronic device. The information exchange application may, for example, include a notification relay application for relaying specific information to the external electronic device, or a device management application for managing the external electronic device. For example, the notification relay application may relay notification information generated by another application of an electronic device to an external electronic device, or receive notification information from the external electronic device to provide the received notification information to a user. The device management application may, for example, install, delete or update a function (e.g., turn-on/turn-off of the external electronic device itself (or some constituent components) or adjustment of a brightness (or resolution) of a display) of the external electronic device that communicates with the electronic device, or an application operating in the external electronic device. According to an embodiment, the application 370 may include an application (e.g., a health care application of a mobile medical instrument) designated according to an attribute of the external electronic device. According to an embodiment, the application 370 may include an application received from the external electronic device. At least a part of the program module 310 may be implemented (e.g., executed) by software, firmware, hardware (e.g., the processor 210) or a combination of at least two or more of them, and may include a module for performing one or more functions, a program, a routine, sets of instructions or a process.

The term "module" used in the present document may include a unit consisting of hardware, software or firmware and, for example, may be used interchangeably with the terms "logic", "logic block", "component", "circuit" or the like. The "module" may be an integrally configured component or a standalone unit performing one or more functions or a part thereof. The "module" may be implemented mechanically or electronically and, for example, may include an application-specific integrated circuit (ASIC)

chip, field-programmable gate arrays (FPGAs) or a programmable logic device, which has been known or will be developed in future, performing some operations. At least a part of an apparatus (e.g., modules or functions thereof) or method (e.g., operations) according to various embodiments may, for example, be implemented by an instruction that is stored in a computer-readable storage media in the form of a program module. In case where the instruction is executed by a processor (e.g., the processor 120), the processor may perform a function corresponding to the instruction. The computer-readable recording media may include a hard disk, a floppy disk, a magnetic media (e.g., a magnetic tape), an optical recording media (e.g., a compact disc-read only memory (CD-ROM) or a DVD), a magneto-optical media (e.g., a floptical disk), an internal memory, etc. The instruction may include a code that is made by a compiler or a code that is executable by an interpreter. The module or program module according to various embodiments may include at least one or more of the aforementioned constituent elements, or omit some, or further include another constituent element. Operations carried out by the module, the program module or the another constituent element according to various embodiments may be executed in a sequential, parallel, repeated or heuristic manner, or at least some operations may be executed in different order or be omitted, or another operation may be added.

Figure 4A:
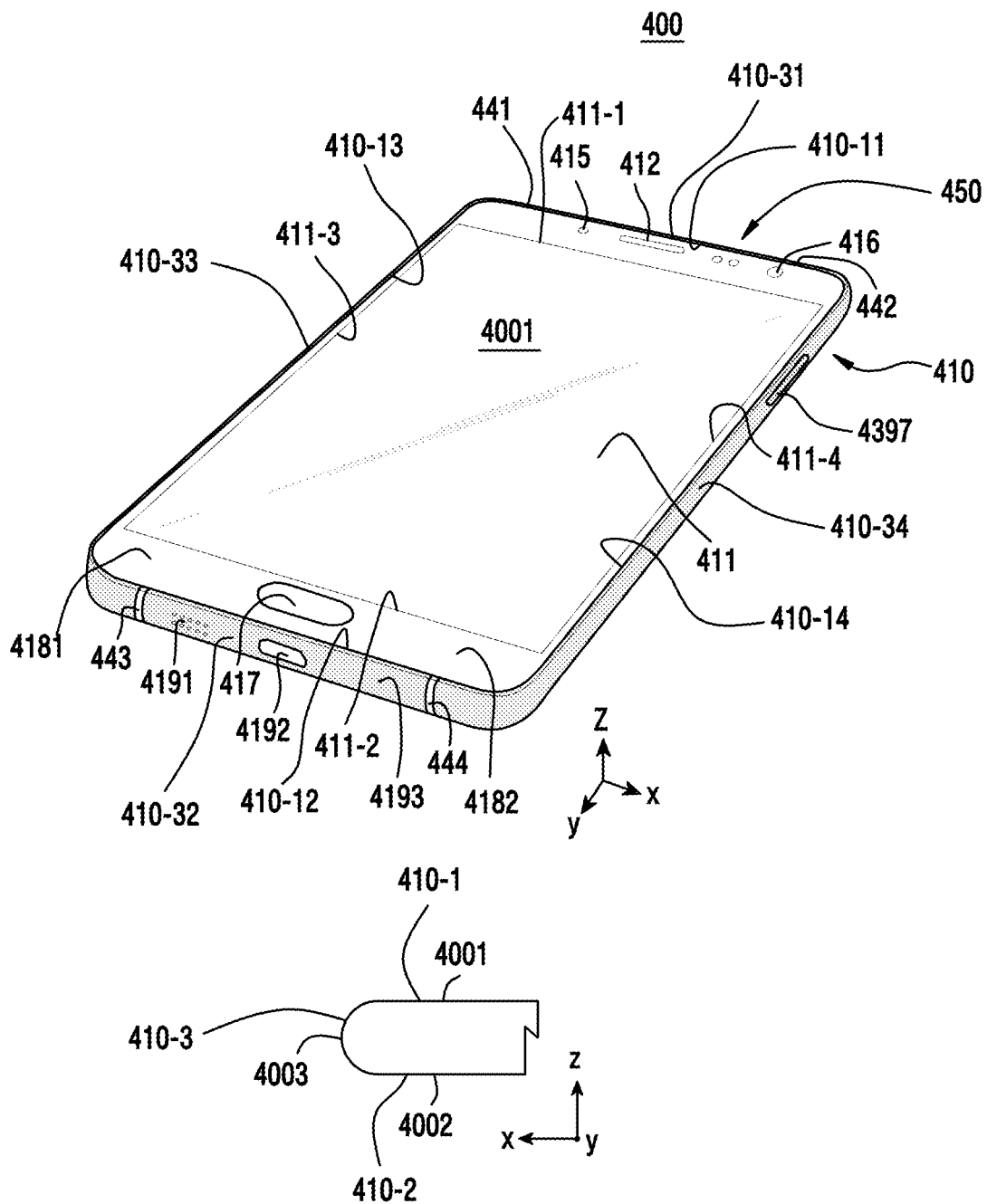
FIG. 4A and FIG. 4B illustrate an electronic device that provides a spectrometric sensing function according to various embodiments of the present disclosure.
Figure 4B:
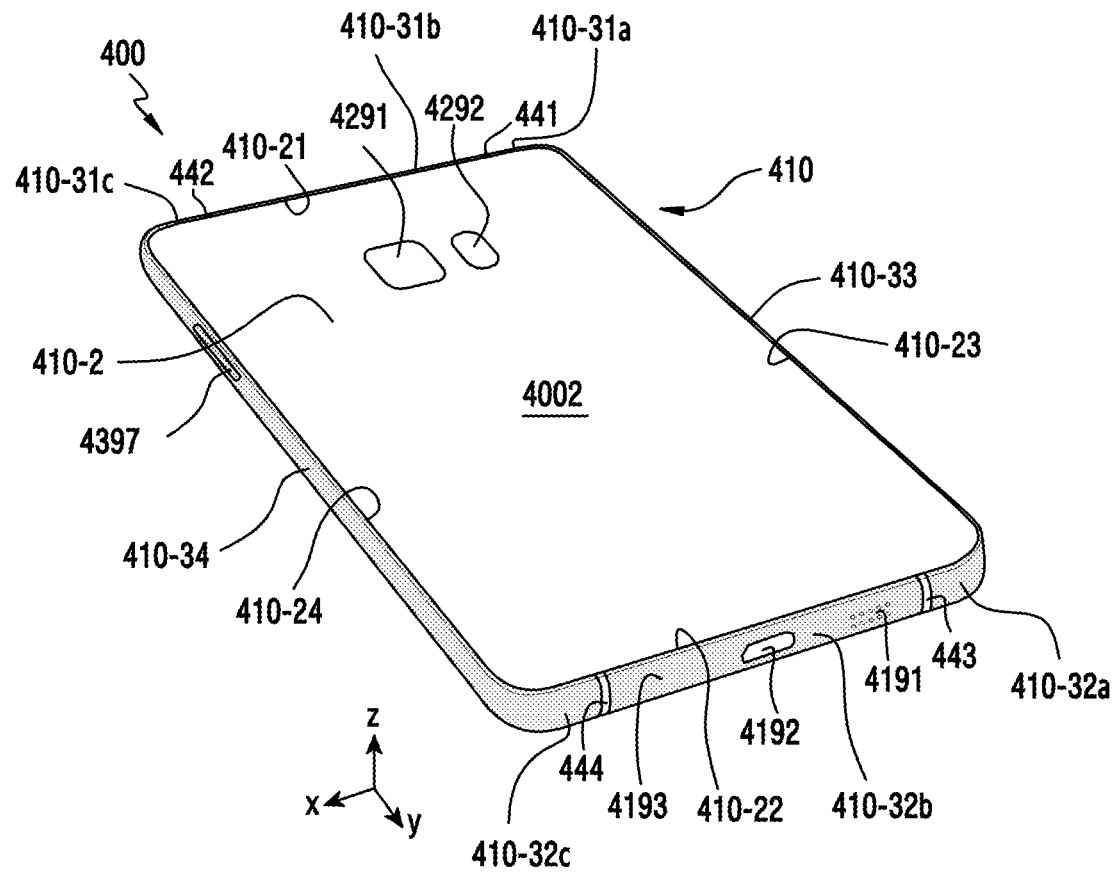
Figure 5A:
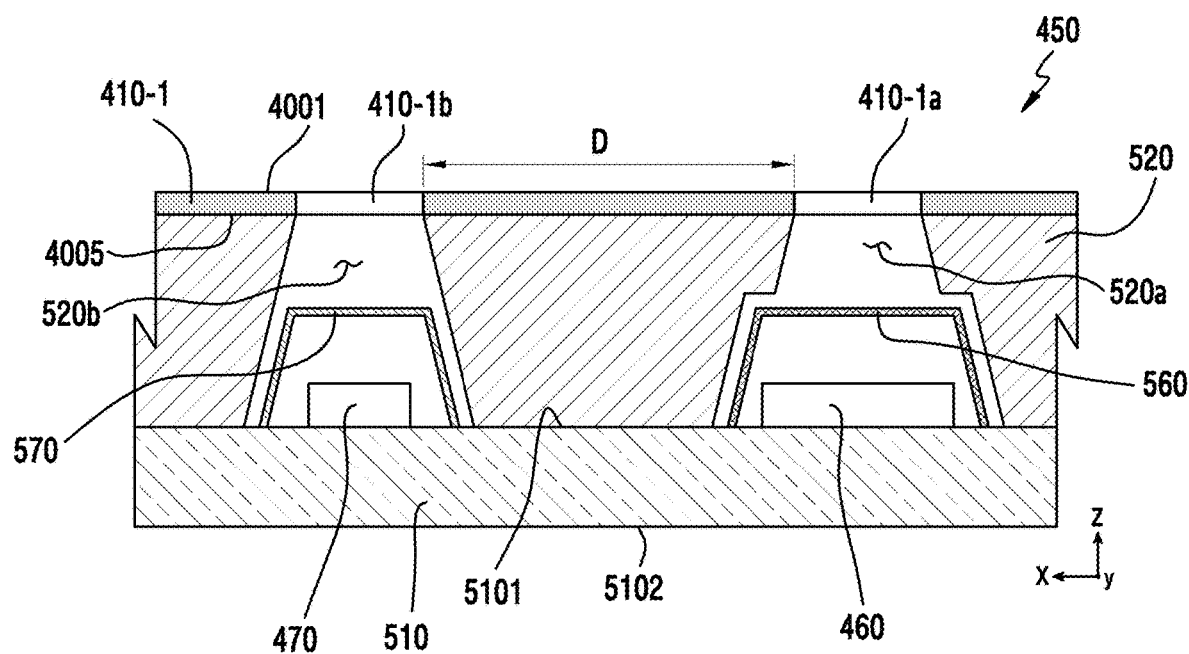
FIG. 5A is a cross section illustrating the structure of a spectrometric sensing apparatus according to an embodiment of the present disclosure.
Figure 5B:
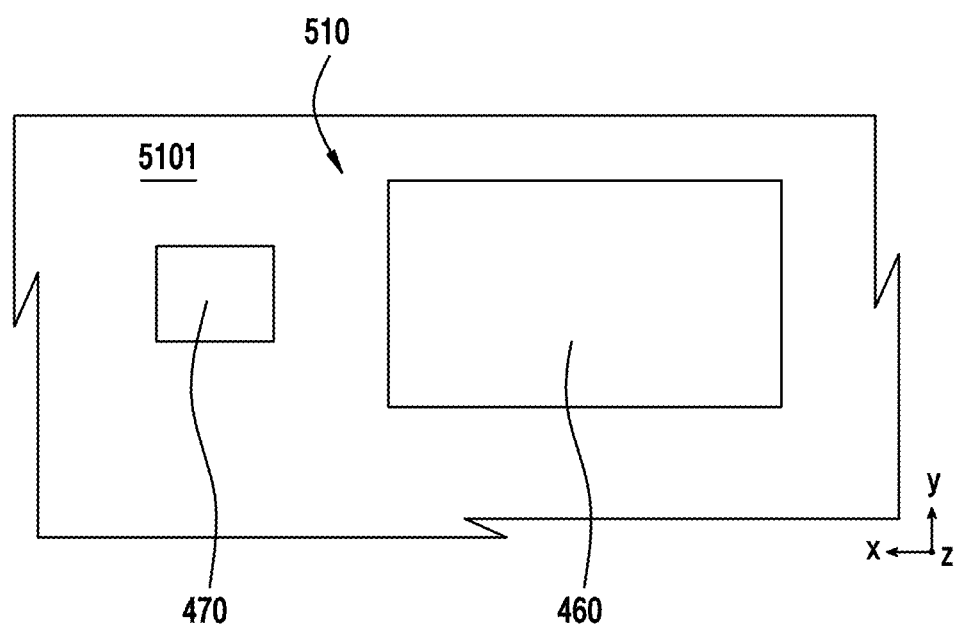
FIG. 5B illustrates a Printed Circuit Board (PCB), and a light receiving unit and light emitting unit disposed therein in a spectrometric sensing apparatus according to an embodiment of the present disclosure.
Figure 5C:
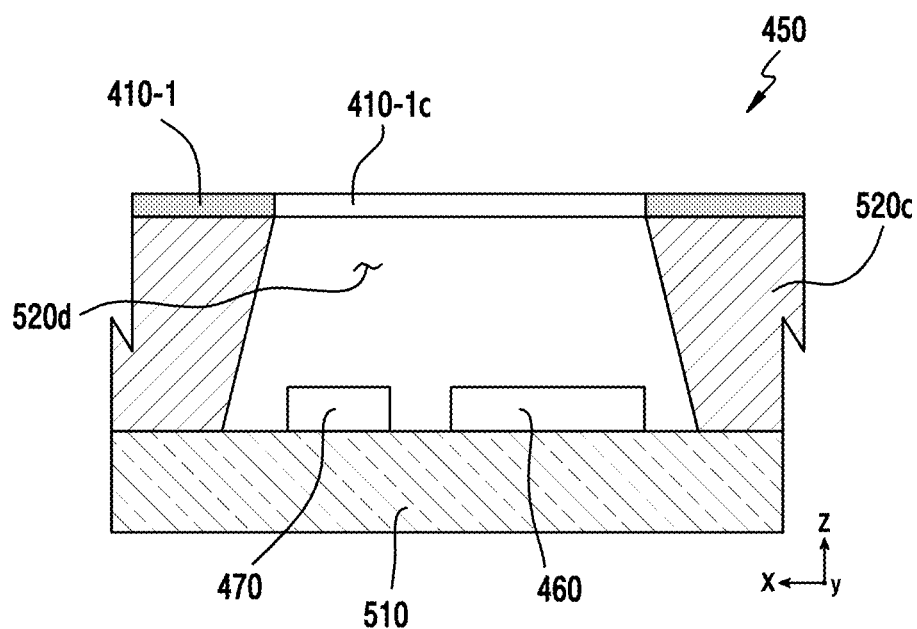
FIG. 5C is a cross section illustrating the structure of a spectrometric sensing apparatus according to an embodiment of the present disclosure.
Figure 5D:
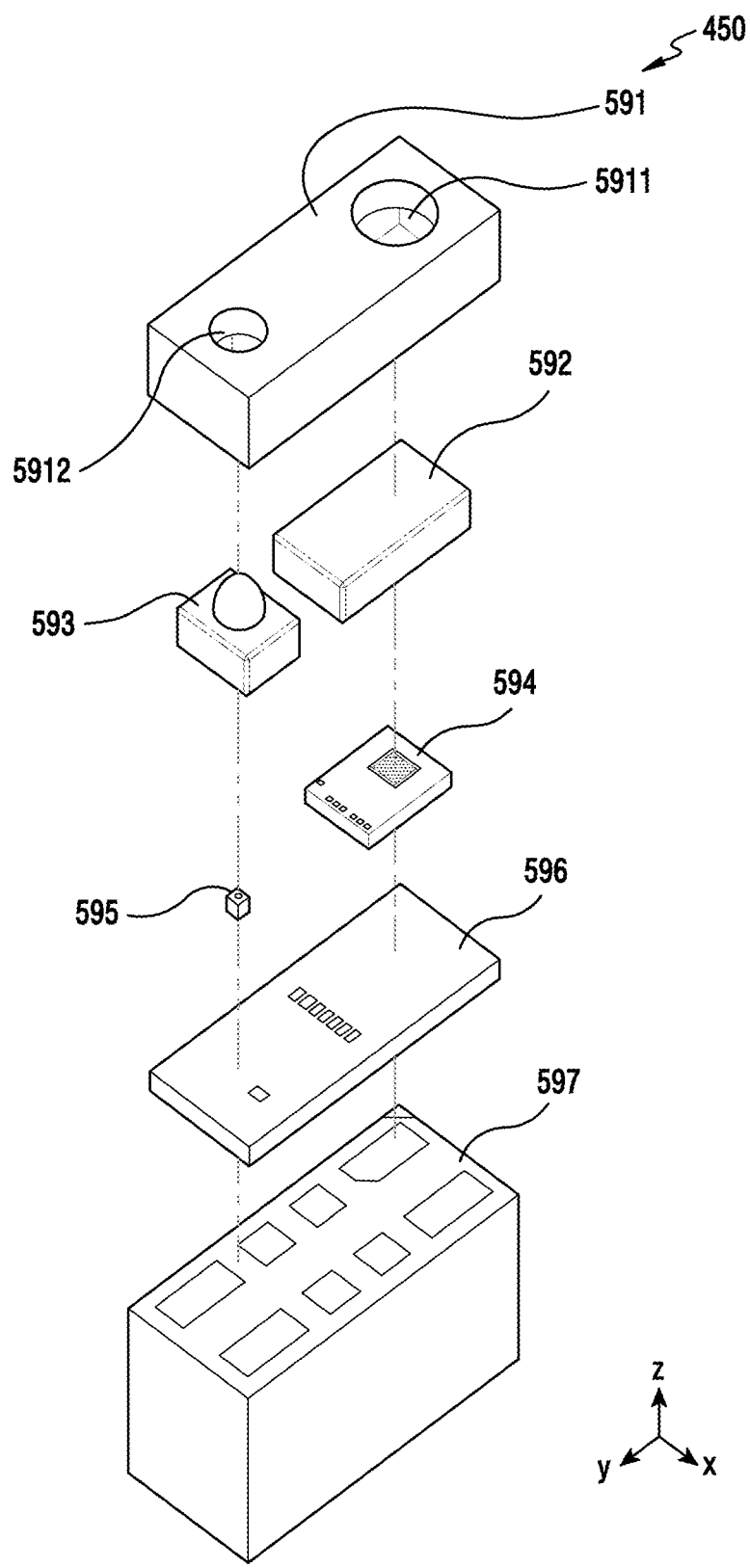
FIG. 5D and FIG. 5E illustrate a spectrometric sensing apparatus according to an embodiment of the present disclosure.
Figure 5E:
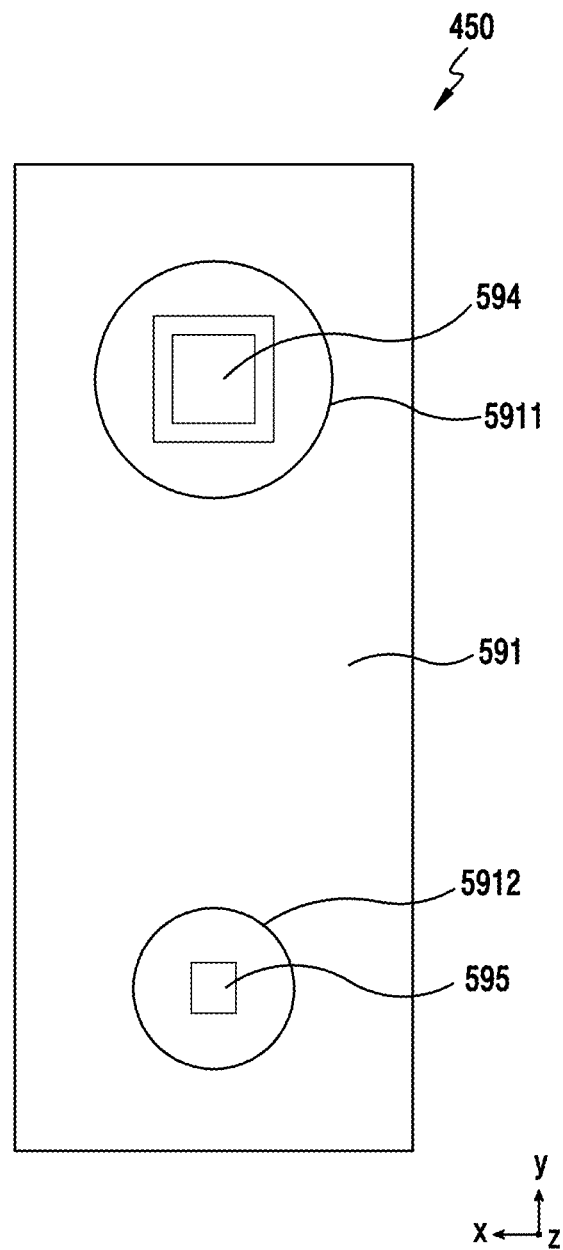

FIGS. 4A and 4B illustrate an electronic device that may provide spectrometric sensing functions according to various embodiments of the present disclosure. FIG. 5A is a cross section illustrating the structure of a spectrometric sensing apparatus according to an embodiment of the present disclosure. FIG. 5B illustrates a Printed Circuit Board (PCB), and a light receiving unit and light emitting unit disposed therein in a spectrometric sensing apparatus according to an embodiment of the present disclosure. FIG. 5C is a cross section illustrating the structure of a spectrometric sensing apparatus according to an embodiment of the present disclosure. FIGS. 5D and 5E illustrate a spectrometric sensing apparatus according to various embodiments of the present disclosure. According to various embodiments, the electronic device 400 may include at least some of the constituent elements of the electronic device 101 of FIG. 1 or the electronic device 201 of FIG. 2.

Referring to FIGS. 4A and 4B, the electronic device 400 may include a housing 410 that forms the entire or at least one portion of the external surface of the electronic device 400. According to various embodiments, the housing 410 may include nonmetallic materials and/or metallic materials. For example, the housing 410 may be formed of materials such as a plastic, a metal, a carbon fiber, other fiber composites, a ceramic, a glass, a timber or a combination of these materials. Or, the housing 410 may be entirely formed of one material or a combination of a plurality of materials. Or, the housing 410 may be partially formed of materials having different physical properties.

According to an embodiment, the housing 410 may form a first surface 4001 of the electronic device 400, a second surface 4002 thereof and a third surface 4003 thereof. The first surface 4001 and the second surface 4002 may face opposite directions, i.e. the first surface 4001 may be the top surface of the electronic device 400 and the second surface 4002 may be the bottom surface thereof. The third surface 4003 may be a surface connecting the first surface 4001 and the second surface 4002.

According to an embodiment, the first surface 4001 and/or second surface 4002 of the housing 410 may be substantially flat surfaces. The third surface 4003 of the housing 410 may be a flat surface (not shown) or a curved surface (shown in FIGS. 4A and 4B).

According to an embodiment, the housing 410 may include a first cover 410-1 forming the first surface 4001, and a second cover 410-2 forming the second surface 4002. The housing 410 may include a bezel (or a side member) 410-3 that surrounds a space between the first cover 410-1 and the second cover 410-2 and forms the third surface 4003.

According to an embodiment, the electronic device 400 may include a display 411 that is built in a space provided by the first cover 410-1 and second cover 410-2 of the housing 410. A screen region of the display 411 may be exposed to the exterior through the first cover 410-1. According to various embodiments, the display 411 may further include a touch sensing device for a touch input and/or a hovering input. For example, if a finger or a stylus comes in contact with the first surface 4001, the electronic device 400 may sense a touch input through the display 411. In accordance with various embodiments of the present disclosure, if the finger or stylus is close to the first surface 4001, the electronic device 400 may sense a hovering input using the display 411.

According to an embodiment, a screen region of the display 411 may be a roughly rectangular form that includes a first short side 411-1, a second short side 411-2, a first long side 411-3 and a second long side 411-4.

According to an embodiment, the first cover 410-1 may be a roughly rectangular form that includes an edge 410-11 corresponding to the first short side 411-1 of the screen region, an edge 410-12 corresponding to the second short side 411-2 of the screen region, an edge 410-13 corresponding to the first long side 411-3 of the screen region, and an edge 410-14 corresponding to the second long side 411-4 of the screen region. The edge 410-13 may connect one end of the edge 410-11 and one end of the edge 410-12. The edge 410-14 may connect the other end of the edge 410-11 and the other end of the edge 410-12. A connection portion between the edge 410-11 and the edge 410-13 may be a curve form. A connection portion between the edge 410-11 and the edge 410-14 may be a curve form. A connection portion between the edge 410-12 and the edge 410-13 may be a curve form. According to various embodiments, a connection portion between the edge 410-12 and the edge 410-14 may be a curve form.

According to an embodiment, when viewing in the direction going from the first cover 410-1 to the second cover 410-2, the second cover 410-2 may be a roughly rectangular form corresponding to the first cover 410-1.

According to an embodiment, the second cover 410-2 may be a roughly rectangular form that includes an edge 410-21 corresponding to the edge 410-11 of the first cover 410-1, an edge 410-22 corresponding to the edge 410-12 of the first cover 410-1, an edge 410-23 corresponding to the edge 410-13 of the first cover 410-1, and an edge 410-24 corresponding to the edge 410-14 of the first cover 410-1. The edge 410-23 may connect one end of the edge 410-21 and one end of the edge 410-22. The edge 410-24 may connect the other end of the edge 410-21 and the other end of the edge 410-22. A connection portion between the edge 410-21 and the edge 410-23 may be a curve form. A connection portion between the edge 410-21 and the edge 410-24 may be a curve form. A connection portion between the edge 410-22 and the edge 410-23 may be a curve form. A connection portion between the edge 410-22 and the edge 410-24 may be a curve form.

According to various embodiments, the electronic device 400 may include various components (e.g., a camera 4291 and a flash 4292) that are disposed between the first cover 410-1 and the second cover 410-2.

According to an embodiment, the first cover 410-1 and/or the second cover 410-2 may be formed of light transmission materials (e.g., glass).

According to an embodiment, the bezel 410-3 may include a first metal frame 410-31 that connects the edge 410-11 of the first cover 410-1 and the edge 410-21 of the second cover 410-2. The bezel 410-3 may include a second metal frame 410-32 that connects the edge 410-12 of the first cover 410-1 and the edge 410-22 of the second cover 410-2. The bezel 410-3 may include a third metal frame 410-33 that connects the edge 410-13 of the first cover 410-1 and the edge 410-23 of the second cover 410-2. The bezel 410-3 may include a fourth metal frame 410-34 that connects the edge 410-14 of the first cover 410-1 and the edge 410-24 of the second cover 410-2. The first metal frame 410-31 and the second metal frame 410-32 may be disposed at opposite sides of the electronic device 400 (i.e. the top and bottom sides), and the third metal frame 410-33 and the fourth metal frame 410-34 may be disposed at opposite sides of the electronic device 400 (i.e. the left and right sides). The first metal frame 410-31 may connect one end of the third metal frame 410-33 and one end of the fourth metal frame 410-34. The second metal frame 410-32 may connect the other end of the third metal frame 410-33 and the other end of the fourth metal frame 410-34. A combination of the first metal frame 410-31, the second metal frame 410-32, the third metal frame 410-33 and the fourth metal frame 410-34 may form a roughly rectangular ring shape. Accordingly, the third surface 4003 of the housing 410 formed by the bezel 410-3 may also have a roughly rectangular ring shape.

According to various embodiments, a connection portion between the first metal frame 410-31 of the bezel 410-3 and the third metal frame 410-33 thereof may be curved. A connection portion between the first metal frame 410-31 of the bezel 410-3 and the fourth metal frame 410-34 thereof may be curved. A connection portion between the second metal frame 410-32 of the bezel 410-3 and the third metal frame 410-33 thereof may be curved. A connection portion between the second metal frame 410-32 of the bezel 410-3 and the fourth metal frame 410-34 thereof may be curved.

According to various embodiments, though not illustrated, the bezel 410-3 may include an extension portion (not shown) that is extended towards the inside of the housing 410 from at least one of the first metal frame 410-31, the second metal frame 410-32, the third metal frame 410-33 and the fourth metal frame 410-34. The extension portion may be combined with a Printed Circuit Board (PCB), a bracket, etc. inside the housing 410.

According to an embodiment, at least one of the first metal frame 410-31, second metal frame 410-32, third metal frame 410-33 and fourth metal frame 410-34 of the bezel 410-3 may include a plurality of metal portions that are mutually physically isolated. According to various embodiments, a nonconductive member may be disposed between the plurality of metal portions. The nonconductive member may form a part of the third surface 4003 of the housing 410. In other embodiments, the nonconductive member may be a member that is extended from a nonconductive portion disposed within the housing 410.

According to an embodiment, the first metal frame 410-31 of the bezel 410-3 may include a metal frame 410-31a, a metal frame 410-31b and a metal frame 410-31c that are mutually physically isolated. The metal frame 410-31b may be disposed between the metal frame 410-31a and the metal frame 410-31c.

According to an embodiment, the metal frame 410-31a of the first metal frame 410-31 may be connected to the third metal frame 410-33. The metal frame 410-31c of the first metal frame 410-31 may be connected to the fourth metal frame 410-34. The metal frame 410-31a and the third metal frame 410-33 may be one piece of metal. The metal frame 410-31c and the fourth metal frame 410-34 may be one piece of metal.

According to an embodiment, the electronic device 400 may include a first nonconductive member 441 that is disposed between the metal frame 410-31a of the bezel 410-3 and the metal frame 410-31b thereof. The electronic device 400 may include a second nonconductive member 442 that is disposed between the metal frame 410-31b and the metal frame 410-31c. The first nonconductive member 441 and the second nonconductive member 442 may be smoothly connected with the first metal frame 410-31, and form a part of the third surface 4003 of the first housing 410. The first nonconductive member 441 and/or the second nonconductive member 442 may be portions that are extended from a nonconductive member disposed within the housing 410.

According to an embodiment, a first gap (not shown) between the metal frame 410-31a and the metal frame 410-31b may be a portion filled with the first nonconductive member 441. A second gap (not shown) between the metal frame 410-31b and the metal frame 410-31c may be a portion filled with the second nonconductive member 442. The first gap and the second gap may have the same or different widths.

According to an embodiment, the second metal frame 410-32 of the bezel 410-3 may include a metal frame 410-32a, a metal frame 410-32b and a metal frame 410-32c that are mutually physically isolated. The metal frame 410-32b may be disposed between the metal frame 410-32a and the metal frame 410-31c.

According to an embodiment, the metal frame 410-32a of the second metal frame 410-32 may be connected to the third metal frame 410-33. The metal frame 410-32c of the second metal frame 410-32 may be connected to the fourth metal frame 410-34. The metal frame 410-32a and the third metal frame 410-33 may be one piece of metal. The metal frame 410-32c and the fourth metal frame 410-34 may be one piece of metal.

According to an embodiment, the electronic device 400 may include a third nonconductive member 443 that is disposed between the metal frame 410-32a of the bezel 410-3 and the metal frame 410-32b thereof. The electronic device 400 may include a fourth nonconductive member 444 that is disposed between the metal frame 410-32b and the metal frame 410-32c. The third nonconductive member 443 and the fourth nonconductive member 444 may be smoothly connected with the second metal frame 410-32, and form a part of the third surface 4003 of the housing 410. The third nonconductive member 443 and/or the fourth nonconductive member 444 may be portions that are extended from a nonconductive member disposed within the housing 410.

According to an embodiment, a third gap (not shown) between the metal frame 410-32a and the metal frame 410-32b may be a portion filled with the third nonconductive member 443. A fourth gap (not shown) between the metal frame 410-32b and the metal frame 410-32c may be a portion filled with the fourth nonconductive member 444. The third gap and the fourth gap may have the same or different widths.

According to various embodiments, the electronic device 400 may include various forms of components that use the bezel 410-3. For example, the metal frame 410-32b of the bezel 410-3 may include a plurality of through-holes 4191 for supporting a speaker (not shown). Sound from the speaker mounted within the electronic device 400 may be discharged through the plurality of through-holes 4191. As another example, the metal frame 410-32b of the bezel 410-3 may include a through-hole 4193 for supporting a microphone (not shown). External sound may be transmitted to the microphone mounted within the electronic device 400 through the through-hole 4193. In another example, the metal frame 410-32b of the bezel 410-3 may include a through-hole 4192 for supporting a connector (not shown). A connector of an external device may be connected to the connector that is mounted within the electronic device 400 through the through-hole 4192. In another example, the fourth metal frame 410-34 of the bezel 410-3 may include a through-hole for supporting a button 4397. The third metal frame 410-33 of the bezel 410-3 may also include a through-hole for supporting a button (not shown).

According to an embodiment, in a top view of the electronic device 400, the electronic device 400 may include various components that are disposed between the edge 410-12 of the first cover 410-1 and the second short side 411-2 of the screen region. For example, the components may be various input keys. The input key may be a depressible button (e.g., a home button 417). In the alternative, the input key may be a touch key 4181 or 4182.

According to an embodiment, in a top view of the electronic device 400, the electronic device 400 may include various components that are disposed between the edge 410-11 of the first cover 410-1 and the first short side 411-1 of the screen region. For example, the components may include a receiver (i.e. a speaker) 412 for acoustically outputting a voice signal received from a counterpart device during a phone call. The components may also include a camera module 416. The components may also include a light emitting element (e.g., LED) 415 that indicates various states of the electronic device 400. For example, in accordance with user configuration setting, the electronic device 400 may turn on the light emitting element 415 when the battery level is low. In accordance with another user configuration setting, the electronic device 400 may turn on the light emitting element 415 only when the screen is off. In accordance with another user configuration setting, the electronic device 400 may turn on the light emitting element 415 if the electronic device 400 is connected to an electric charger. The electronic device 400 may enable the light emitting element 415 to emit light in various colors in accordance with various states of the electronic device 400.

According to an embodiment, in a top view of the electronic device 400, the electronic device 400 may include a spectrometric sensing apparatus 450 that is disposed between the edge 410-11 of the first cover 410-1 and the first short side 411-1 of the screen region. The spectrometric sensing apparatus 450 may measure intensities, etc., of various wavelength bands of light. And, the electronic device 400 may quantitatively or qualitatively analyze the data measured from the spectrometric sensing apparatus 450.

According to an embodiment, in a top view of the electronic device 400, the spectrometric sensing apparatus 450 may be disposed between the receiver 412 and the camera module 416.

According to an embodiment, the spectrometric sensing apparatus 450 may send light out through at least one of one or more light transmission regions formed in the first cover 410-1, and receive light through the light transmission regions.

FIG. 5A is a section illustrating a structure of the spectrometric sensing apparatus 450 according to an embodiment of the present disclosure. FIG. 5B illustrates a PCB, and a light receiving unit and light emitting unit disposed therein in the spectrometric sensing apparatus 450 according to an embodiment of the present disclosure.

Referring to FIG. 5A and FIG. 5B, the spectrometric sensing apparatus 450 according to an embodiment may include a light receiving unit 460 and a light emitting unit 470. The light receiving unit 460 may convert light energy (light signal or optical signal) into electrical energy (or electrical signal). The light emitting unit 470 may convert electrical energy into light energy. Light (e.g., ultraviolet rays, visible rays, infrared rays or the like) from the light emitting unit 470 may be irradiated onto an object external to and/or near the electronic device 400, and the reflected light thereof may be received by the light receiving unit 460.

According to an embodiment, the light receiving unit 460 and the light emitting unit 470 may be disposed on the PCB 510 of the electronic device 400, and be electrically connected to the PCB 510. For example, the PCB 510 may include a first surface 5101 facing the first surface 4001 of the electronic device 400, and a second surface 5102 facing the second surface 4002 of the electronic device 400. The light receiving unit 460 and the light emitting unit 470 may be disposed in the first surface 5101 of the PCB 510, and be disposed between the first cover 410-1 and the PCB 510.

According to an embodiment, the spectrometric sensing apparatus 450 may include a first light transmission region 410-1a that is provided in the first cover 410-1. In a top view of the electronic device 400, the first light transmission region 410-1a may be disposed between the edge 410-11 of the first cover 410-1 and the first short side 411-1 of the screen region. When viewing from a cross section as shown in FIG. 5A, the first light transmission region 410-1a and the light receiving unit 460 may be aligned vertically with each other. Light from the exterior of the electronic device 400 may be transmitted to the light receiving unit 460 through the first light transmission region 410-1a.

According to an embodiment, the spectrometric sensing apparatus 450 may include a second light transmission region 410-1b that is provided in the first cover 410-1. In a top view of the electronic device 400, the second light transmission region 410-1b may be disposed between the edge 410-11 of the first cover 410-1 and the first short side 411-1 of the screen region. When viewing from a cross section as shown in FIG. 5A, the second light transmission region 410-1b and the light emitting unit 470 may be aligned vertically with each other. Light generated from the light emitting unit 470 may be discharged through the second light transmission region 410-1b.

In a top view of the electronic device 400, a region between the edge 410-11 of the first cover 410-1 and the first short side 411-1 of the screen region may have a shape that is relatively long in the direction (e.g., x-axis direction) going from the edge 410-13 of the first cover 410-1 to the edge 410-14, and may be divided into a left region (not shown) located near the edge 410-13 side and a right region (not shown) located near the edge 410-14 side. According to an embodiment, when the receiver 412 is in the right region, the first light transmission region 410-1a and the second light transmission region 410-1b may also be disposed in the right region.

According to an embodiment, as illustrated, in a top view of the electronic device 400, the second light transmission region 410-1b may be disposed between the receiver 412 and the first light transmission region 410-1a.

According to another embodiment, though not illustrated, in a top view of the electronic device 400, the first light transmission region 410-1a may be disposed between the receiver 412 and the second light transmission region 410-1b. If the position of the first light transmission region 410-1a is changed, positions of constituent elements (e.g., the first penetration part 520a, the first light transmitting member 560 and the light receiving unit 460) associated with the first light transmission region 410-1a may be changed also.

According to an embodiment, as illustrated, the first light transmission region 410-1a and the second light transmission region 410-1b may be aligned in the direction going from the edge 410-14 of the first cover 410-1 to the edge 410-13 thereof (e.g., x-axis direction). A distance (D) between the first light transmission region 410-1a and the second light transmission region 410-1b may be about 10 millimeters (mm) or less, for example.

According to various embodiments, though not illustrated, the first light transmission region 410-1a and the second light transmission region 410-1b may be designed to be aligned in the direction going from the edge 410-12 of the first cover 410-1 to the edge 410-11 thereof (e.g., y-axis direction).

According to various embodiments, in a top view of the electronic device 400, the first light transmission region 410-1a and the second light transmission region 410-1b may be roughly circular in shape, or may be in other various shapes.

According to various embodiments, in a top view of the electronic device 400, the first light transmission region 410-1a and the second light transmission region 410-1b may have the same or different sizes.

According to various embodiments, the light receiving unit 460, the light emitting unit 470, and the first light transmission region 410-1a and second light transmission region 410-1b associated thereof may be disposed to have various different positions or forms not illustrated, without being limited to the embodiment of FIG. 5A.

According to various embodiments, the first light transmission region 410-1a and/or the second light transmission region 410-1b may be designed to have materials or a shape that may transmit light without light deformation (e.g., distortion, absorption, etc.). For example, the first light transmission region 410-1a and/or the second light transmission region 410-1b may have a high light transmittance (e.g., about 90% or more) or a low light reflectance (e.g., about 5% or less). For one example, when viewing from the cross section as shown in FIG. 5A, the first light transmission region 410-1a and/or the second light transmission region 410-1b may be flat shapes that have roughly constant thicknesses as illustrated, or, though not illustrated, may be also shapes that are convex towards the object that light is transmitted to, for example, in the direction going from the first cover 410-1 to the second cover 410-2.

According to various embodiments, in a top view of the electronic device 400, the portion of the region between the edge 410-11 of the first cover 410-1 and the first short side 411-1 of the screen region that is not the first light transmission region 410-1a and the second light transmission region 410-1b may be designed to be opaque. For example, a black layer may be combined to a part of an inner surface 4005 of the first cover 410-1.

According to an embodiment, when viewing from the cross section as shown in FIG. 5A, the spectrometric sensing apparatus 450 may further include a spacer 520 that is disposed between the first cover 410-1 and the PCB 510. The spacer 520 may include the first penetration part 520a and a second penetration part 520b. The first penetration part 520a may provide a space between the light receiving unit 460 and the first light transmission region 410-1a. Light from the exterior may be transmitted to the light receiving unit 460 through the first penetration part 520a. The second penetration part 520b may provide a space between the light emitting unit 470 and the second light transmission region 410-1b. The light output from the light emitting unit 470 may emitted the outside through the second penetration part 520b.

According to various embodiments, the first penetration part 520a may be designed so that light from the exterior may be transmitted to the light receiving unit 460 without significant light deformation (e.g., distortion, absorption, etc.). According to various embodiments of the present disclosure, the second penetration part 520b may be designed so that light from the light emitting unit 470 may be discharged out without significant light deformation. For example, the first penetration part 520a may include materials or be of a shape for reducing the absorption of light of a plurality of wavelength bands that may be detected by the light receiving unit 460. The second penetration part 520b may include materials or be of a shape for reducing the absorption of light of one or more wavelength bands that are discharged by the light emitting unit 470. According to various embodiments, the first penetration part 520a and/or the second penetration part 520b may be of a shape that becomes narrower towards the first cover 410-1, as shown in FIG. 5A.

According to various embodiments, the spacer 520 may support not only the spectrometric sensing apparatus 450, but other components or devices (e.g., the light emitting element 415, the receiver 412, the camera module 416, etc.) that are installed adjacently to the edge 410-11 of the first cover 410-1. For example, the spacer 520 may include a part (not shown) for supporting the receiver 412.

According to an embodiment, the spectrometric sensing apparatus 450 may further include the first light transmitting member 560 (e.g., a lens) that is disposed between the first cover 410-1 and the PCB 510. For example, the first light transmitting member 560 may be disposed in a space of the first penetration part 520a of the spacer 520. The first light transmitting member 560 may cover the light receiving unit 460 disposed in the PCB 510, and be designed so that external light (i.e. light from the exterior of the electronic device 400) may be transmitted to the light receiving unit 460 without significant light deformation. According to various embodiments, the first light transmitting member 560 may be designed to refract light such that the external light is concentrated on the light receiving unit 460.

According to an embodiment, the spectrometric sensing apparatus 450 may further include a second light transmitting member 570 that is disposed between the first cover 410-1 and the PCB 510. For example, the second light transmitting member 570 may be disposed in a space of the second penetration part 520b of the spacer 520. The second light transmitting member 570 may cover the light emitting unit 470 disposed in the PCB 510, and be designed so that light from the light emitting unit 470 may be discharged without significant light deformation. For example, the second light transmitting member 570 may enable light from the light emitting unit 470 to have linearity when the light is discharged out. However, the first light transmitting member 560 or the second light transmitting member 570 may not be necessary and in one embodiment, the first light transmitting member 560 or the second light transmitting member 570 may be omitted.

According to an embodiment, the light receiving unit 460 may include one or more light detectors (photo detectors or light sensors) (not shown) that may detect light signals of one or more wavelength bands.

According to an embodiment, the light receiving unit 460 may include a plurality of light detectors, and the plurality of light detectors may detect light signals of various wavelengths. For example, one light detector may detect a light signal of a first wavelength band, and another light detector may detect a light signal of a second wavelength band that is different from the first wavelength band.

According to an embodiment, the light receiving unit 460 may include a plurality of light detectors, and the plurality of light detectors may detect light signals of similar or identical wavelengths as well. For example, one light detector may detect a light signal of a first wavelength band. Another light detector may detect a light signal of the first wavelength band as well as a light signal of a second wavelength band that is different from the first wavelength band. A further light detector may detect the light signal of the first wavelength band as well as a light signal of a third wavelength band that is different from the first and second wavelength bands. A yet another light detector may detect the light signal of the first wavelength band as well as a light signal of a fourth wavelength band that is different from the first, second and third wavelength bands.

According to an embodiment, the light receiving unit 460 may include one or more light filters not shown. At least one light filter may be disposed between the first surface 4001 and the light detectors. The light filter may be an element for selectively transmitting and/or stopping transmitting light of a particular wavelength band. According to various embodiments, the light detector may be integrated with the light filter.

For example, the light detector may be designed to detect a light signal of one wavelength band, so the light detector may include a light filter (or optical filter) that transmits only the light in that wavelength band.

For another example, the light detector may be designed to detect light signals of at least two or more wavelength bands, so the light detector may include a light filter or filters that transmit only light in those two or more wavelength bands.

According to an embodiment, the light receiving unit 460 may detect a light signal of a proximity detecting wavelength band. For example, in a proximity detection mode, if a thing (e.g., a user face) is moved within the vicinity (e.g., 10 cm or less) of the spectrometric sensing apparatus 450, light of a proximity detecting wavelength band (e.g., a maximum sensitivity wavelength 940 nm or 950 nm) discharged from the light emitting unit 470 may be reflected from the thing. The reflected light of the proximity detecting wavelength band may be transmitted into the light receiving unit 460, and the light receiving unit 460 may generate an electrical signal to detect proximity of the thing, such as the proximity distance of the thing.

According to an embodiment, the light receiving unit 460 may detect a light signal of a gesture detecting wavelength band (e.g., a maximum sensitivity wavelength about 940 nm). For example, in a gesture detection mode, if a user hand is moved in the vicinity (e.g., within about 10 cm) of the first surface 4001 of the electronic device 400, light of the gesture detecting wavelength band (e.g., about 940 nm) discharged from the light emitting unit 470 may be reflected from the user hand. The reflected light of the gesture detecting wavelength band may be transmitted into the light receiving unit 460, and the light receiving unit 460 may generate an electrical signal for a gesture of the user hand.

According to an embodiment, the light receiving unit 460 may detect a light signal of a thing analyzing wavelength band. For example, in a biometric detection mode, if the user body is moved to the vicinity (e.g., about 10 cm or less) of the spectrometric sensing apparatus 450, light of a biometric wavelength band discharged from the light emitting unit 470 may be reflected from the user body. The reflected light of the biometric wavelength band may be transmitted into the light receiving unit 460, and the light receiving unit 460 may detect the reflected light, to convert the detected light into an electrical signal for a medical state (e.g., skin moisture, skin melanin, skin temperature, heart rate, blood flow speed, etc.) of the user body.

According to an embodiment, the light receiving unit 460 may detect a light signal of an external environment measuring wavelength band. For example, in an illuminance detection mode, the light receiving unit 460 may detect external light, and convert the detected light into an electrical signal signaling the illuminance of the environment surrounding the electronic device 400.

According to an embodiment, the light receiving unit 460 may be designed to detect one or more of the wavelength bands described above. For example, the light receiving unit 460 may detect not only a light signal of a proximity (or gesture) detecting wavelength band, but also a light signal of a biometric detecting wavelength band. For example, the light receiving unit 460 may detect not only a light signal of an illuminance detecting wavelength band, but also a light signal of a biometric detecting wavelength band.

According to various embodiments, the electronic device 400 may provide various detection modes. For example, the detection mode may be various such as a proximity detection mode, a gesture detection mode, a biometric detection mode, an illuminance detection mode, etc. The detection mode may include a diversity of auxiliary detection modes as well. For example, the biometric detection mode may be various such as a skin moisture detection mode, a skin melanin detection mode, a skin temperature detection mode, etc.

According to various embodiments, the electronic device 400 may provide various multi detection modes. The multi detection mode may indicate a selection of a plurality of detection modes. For example, the multi detection mode may include the proximity detection mode and the biometric detection mode. The multi detection mode may further include the illuminance detection mode and the biometric detection mode. The multi detection mode may also include a selection of many of auxiliary detection modes within the detection mode.

According to an embodiment, the electronic device 400 may select and activate at least a part of the light receiving unit 460 in accordance with the selected detection mode. For example, in the proximity detection mode, a control circuit (e.g., the processor 120 of FIG. 1 or the processor 210 of FIG. 2) may select and activate at least one light detector among a plurality of light detectors of the light receiving unit 460 for proximity detection. In another example, in the gesture detection mode, the control circuit may select and activate at least one light detector among the plurality of light detectors of the light receiving unit 460 for gesture detection. In another example, in the illuminance detection mode, the control circuit may select and activate at least one light detector among the plurality of light detectors of the light receiving unit 460 for illuminance detection. In another example, in the biometric detection mode, the control circuit may select and activate at least one light detector among the plurality of light detectors of the light receiving unit 460 for biometric detection.

The light emitting unit 470 may include at least one light emitter (or light source) that may generate light of one or more wavelength bands.

According to an embodiment, the light emitting unit 470 may include a light emitter that may generate light of all wavelength bands at which the light receiving unit 460 may detect light signals. For example, the light emitting unit 470 may be designed as a single light emitter. The single light emitter may be a light emitting element that may generate light of a broad wavelength band.

According to various embodiments, the light emitting unit 470 may be designed to selectively generate light of narrow wavelength bands in accordance with the control of a control circuit (e.g., the processor 120 of FIG. 1 or the processor 210 of FIG. 2). For example, in the proximity detection mode, the control circuit may control the light emitting unit 470 to generate light of the proximity detecting wavelength band. According to various embodiments, in a gesture detection mode, the control circuit may control the light emitting unit 470 to generate light of the gesture detecting wavelength band. According to various embodiments, in the biometric detection mode, the control circuit may control the light emitting unit 470 to generate light of the biometric detecting wavelength band.

According to an embodiment, the light emitting unit 470 may include a plurality of light emitters, and the plurality of light emitters may generate light of different wavelength bands. For example, one light emitter may generate light of a first wavelength band, and another light emitter may generate light of a second wavelength band that is different from the first wavelength band. For example, in the proximity detection mode, the control circuit may select and activate at least one light emitter that generates light of the proximity detecting wavelength band among the plurality of light emitters of the light emitting unit 470. According to various embodiments, in the gesture detection mode, the control circuit may select and activate at least one light emitter that generates light of the gesture detecting wavelength band among the plurality of light emitters of the light emitting unit 470. According to various embodiments, in the biometric detection mode, the control circuit may select and activate at least one light emitter that generates light of the biometric detecting wavelength band among the plurality of light emitters of the light emitting unit 470.

According to various embodiments, the light emitting unit 470 may include various types of light emitting elements. For example, the light emitting unit 470 may include a Light Emitting Diode (LED).

According to another embodiment, the spectrometric sensing apparatus 450 may use one light transmission region that is provided in the first cover 410-1 as well. Referring to FIG. 5C according to an embodiment, the spectrometric sensing apparatus 450 may include a PCB 510, the light receiving unit 460 and light emitting unit 470 disposed in the PCB 510, and the first cover 410-1 including a light transmission region 410-1c. In a top view of the electronic device 400, the light transmission region 410-1c may be disposed between the edge 410-11 of the first cover 410-1 and the first short side 411-1 of the screen region. When viewing from the cross section as shown in FIG. 5C, the light transmission region 410-1c may be aligned vertically with the light receiving unit 460 and the light emitting unit 470. Light generated from the light emitting unit 470 may be discharged through the light transmission region 410-1c. Likewise, external light may be transmitted to the light receiving unit 460 through the light transmission region 410-1c.

According to various embodiments, when viewing from the cross section as shown in FIG. 5C, the spectrometric sensing apparatus 450 may further include a spacer 520c that is disposed between the first cover 410-1 and the PCB 510, and may provide a penetration part 520d between the light transmission region 410-1c and the PCB 510. The light receiving unit 460 and the light emitting unit 470 may be disposed in the penetration part 520d of the spacer 520c. External light may be transmitted to the light receiving unit 460 through the penetration part 520d. Likewise, light generated from the light emitting unit 470 may be discharged out through the penetration part 520d.

According to various embodiments, in FIG. 5C, the light transmission region 410-1c of the first cover 410-1 may include materials, has a shape or light transmittance characteristics that are similar to that of the first light transmission region 410-1a or second light transmission region 410-1b of FIG. 5A.

According to various embodiments, the spectrometric sensing apparatus 450 of FIG. 5C may further include a light transmitting member (e.g., a lens) (not shown) that is disposed in the penetration part 520d of the spacer 520c. Therefore, the light transmitting member may include the first light transmitting member 560 and the second light transmitting member 570 of FIG. 5A, or may be a single light transmitting member as shown in FIG. 5C.

According to various embodiments, the spectrometric sensing apparatus 450 may be provided as a single module (e.g., a System In Package (SIP)). FIGS. 5D and 5E illustrate the spectrometric sensing apparatus 450 according to an embodiment of the present disclosure. FIG. 5D is an exploded perspective view illustrating constituent elements of the spectrometric sensing apparatus 450, and FIG. 5E is a diagram viewing the spectrometric sensing apparatus 450 from the top of the first cover 591.

Referring to FIGS. 5D and 5E, the spectrometric sensing apparatus 450 of a package (or module) form may include a first cover (or a cap) 591, a second cover (or a second mold compound) 592, a third cover (or a third mold compound) 593, a light receiving unit 594, a light emitting unit 595, a first substrate 596 and a second substrate 597.

According to an embodiment, the spectrometric sensing apparatus 450 may be mounted in an electronic device (i.e., the electronic device 400 of FIG. 4), and be disposed between the first cover 410-1 of FIG. 4A and the PCB 510 of FIG. 5A. External light may be transmitted into the light receiving unit 594 through a transparent region (e.g., 410-1a of FIG. 5A or 410-1c of FIG. 5C) of the first cover 410-1. Light outputted from the light emitting unit 595 may be discharged through the transparent region (e.g., 410-1b of FIG. 5A or 410-1c of FIG. 5C) of the first cover 410-1.

The light emitting unit 595 may be mounted in the first substrate 596. Like the light emitting unit 470 of FIGS. 5A to 5C, the light emitting unit 595 may include at least one light source (e.g., LED) to output light of at least one wavelength band.

The light receiving unit 594 may be mounted in the first substrate 596. Like the light receiving unit 460 of FIGS. 5A to 5C, the light receiving unit 594 may convert light energy (or light signal) into electrical energy (or electrical signal). Light (e.g., ultraviolet rays, visible rays, infrared rays or the like) from the light emitting unit 595 may be irradiated onto an object external to the electronic device 400, and light scattered or reflected from the object may be transmitted into the light receiving unit 594. According to an embodiment, the light receiving unit 594 may include at least one region that may receive light of at least one wavelength band.

The second cover 592 may form a cover for the light receiving unit 594, and may be made of light transmissive materials. External light may pass through the second cover 592 and be transmitted to the light receiving unit 594. According to an embodiment, if the second cover 592 and the first substrate 596 are combined with each other, the light receiving unit 594 may be disposed in a space provided by the second cover 592. According to various embodiments, the second cover 592 may provide a function that is substantially similar to that of the first light transmitting member 560 of FIG. 5A.

The third cover 593 may form a cover for the light emitting unit 595, and may be made of light transmissive materials. Light outputted from the light emitting unit 595 may pass through the third cover 593 and be discharged. According to an embodiment, if the third cover 593 and the first substrate 596 are combined with each other, the light emitting unit 595 may be disposed in a space provided by the third cover 593. According to various embodiments, the third cover 593 may provide a function that is substantially similar to that of the second light transmitting member 570 of FIG. 5A.

The first substrate 596 may be disposed between the light receiving unit 594/light emitting unit 595 and the second substrate 597. The first substrate 596 may be combined to the second substrate 597, and include wirings (not shown) for electrical connection between the light receiving unit 594/light emitting unit 595 and the second substrate 597. According to an embodiment, the light receiving unit 594 and the light emitting unit 595 may be connected to one or more pads (not shown) of the first substrate 596 using soldering.

According to an embodiment, the light receiving unit 594 and the light emitting unit 595 may be disposed adjacent to each other, and the first substrate 596 may be large enough to permit an array (i.e. a plurality) of the light receiving unit 594 and the light emitting unit 595. For example, as illustrated, the first substrate 596 may be rectangular, and the light receiving unit 594 and the light emitting unit 595 may be arrayed lengthwise on the first substrate 596.

The second substrate 597 may be combined with a PCB (e.g., PCB 510 of FIG. 5A) of an electronic device (e.g. electronic device 400 of FIG. 4A). If the second substrate 597 is combined with the PCB 510, the second substrate 597 may be disposed between the first substrate 596 and the PCB 510, and the second substrate 597 may relay connection wiring between the first substrate 596 and the PCB 510. According to an embodiment, the second substrate 597 may be an interposer. For example, the second substrate 597 may include various non-illustrated components (e.g., passive components), etc. for a spectrometric sensing function of the spectrometric sensing apparatus 450.

The first cover 591 may form a container (e.g., a rectangular container) that is roughly convex in the −Z direction as shown in FIG. 5D. If the first cover 591 and the second substrate 597 are combined with each other, it may provide a space for housing the second cover 592, the third cover 593, the light receiving unit 594, the light emitting unit 595 and the first substrate 596. According to an embodiment, the first cover 591 may include a first through-hole 5911 that is provided in a position aligned to the light receiving unit 594. If the spectrometric sensing apparatus 450 is mounted in the electronic device (400 of FIG. 4A), the first through-hole 5911 may be aligned to a transparent region (e.g., 410-1a of FIG. 5A or 410-1c of FIG. 5C) of the first cover 410-1. External light may be transmitted to the light receiving unit 594 through the first through-hole 5911. According to an embodiment, the first cover 591 may include a second through-hole 5912 that is provided in a position aligned to the light emitting unit 595. If the spectrometric sensing apparatus 450 is mounted in the electronic device (400 of FIG. 4A), the second through-hole 5912 may be aligned to the transparent region (410-1b of FIG. 5A or 410-1c of FIG. 5C) of the first cover 410-1. Light generated from the light emitting unit 595 may be discharged through the second through-hole 5912.

FIGS. 6A, 6B, 6C, 7A, 7B, 7C, 7D and 7E are diagrams showing arrangement structures of pluralities of light detectors in light receiving units according to various embodiments of the present disclosure.

Figure 6A:
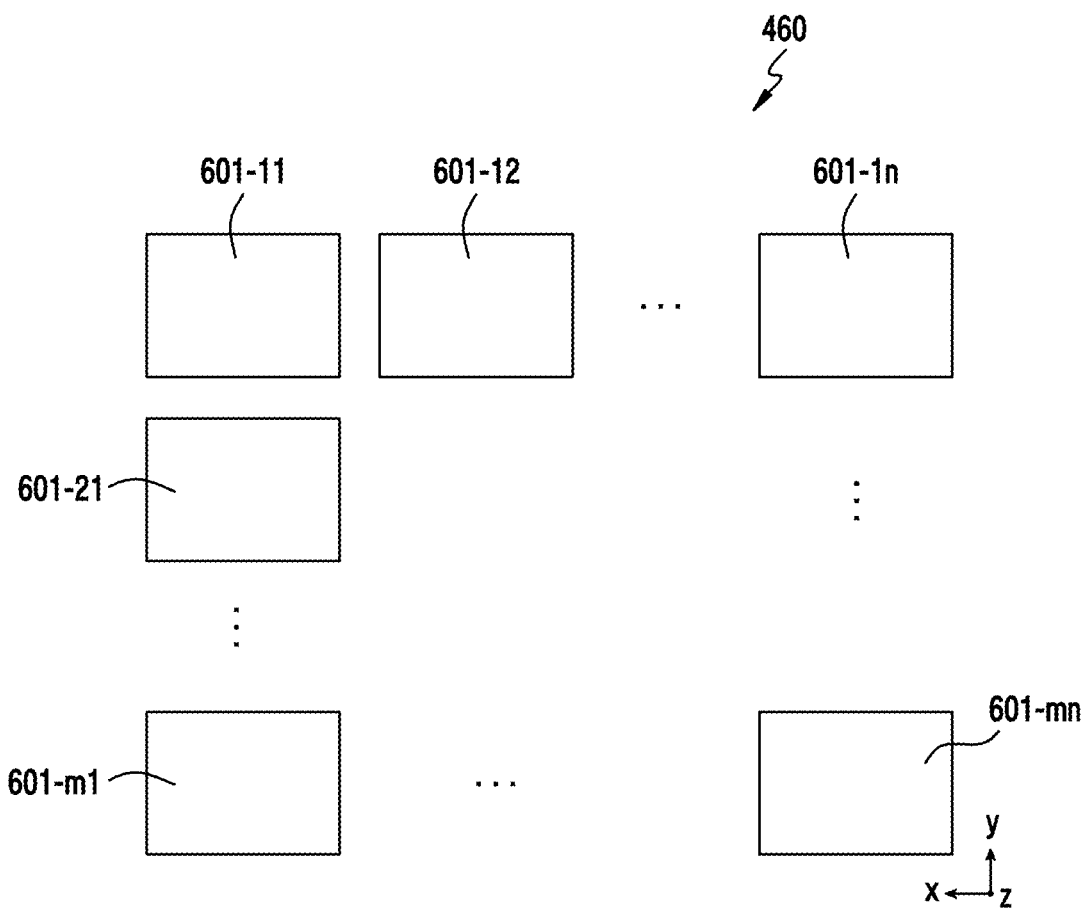
FIG. 6A, FIG. 6B, FIG. 6C, FIG. 7A, FIG. 7B, FIG. 7C, FIG. 7D and FIG. 7E are diagrams showing arrangement structures of pluralities of light detectors in light receiving units according to various embodiments of the present disclosure.

Referring to FIG. 6A, a light receiving unit (460 of FIG. 5A, 5B or 5C, or 594 of FIG. 5D or 5E) according to an embodiment may include one or more light detectors 601-$ij$, where 1≤i≤m and 1≤j≤n, that are arrayed in an x-axis direction (e.g., the direction going from the edge 410-13 of FIG. 4A to the edge 410-14) and/or a y-axis direction (e.g., the direction going from the edge 410-11 of FIG. 4A to the edge 410-12). According to various embodiments, at least some of the one or more light detectors 601-$ij$ may detect light signals of mutually different wavelength bands.

Figure 6B:
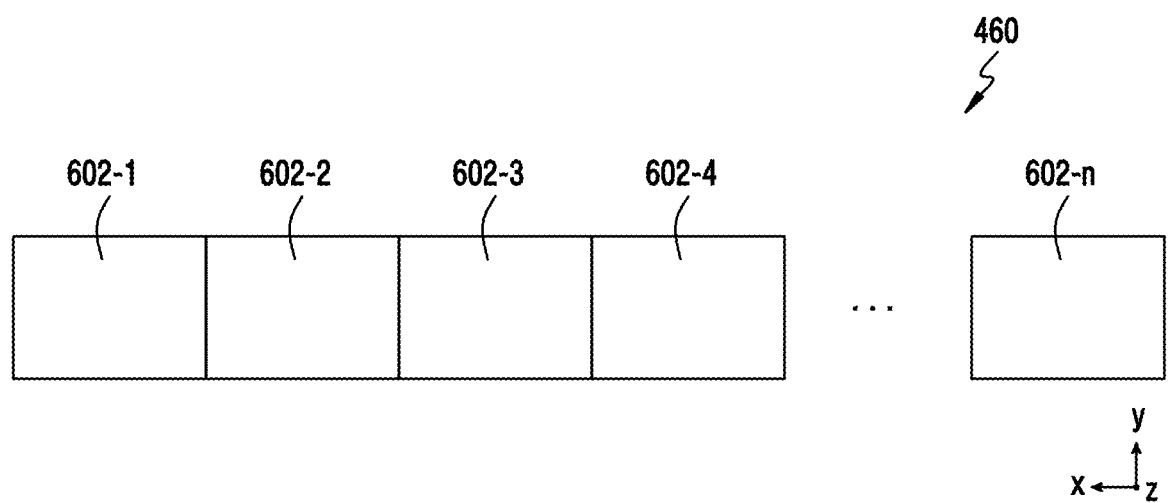

Referring to FIG. 6B, the light receiving unit 460 or 594 according to an embodiment may include one or more light detectors 602-$i$, where 1≤i≤n, that are arrayed in an x-axis direction. According to various embodiments, at least some of the one or more light detectors 602-$i$ may detect light signals of mutually different wavelength bands.

Figure 6C:
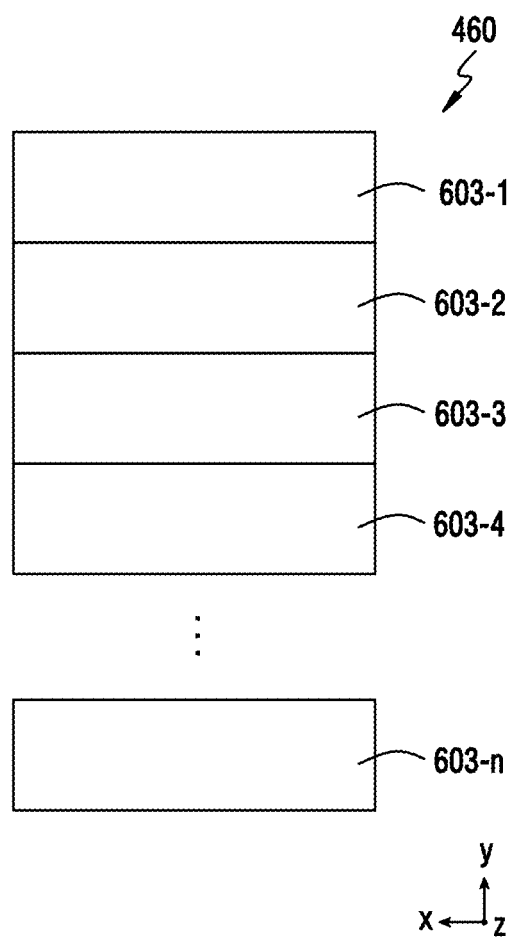

Referring to FIG. 6C, the light receiving unit 460 or 594 according to an embodiment may include one or more light detectors 603-$i$, where 1≤i≤n, that are arrayed in a y-axis direction. According to various embodiments, at least some of the one or more light detectors 603-$i$ may detect light signals of mutually different wavelength bands.

Figure 7A:
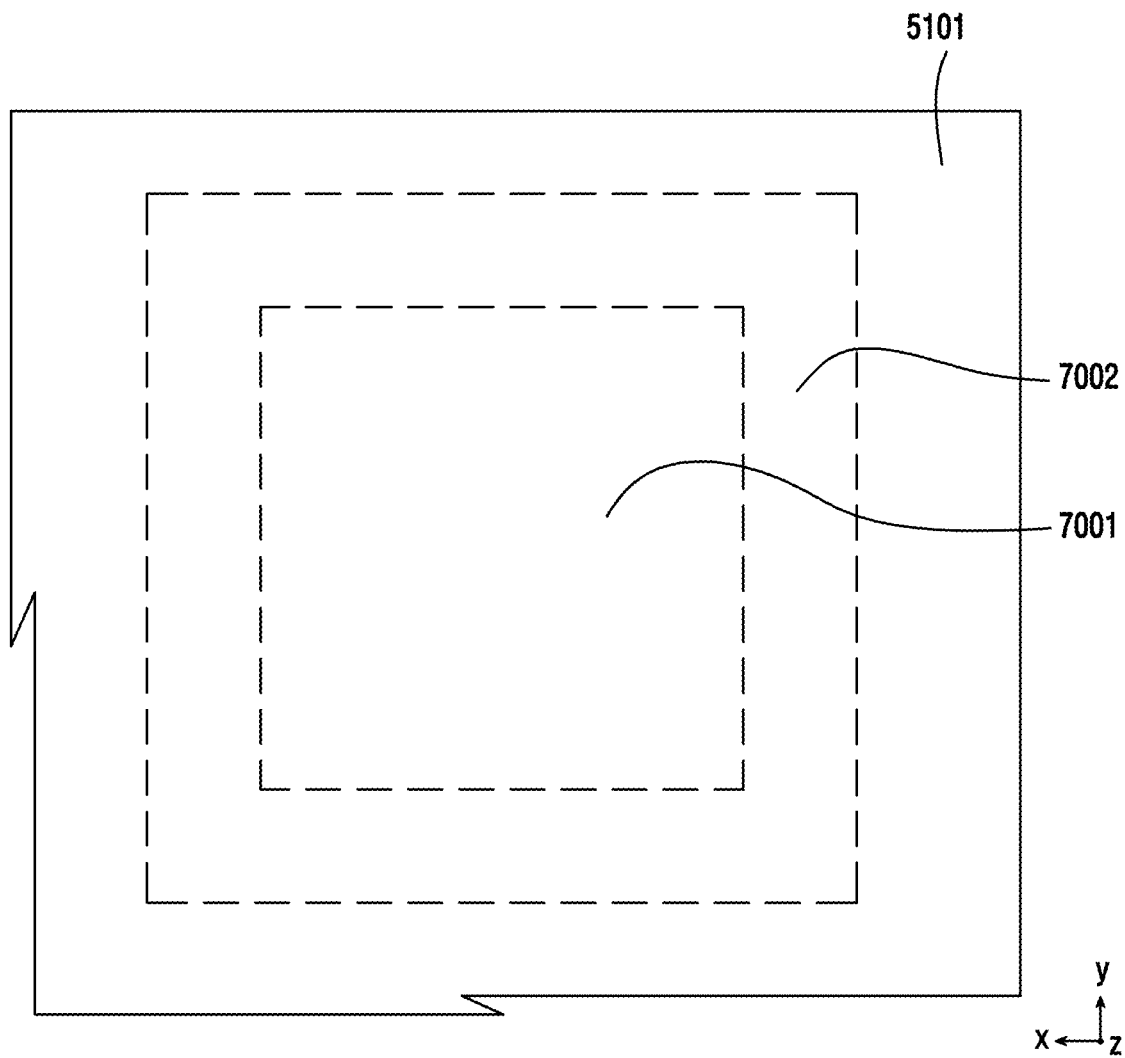

Referring to FIG. 7A, according to an embodiment, the first surface 5101 of the PCB (e.g., 510 of FIG. 5A) may include a first region 7001 and a second region 7002. The second region 7002 may surround the first region 7001. For example, as illustrated, the first region 7001 may be roughly rectangular, and the second region 7002 may have a rectangular ring shape. According to various embodiments, the first region 7001 may be various such as a circular shape, etc., without being limited to the rectangular shape.

According to an embodiment, at least one light detector of a light receiving unit (e.g., 460 of FIG. 5B or 594 of FIG. 5D) may be disposed in at least one of the first region 7001 and the second region 7002 of the first surface 5101 of the PCB.

Figure 7B:
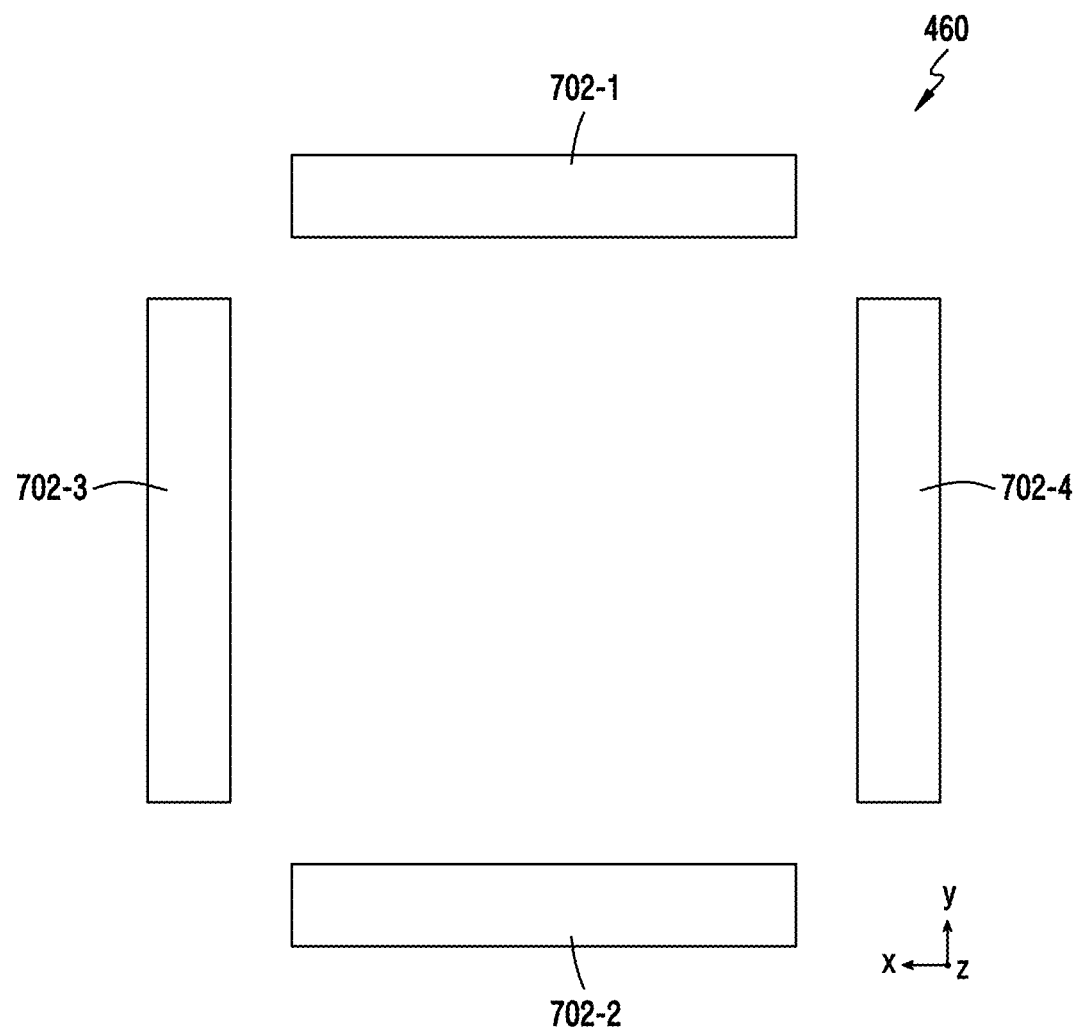

Referring to FIG. 7B, the light receiving unit 460 according to an embodiment may include a first light detector 702-1, a second light detector 702-2, a third light detector 702-3 and a fourth light detector 702-4 that are disposed in the second region (7002 of FIG. 7A) of the PCB (e.g., 510 of FIG. 5A). For example, as illustrated in FIG. 7A, the second region 7002 may have a roughly rectangular ring shape that includes four straight side regions. The first light detector 702-1, the second light detector 702-2, the third light detector 702-3 and the fourth light detector 702-4 may be disposed in each of the four straight side regions of the second region 7002, respectively. According to various embodiments, at least some of the first light detector 702-1, the second light detector 702-2, the third light detector 702-3 and the fourth light detector 702-4 may detect light signals of mutually different wavelength bands.

Figure 7C:
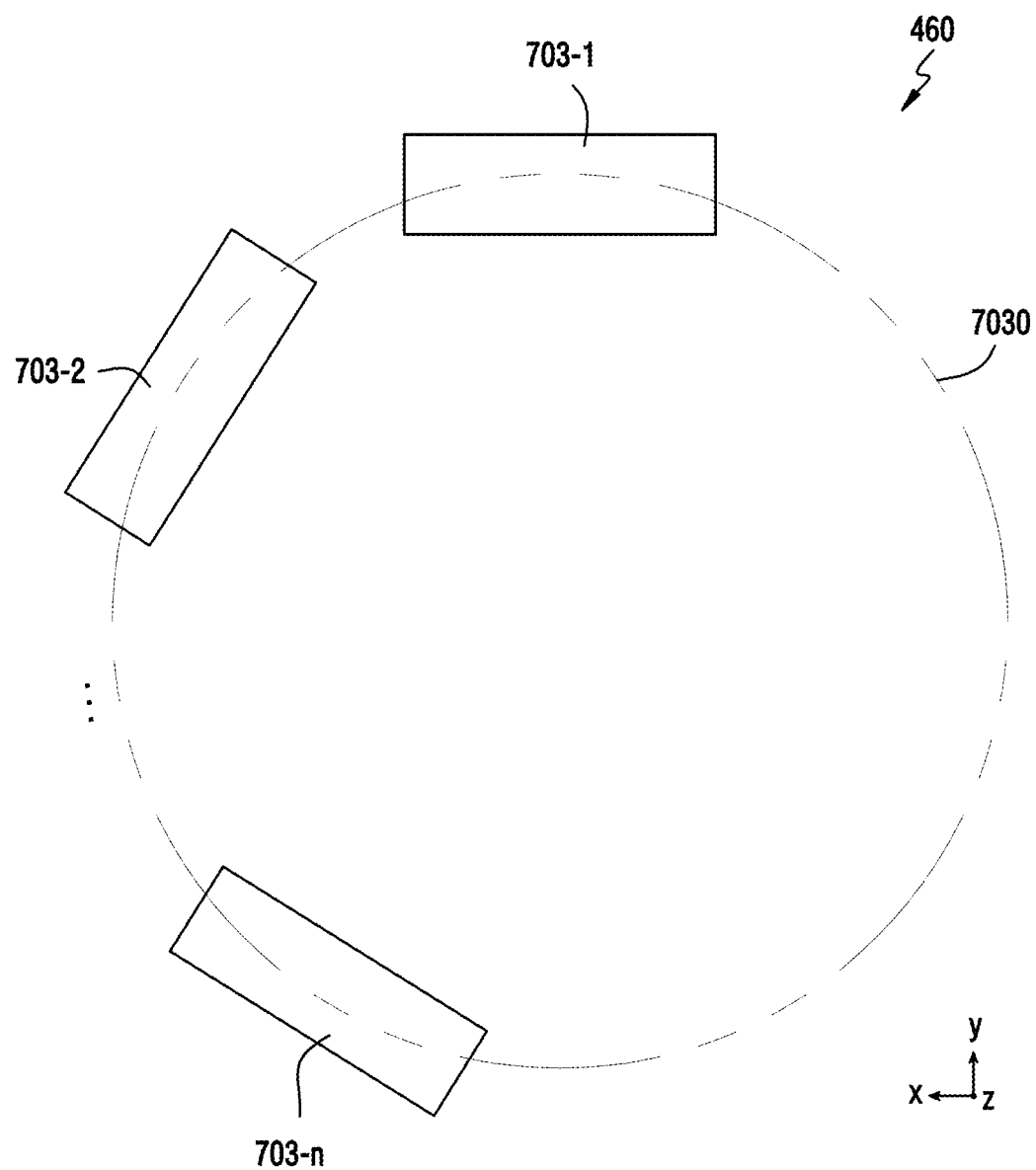

Referring to FIG. 7C, the light receiving unit 460 according to an embodiment may include a plurality of light detectors 703-$i$, where 1≤$i$≤n, that are disposed along the circumference of an imaginary circle 7030. For example, the second region (7002 of FIG. 7A) of the PCB 510 may have a circular ring shape (not shown). The plurality of light detectors 703-$n$ may be disposed in the second region 7002 along the circular ring. According to various embodiments, at least some of the plurality of light detectors 703-$n$ may detect light signals of mutually different wavelength bands.

Figure 7D:
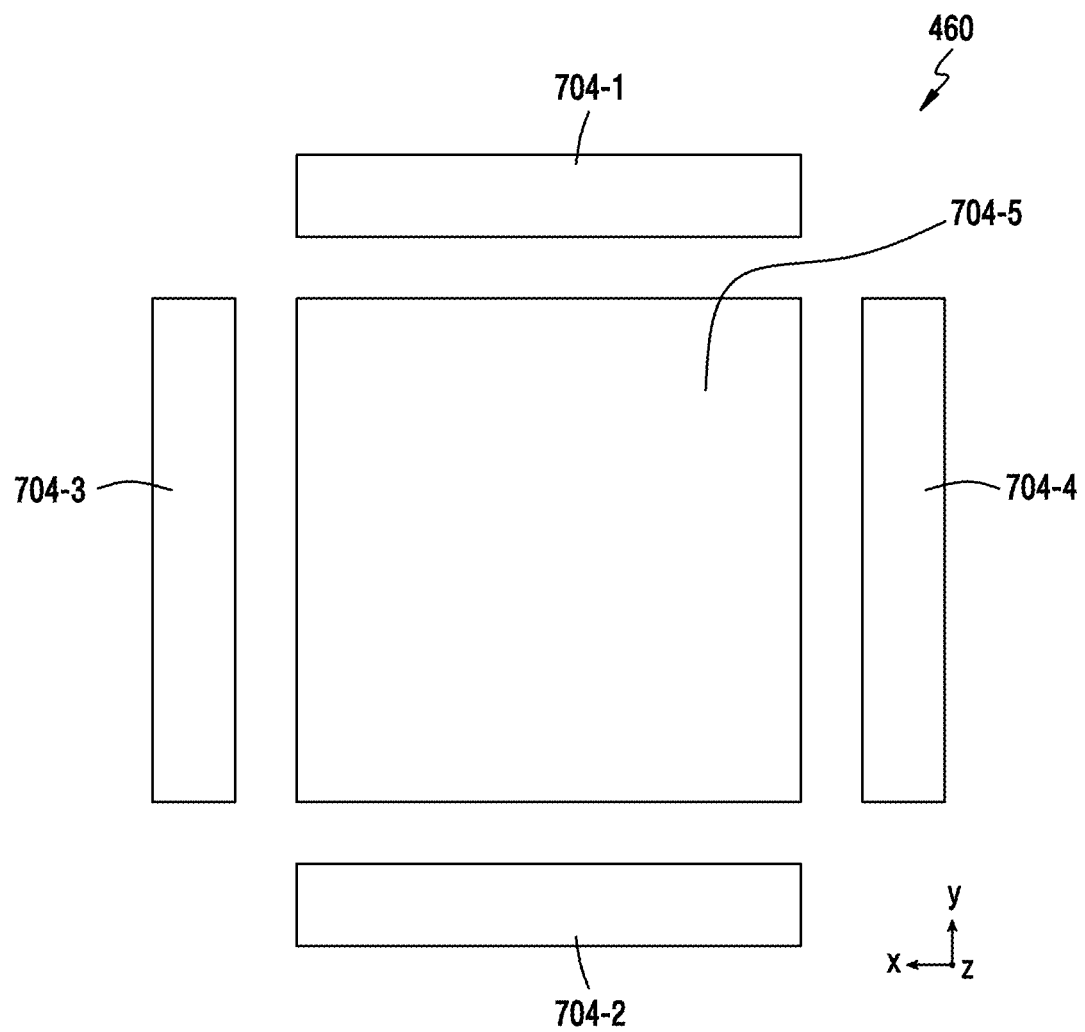

Referring to FIG. 7D, the light receiving unit 460 according to an embodiment may include a first light detector 704-1, a second light detector 704-2, a third light detector 704-3 and a fourth light detector 704-4 that are disposed in the second region (7002 of FIG. 7A) of the PCB 510. For example, the first light detector 704-1, the second light detector 704-2, the third light detector 704-3 and the fourth light detector 704-4 may be disposed similarly with the first light detector 702-1, the second light detector 702-2, the third light detector 702-3 and the fourth light detector 702-4 shown in FIG. 7B. However unlike the light detectors shown in FIG. 7B, the light receiving unit 460 in FIG. 7D may include a fifth light detector 704-5 that is disposed in the first region (7001 of FIG. 7A) of the PCB 510. According to various embodiments, at least some of the first light detector 704-1, the second light detector 704-2, the third light detector 704-3, the fourth light detector 704-4 and the fifth light detector 704-5 may detect light signals of mutually different wavelength bands. According to various embodiments, the fifth light detector 704-5 may include a plurality of light detectors not illustrated that may detect light signals of mutually different wavelength bands.

Figure 7E:
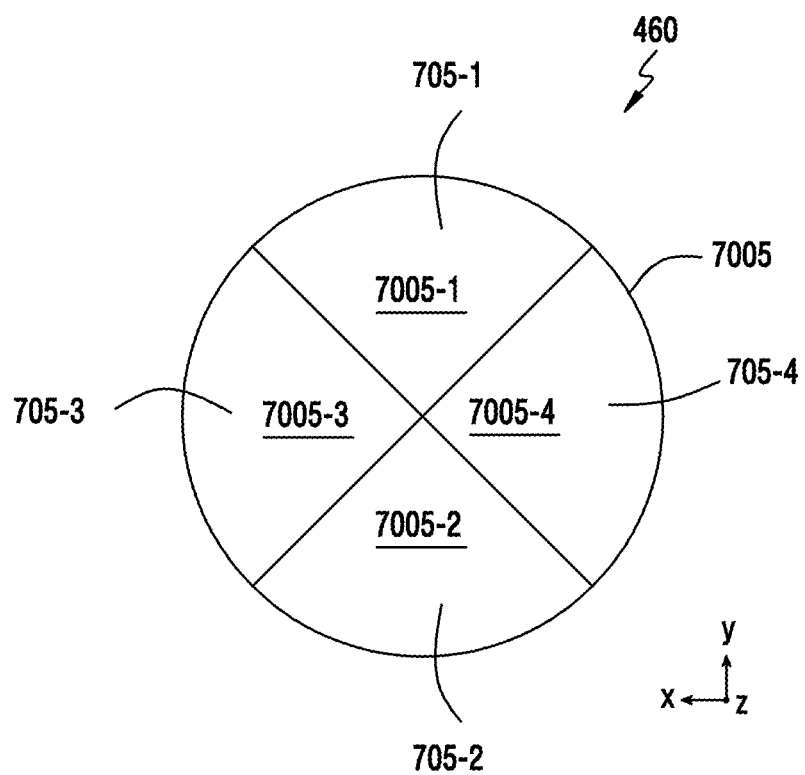

Referring to FIG. 7E, according to an embodiment, the first region 7005 (e.g., 7001 of FIG. 7A) of the PCB 510 may be divided into a plurality of regions, and the light receiving unit 460 may include a plurality of light detectors that are disposed in the plurality of regions respectively. For example, the first region 7005 shown may have a roughly circular shape, and may be divided into four regions 7005-1, 7005-2, 7005-3 and 7005-4. The light receiving unit 460 may include a first light detector 705-1, a second light detector 705-2, a third light detector 705-3 and a fourth light detector 705-4 that are disposed in the four regions 7005-1, 7005-2, 7005-3 and 7005-4 respectively. According to various embodiments, at least some of the first light detector 705-1, the second light detector 705-2, the third light detector 705-3 and the fourth light detector 705-4 may detect light signals of mutually different wavelength bands.

Figure 8:
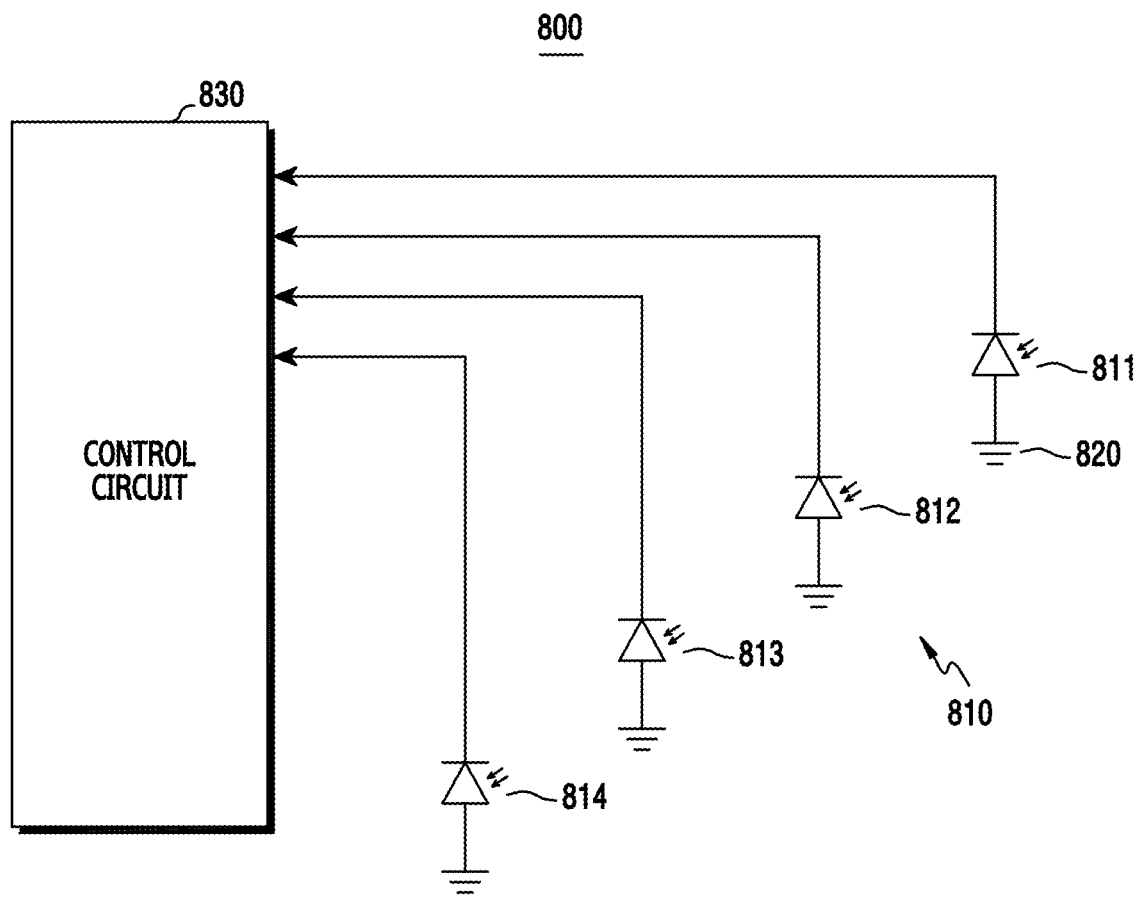
FIG. 8 is a light receiving circuit diagram of a spectrometric sensing apparatus according to an embodiment of the present disclosure.
Figure 9A:
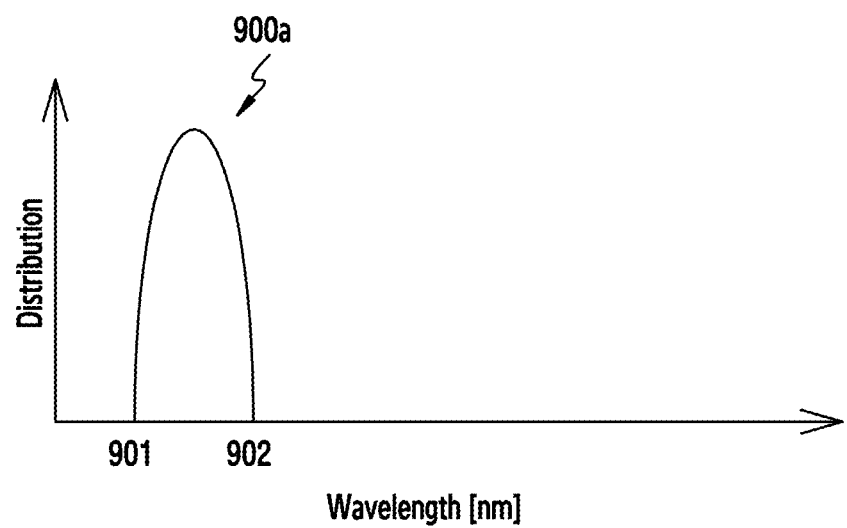
FIG. 9A, FIG. 9B, FIG. 9C and FIG. 9D are diagrams showing the distribution of wavelength bands that various light receiving units may detect in a spectrometric sensing apparatus according to various embodiments of the present disclosure.
Figure 9B:
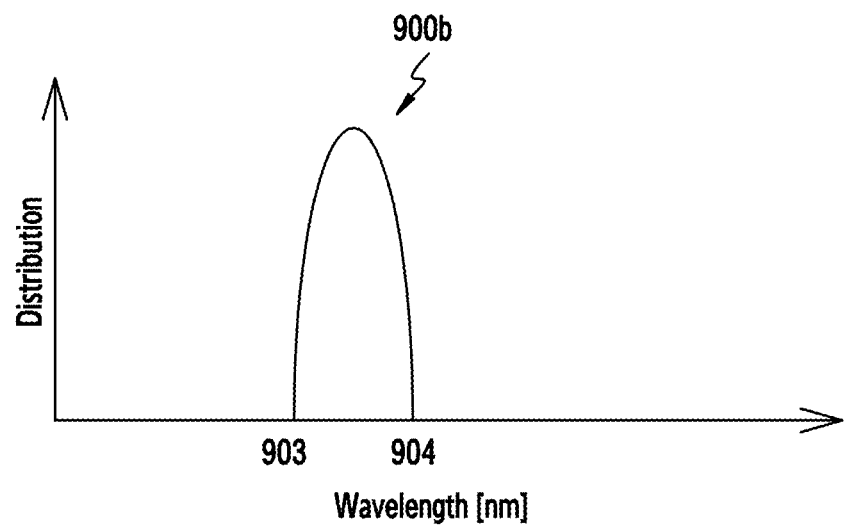
Figure 9C:
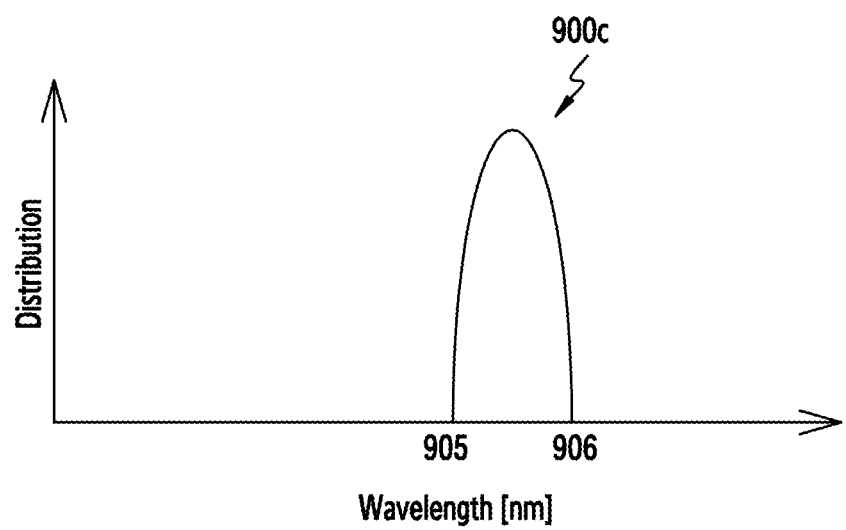
Figure 9D:
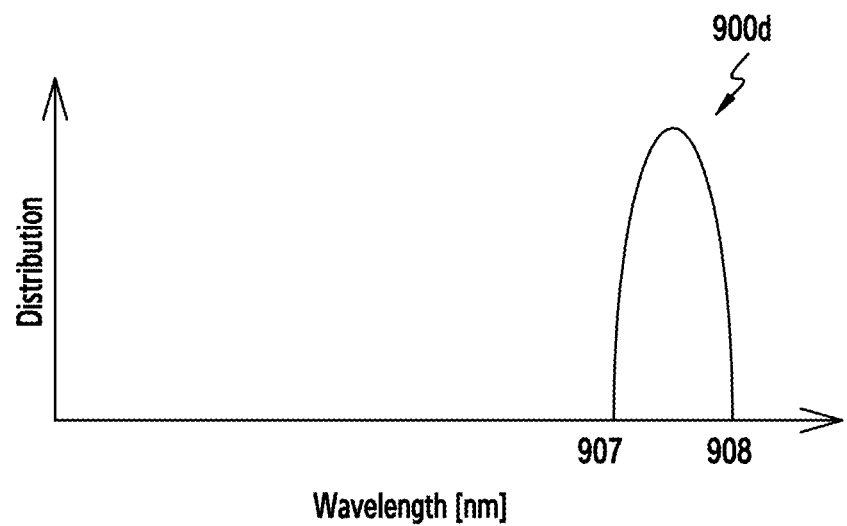
Figure 10A:
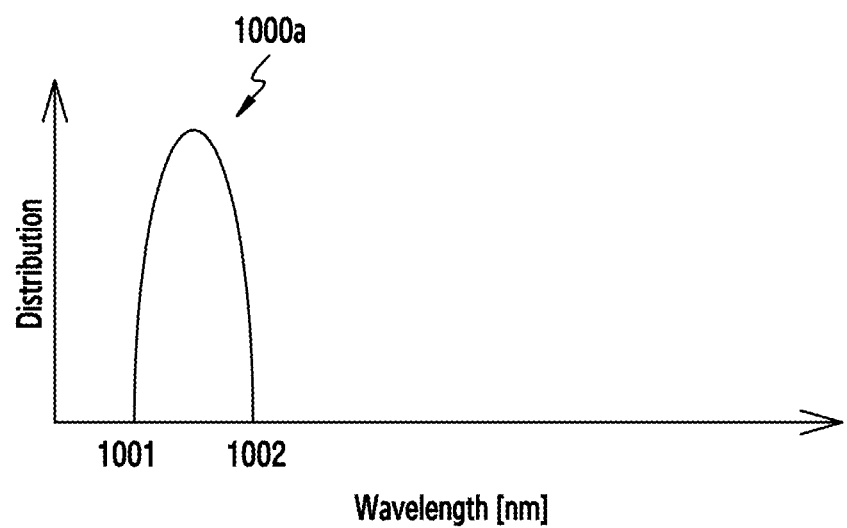
FIG. 10A, FIG. 10B, FIG. 10C and FIG. 10D are diagrams showing the distribution of wavelength bands that various light receiving unit may detect in a spectrometric sensing apparatus according to various embodiments of the present disclosure.
Figure 10B:
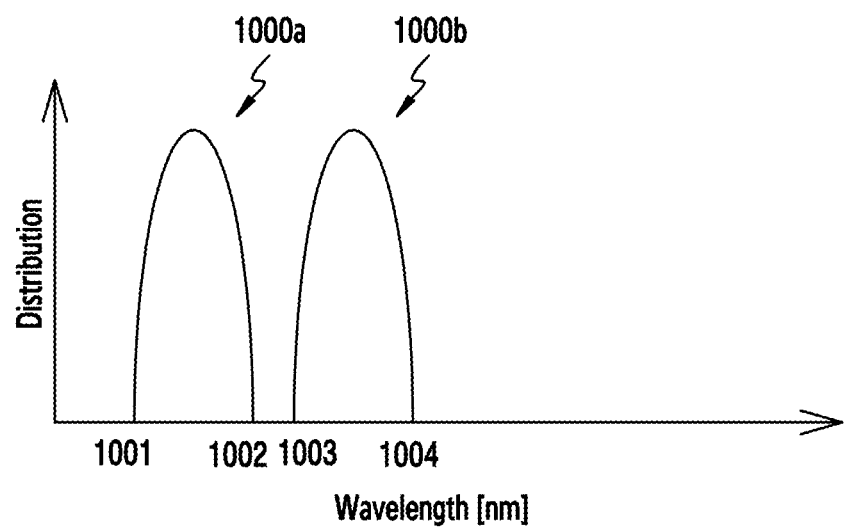
Figure 10C:
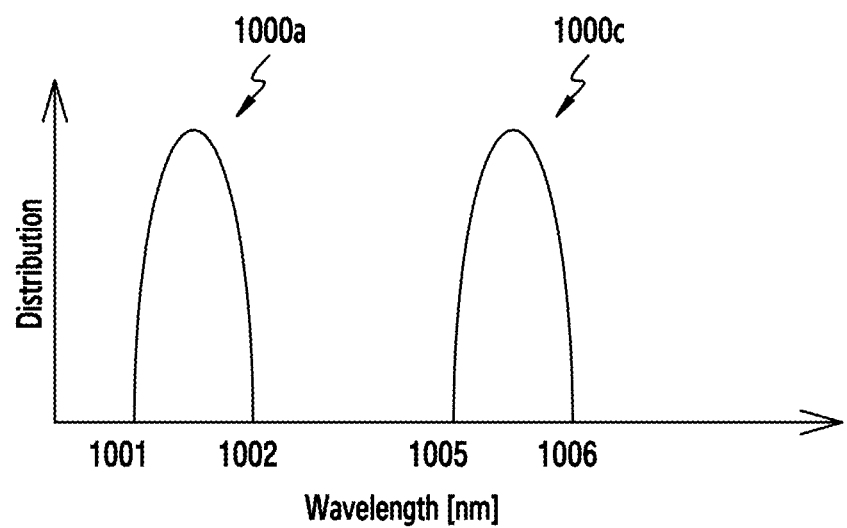
Figure 10D:
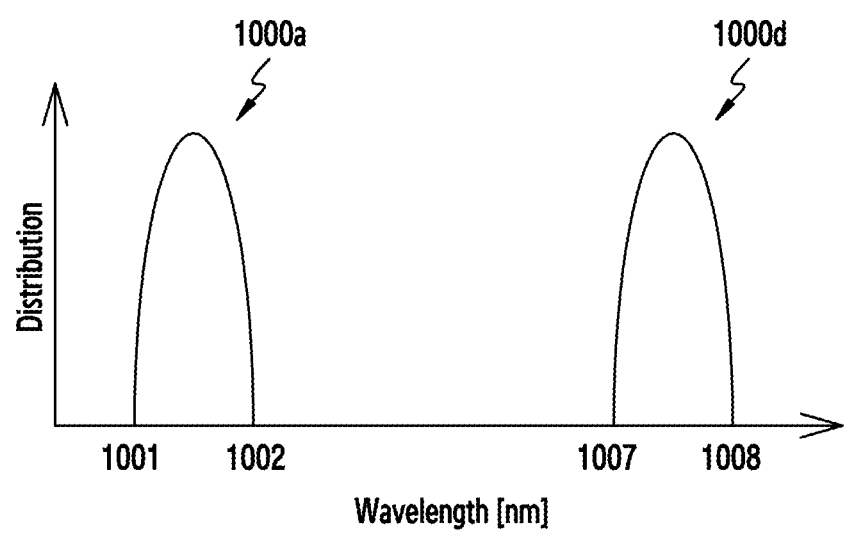
Figure 11A:
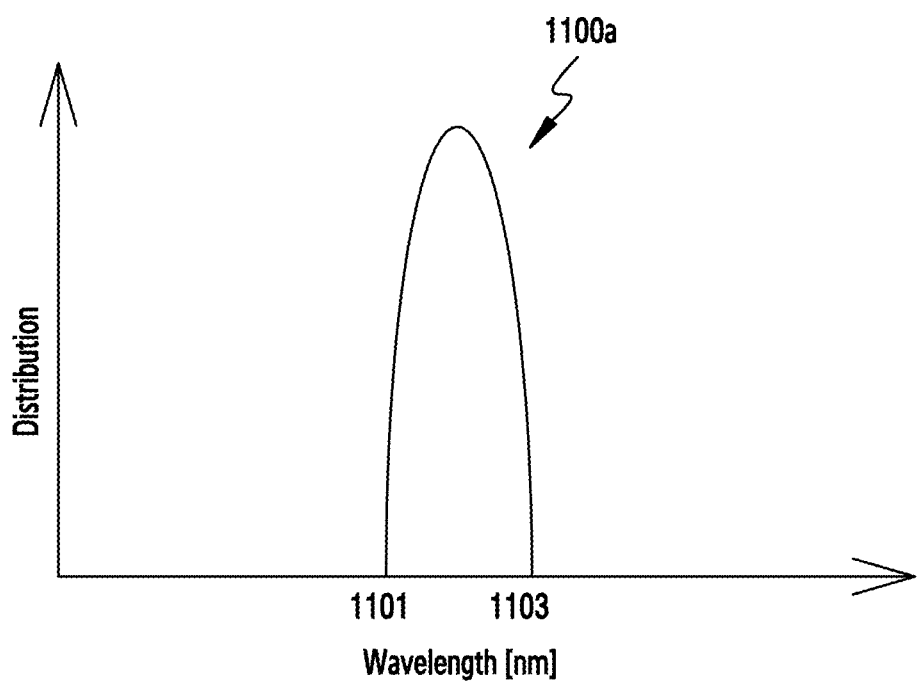
FIG. 11A and FIG. 11B are diagrams showing the distribution of wavelength bands that various light receiving units may detect in a spectrometric sensing apparatus according to various embodiments of the present disclosure.
Figure 11B:
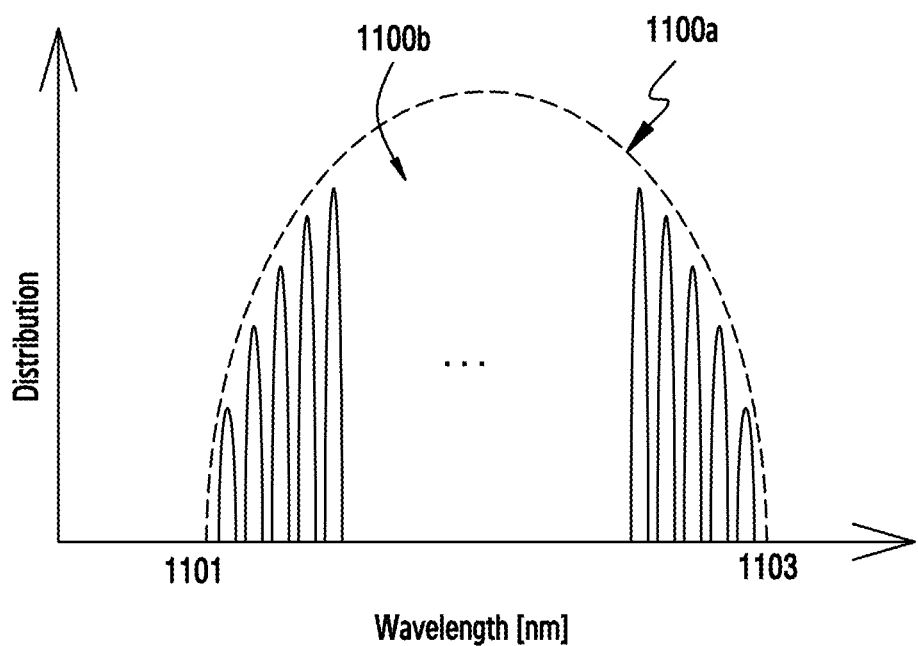

FIG. 8 is a light receiving circuit diagram of a spectrometric sensing apparatus according to an embodiment of the present disclosure. FIGS. 9A, 9B, 9C and 9D are diagrams showing the distribution of wavelength bands that light receiving units may detect in a spectrometric sensing apparatus according to various embodiments of the present disclosure. FIGS. 10A, 10B, 10C and 10D are diagrams showing the distribution of wavelength bands that light receiving units may detect in a spectrometric sensing apparatus according to various embodiments of the present disclosure. FIGS. 11A and 11B are diagrams showing the distribution of wavelength bands that light receiving units may detect in a spectrometric sensing apparatus according to various embodiments of the present disclosure.

Referring to FIG. 8, a light receiving circuit 800 may include a light receiving unit 810 and a control circuit 830. According to an embodiment, the light receiving unit 810 may include a plurality of light detectors. For example, as illustrated, the light receiving unit 810 may include a first light detector 811, a second light detector 812, a third light detector 813 and a fourth light detector 814. According to various embodiments, though not illustrated, the light receiving unit 810 may further include more light detectors as well.

According to various embodiments, the plurality of light detectors 811, 812, 813 and 814 of the light receiving unit 810 may be mounted in a PCB (e.g., the PCB 510 of FIG. 5A) in the form of one arrangement of FIG. 6A, 6B, 6C, 7A, 7B, 7C, 7D or 7E.

According to an embodiment, one terminal of the light receiving unit 810 may be electrically connected to a ground member 820 (e.g., the ground of the PCB 510 of FIG. 5A) of an electronic device (e.g., the electronic device 101 of FIG. 1, the electronic device 201 of FIG. 2 or the electronic device 400 of FIG. 4A). The other terminal of the light receiving unit 810 may be electrically connected to the control circuit 830. The light receiving unit 810 may detect a light signal, and convert the detected light signal into an electrical signal, and forward the converted electrical signal to the control circuit 830. According to various embodiments, the light detectors 811, 812, 813 and 814 of the light receiving unit 810 may be photo diodes.

According to an embodiment, the first to fourth light detectors 811, 812, 813 and 814 of the light receiving unit 810 may detect light signals of mutually different wavelength bands, respectively. For example, FIGS. 9A, 9B, 9C and 9D illustrate the distribution of wavelength bands that the first to fourth light detectors 811, 812, 813 and 814 may detect respectively. Referring to FIG. 9A, the first light detector 811 may detect a light signal of a first wavelength band 900$a$ that ranges from a first wavelength 901 to a second wavelength 902. Referring to FIG. 9B, the second light detector 812 may detect a light signal of a second wavelength band 900$b$ that ranges from a third wavelength 903 to a fourth wavelength 904. Referring to FIG. 9C, the third light detector 813 may detect a light signal of a third wavelength band 900$c$ that ranges from a fifth wavelength 905 to a sixth wavelength 906. Referring to FIG. 9D, the fourth light detector 814 may detect a light signal of a fourth wavelength band 900$d$ that ranges from a seventh wavelength 907 to an eighth wavelength 908. The first wavelength band 900$a$, the second wavelength band 900$b$, the third wavelength band 900$c$ and the fourth wavelength band 900$d$ may be mutually different.

The control circuit 830 may select and activate at least some of the plurality of light detectors 811, 812, 813 and 814 of the light receiving unit 810 in accordance with a selection of at least one detection mode.

In embodiments of FIGS. 9A, 9B, 9C and 9D, when a single detection mode is selected, the control circuit 830 may select and activate one of the plurality of light detectors 811, 812, 813 and 814 of the light receiving unit 810. For example, when a first detection mode is selected, the control circuit 830 may select and activate the first light detector 811, and the first light detector 811 may detect a first light signal of the first wavelength band 900a. When a second detection mode is selected, the control circuit 830 may select and activate the second light detector 812, and the second light detector 812 may detect a second light signal of the second wavelength band 900b. When a third detection mode is selected, the control circuit 830 may select and activate the third light detector 813, and the third light detector 813 may detect a third light signal of the third wavelength band 900c. When a fourth detection mode is selected, the control circuit 830 may select and activate the fourth light detector 814, and the fourth light detector 814 may detect a fourth light signal of the fourth wavelength band 900d. According to various embodiments, when the proximity detection mode or the gesture detection mode is selected, the control circuit 830 may select and activate one light detector that is designated to the proximity detection mode or the gesture detection mode among the plurality of light detectors 811, 812, 813 and 814. The activated one light detector may detect a light signal of a proximity detecting or gesture detecting wavelength band. According to various embodiments, when the biometric detection mode is selected, the control circuit 830 may select and activate at least one light detector that is designated to the biometric detection mode. The activated at least one light detector may detect a light signal of a biometric detecting wavelength band.

According to various embodiments, in embodiments of FIGS. 9A, 9B, 9C and 9D, when a single detection mode is selected, the control circuit 830 may select and activate many of the plurality of light detectors 811, 812, 813 and 814 as well. The activated many of the light detectors may detect light signals of corresponding wavelength bands. For example, a skin moisture detection mode may be designed to detect a light signal at a wavelength band including the maximum sensitivity wavelength of 880 nm, and/or a wavelength band including the maximum sensitivity wavelength of 970 nm. A skin melanin detection mode may be designed to detect a light signal at a wavelength band including the maximum sensitivity wavelength of 660 nm, and/or a wavelength band including the maximum sensitivity wavelength of 880 nm. An erythema detection mode may be designed to detect a light signal at a wavelength band including the maximum sensitivity wavelength of 568 nm, and/or a wavelength band including the maximum sensitivity wavelength of 880 nm.

In embodiments of FIGS. 9A, 9B, 9C and 9D, when a multi detection mode is selected, the control circuit 830 may select and activate many of the plurality of light detectors 811, 812, 813 and 814 of the light receiving unit 810. For example, when a first detection mode and a second detection mode are selected, the control circuit 830 may select and activate the first light detector 811 and the second light detector 812. The first light detector 811 may detect a first light signal of the first wavelength band 900a, and the second light detector 812 may detect a second light signal of the second wavelength band 900b. According to various embodiments, when the proximity detection mode and the biometric detection mode are selected, the control circuit 830 may select and activate one light detector that is designated to the proximity detection mode and another light detector that is designated to the biometric detection mode among the plurality of light detectors 811, 812, 813 and 814. The activated light detectors may detect a light signal of the proximity detecting wavelength band and a light signal of the biometric detecting wavelength band.

According to an embodiment, the first to fourth light detectors 811, 812, 813 and 814 of the light receiving unit 810 may be configured to detect at least one light signal of commonly similar or identical at least one wavelength. For example, wavelength bands in which the first to fourth light detectors 811, 812, 813 and 814 of the light receiving unit 810 detect at least one light signal may be at least overlapped each other. For example, FIGS. 10A, 10B, 10C and 10D illustrate the distribution of wavelength bands that the first to fourth light detectors 811, 812, 813 and 814 may detect respectively. Referring to FIG. 10A, the first light detector 811 may detect a first light signal of a first wavelength band 1000a that ranges from a first wavelength 1001 to a second wavelength 1002. Referring to FIG. 10B, the second light detector 812 may detect not only the first light signal of the first wavelength band 1000a, but also a second light signal of a second wavelength band 1000b that ranges from a third wavelength 1003 to a fourth wavelength 1004. Referring to FIG. 10C, the third light detector 813 may detect not only the first light signal of the first wavelength band 1000a, but also a third light signal of a third wavelength band 1000c that ranges from a fifth wavelength 1005 to a sixth wavelength 1006. Referring to FIG. 10D, the fourth light detector 814 may detect not only the first light signal of the first wavelength band 1000a, but also a fourth light signal of a fourth wavelength band 1000d that ranges from a seventh wavelength 1007 to an eighth wavelength 1008. The first wavelength band 1000a, the second wavelength band 1000b, the third wavelength band 1000c and the fourth wavelength band 1000d may be mutually different.

In embodiments of FIGS. 10A, 10B, 10C and 10D, when a single detection mode is selected, the control circuit 830 may select and activate at least one of the plurality of light detectors 811, 812, 813 and 814 of the light receiving unit 810.

For example, when a first detection mode is selected, the control circuit 830 may select and activate at least one of the plurality of light detectors 811, 812, 813 and 814. The at least one light detector may detect the first light signal of the first wavelength 1000a.

For example, when a second detection mode is selected, the control circuit 830 may select and activate the second light detector 812. The second light detector 812 may detect the first light signal of the first wavelength band 1000a and/or the second light signal of the second wavelength band 1000b. In the second detection mode, the second light detector 812 may forward a second electrical signal, according to the detected second light signal, to the control circuit 830. The control circuit 830 may process the second electrical signal as valid in accordance with the second detection mode. According to various embodiments, in the second detection mode, the second light detector 812 may forward the first electrical signal, according to the detected first light signal to the control circuit 830. In the second detection mode, the control circuit 830 may process the first electrical signal as invalid.

For example, when a third detection mode is selected, the control circuit 830 may select and activate the third light detector 813. The third light detector 813 may detect the first light signal of the first wavelength band 1000a and/or the third light signal of the third wavelength band 1000c. In the third detection mode, the third light detector 813 may forward a third electrical signal, according to the detected third light signal, to the control circuit 830. The control circuit 830 may process the third electrical signal as valid in accordance with the third detection mode. According to various embodiments, in the third detection mode, the third light detector 813 may forward the first electrical signal, according to the detected first light signal, to the control circuit 830. In the third detection mode, the control circuit 830 may process the first electrical signal as invalid.

For example, when a fourth detection mode is selected, the control circuit 830 may select and activate the fourth light detector 814. The fourth light detector 814 may detect the first light signal of the first wavelength band 1000a and/or the fourth light signal of the fourth wavelength band 1000d. In the fourth detection mode, the fourth light detector 814 may forward a fourth electrical signal, according to the detected fourth light signal, to the control circuit 830. The control circuit 830 may process the fourth electrical signal as valid in accordance with the fourth detection mode. According to various embodiments, in the fourth detection mode, the fourth light detector 814 may forward the first electrical signal, according to the detected first light signal, to the control circuit 830. In the fourth detection mode, the control circuit 830 may process the first electrical signal as invalid.

According to various embodiments, in embodiments of FIGS. 10A, 10B, 10C and 10D, when a single detection mode is selected, the control circuit 830 may select and activate many of the plurality of light detectors 811, 812, 813 and 814 as well. The activated many of the light detectors may detect light signals of corresponding wavelength bands. For example, a skin moisture detection mode may be designed to detect a light signal at a wavelength band including the maximum sensitivity wavelength of 880 nm, and/or a wavelength band including the maximum sensitivity wavelength of 970 nm. A skin melanin detection mode may be designed to detect a light signal at a wavelength band including the maximum sensitivity wavelength of 660 nm, and/or a wavelength band including the maximum sensitivity wavelength of 880 nm. An erythema detection mode may be designed to detect a light signal at a wavelength band including the maximum sensitivity wavelength of 568 nm, and/or a wavelength band including the maximum sensitivity wavelength of 880 nm.

In embodiments of FIGS. 10A, 10B, 10C and 10D, when a multi detection mode is selected, the control circuit 830 may select and activate many of the plurality of light detectors 811, 812, 813 and 814 of the light receiving unit 810.

For example, when the first detection mode and the second detection mode are selected, the control circuit 830 may select and activate the first light detector 811 and the second light detector 812. The first light detector 811 may detect the light signal of the first wavelength band 1000a, and the second light detector 812 may detect the light signal of the first wavelength band 1000a and/or the light signal of the second wavelength band 1000b.

For another example, when the second detection mode and the third detection mode are selected, the control circuit 830 may select and activate the second light detector 812 and the third light detector 813. The second light detector 812 may detect the first light signal of the first wavelength band 1000a and/or the second light signal of the second wavelength band 1000b, and the third light detector 813 may detect the first light signal of the first wavelength band 1000a and/or the third light signal of the third wavelength band 1000c. In the second detection mode, the second light detector 812 may forward a second electrical signal, according to the detected second light signal, to the control circuit 830. The control circuit 830 may process the second electrical signal as valid in accordance with the second detection mode. According to various embodiments, in the second detection mode, the second light detector 812 may forward a first electrical signal, according to the detected first light signal, to the control circuit 830. In the second detection mode, the control circuit 830 may process the first electrical signal as invalid. In the third detection mode, the third light detector 813 may forward a third electrical signal, according to the detected third light signal, to the control circuit 830. The control circuit 830 may process the third electrical signal as valid in accordance with the third detection mode. According to various embodiments, in the third detection mode, the third light detector 813 may forward the first electrical signal, according to the detected first light signal, to the control circuit 830. In the third detection mode, the control circuit 830 may process the first electrical signal as invalid.

In embodiments of FIGS. 11A and 11B, the light receiving unit 810 may be designed to detect a light signal of the wavelength band 1100a that ranges from a first wavelength 1101 to a second wavelength 1103. The plurality of light detectors 811, 812, 813 and 814 may detect light signals of wavelength bands 1100b that are subdivided from the wavelength band 1100a.

Figure 12A:
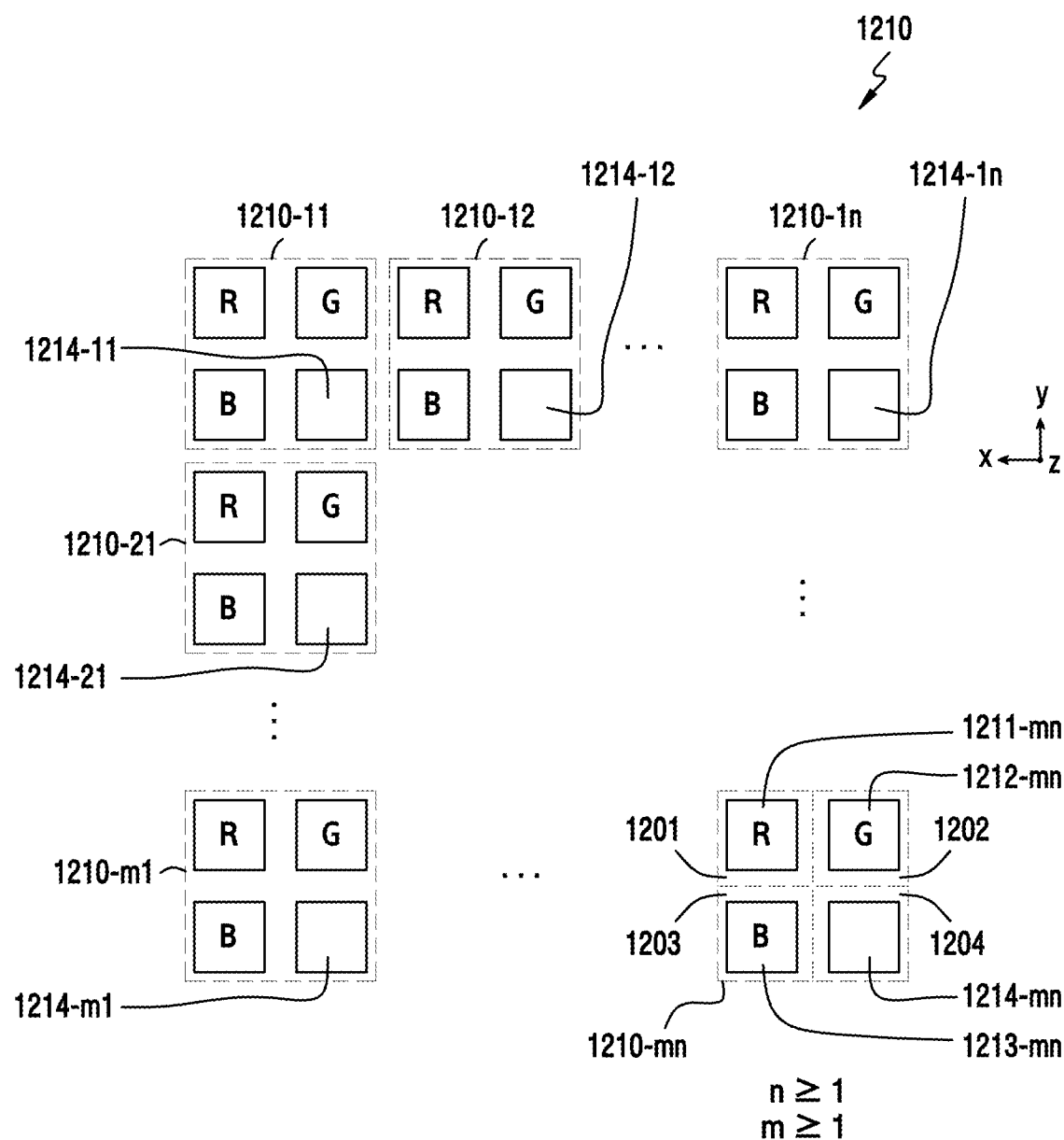
FIG. 12A is a block diagram illustrating a light receiving unit of a spectrometric sensing apparatus according to an embodiment of the present disclosure.
Figure 12B:
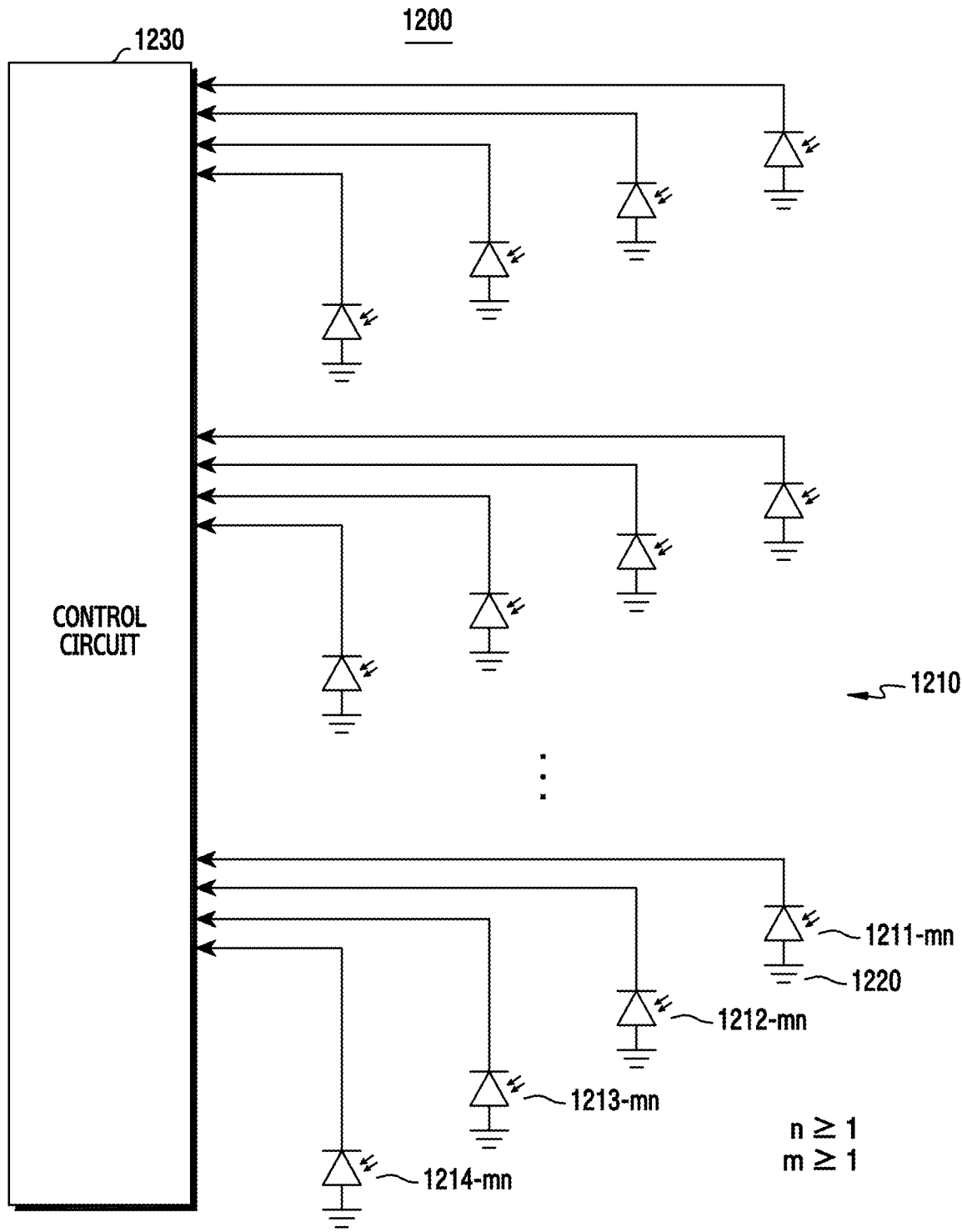
FIG. 12B is a light receiving circuit diagram of a spectrometric sensing apparatus according to an embodiment of the present disclosure.

FIG. 12A is a block diagram illustrating a light receiving unit of a spectrometric sensing apparatus according to an embodiment of the present disclosure. FIG. 12B is a light receiving circuit diagram of a spectrometric sensing apparatus according to an embodiment of the present disclosure.

Referring to FIG. 12A and FIG. 12B, the light receiving circuit 1200 may include a light receiving unit 1210 and a control circuit 1230. According to various embodiments, the light receiving unit 1210 may include at least a portion of the light receiving unit 460 of FIG. 5B.

According to an embodiment, in a top view for the light receiving circuit 1200, the light receiving unit 1210 may include at least one light detector 1210-$ij$, where $1 \leq i \leq m$ and $1 \leq j \leq n$, that is arrayed in an x-axis direction (e.g., direction going from the edge 410-13 of FIG. 4A to the edge 410-14) and/or a y-axis direction (direction going from the edge 410-11 of FIG. 4A to the edge 410-12).

According to an embodiment, in the top view, the light detector 1210-$ij$ may include four regions 1201, 1202, 1203 and 1204. The four regions 1201, 1202, 1203 and 1204 may be disposed in the form of a 2×2 matrix. A first light detector 1211-$ij$ may be disposed in the first region 1201. A second light detector 1212-$ij$ may be disposed in the second region 1202. A third light detector 1213-$ij$ may be disposed in the third region 1203. A fourth light detector 1214-$ij$ may be disposed in the fourth region 1204.

According to an embodiment, one terminal of the light receiving unit 1210 may be electrically connected to a ground member 1220 (e.g., the ground of the PCB 510 of FIG. 5A) of an electronic device (e.g., the electronic device 101 of FIG. 1, the electronic device 201 of FIG. 2 or the electronic device 400 of FIG. 4A), and the other terminal of the light receiving unit 1210 may be electrically connected to the control circuit 1230. The light receiving unit 1210 may detect a light signal, and convert the detected light signal into an electrical signal, and transmit the converted electrical signal to the control circuit 1230. According to various embodiments, the light detectors 1211-$ij$, 1212-$ij$, 1213-$ij$ and 1214-$ij$ of the light receiving unit 1210 may be photo diodes.

According to an embodiment, the first light detector 1211-$ij$, the second light detector 1212-$ij$ and the third light detector 1213-$ij$ may be used for detecting external illuminance or intensity of light. For example, in an illuminance detection mode, the first light detector 1211-$ij$ may detect a light signal of a first wavelength band that corresponds to red (R). The second light detector 1212-*ij* may detect a light signal of a second wavelength band that corresponds to green (G). The third light detector 1213-*ij* may detect a light signal of a third wavelength band that corresponds to blue (B).

According to an embodiment, the fourth light detector 1214-*ij* may be designed to detect a light signal of at least one wavelength band that is different from the first wavelength band, the second wavelength band and the third wavelength band. According to various embodiments, the fourth light detector 1214-*ij* may be designed to detect a light signal of at least one wavelength band that is different from the fourth wavelength band that corresponds to white color or clear color. For example, the fourth light detector 1214-*ij* may be designed to detect UV light or IR light.

For example, the light receiving unit 1210 may include a plurality of light detectors 1210-*ij*. And, a plurality of fourth light detectors 1214-*ij* may be designed to detect light signals of mutually different wavelength bands, respectively, as in examples of FIGS. 9A, 9B, 9C and 9D.

For another example, the light receiving unit 1210 may include the plurality of light detectors 1210-*ij*. And, the plurality of fourth light detectors 1214-*ij* may be designed to not only detect light signals of mutually different wavelength bands, but also detect light signals of similar or identical wavelength bands, as in examples of FIGS. 10A, 10B, 10C and 10D.

For further example, the light receiving unit 1210 may include the plurality of light detectors 1210-*ij*. And, the plurality of fourth light detectors 1214-*ij* may be designed to detect light signals of a plurality of wavelength bands that are subdivisions of a wavelength band for a specific detection mode, as in examples of FIGS. 11A and 11B as well.

According to an embodiment, the plurality of fourth light detectors 1214-*ij* may detect light signals in various detection modes that are different from an illuminance detection mode. For example, in a biometric detection mode, the plurality of fourth light detectors 1214-*ij* may detect light signals to generate an electrical signal for a medical state of the user body. For example, at least one of the plurality of fourth light detectors 1214-*ij* may be used in the biometric detection mode for detecting skin moisture. At least one of the plurality of fourth light detectors 1214-*ij* may be used in the biometric detection mode for detecting skin melanin. At least one of the plurality of fourth light detectors 1214-*ij* may be used in the biometric detection mode for detecting skin temperature. At least one of the plurality of fourth light detectors 1214-*ij* may be used in the biometric detection mode for detecting a heart rate. The plurality of fourth light detectors 1214-*ij* may be used in various biometric detection modes for detecting other various biometric information.

According to an embodiment, when one detection mode is selected, the control circuit 1230 may select and activate at least a part of the light receiving unit 1210.

For example, when an illuminance detection mode is selected, the control circuit 1230 may select and activate the first light detector 1211-*ij*, second light detector 1212-*ij* and third light detector 1213-*ij* of at least one light detector 1210-*ij*. In the illuminance detection mode, the first light detector 1211-*ij* may detect a light signal of a first wavelength band, and the second light detector 1212-*ij* may detect a light signal of a second wavelength band, and the third light detector 1213-*ij* may detect a light signal of a third wavelength band.

For another example, when a detection mode (e.g., a biometric detection mode) different from the illuminance detection mode is selected, the control circuit 1230 may select and activate the fourth light detector 1214-*ij* of at least one light detector 1210-*ij*. According to an embodiment, in the biometric detection mode, the fourth light detector 1214-*ij* may detect a light signal of a corresponding wavelength band.

For yet another example, when a multi detection mode is selected, the control circuit 1230 may select and activate the first light detector 1211-*ij*, second light detector 1212-*ij*, third light detector 1213-*ij* and fourth light detector 1214-*ij* of at least one light detector 1210-*ij*. For example, the multi detection mode may include the illuminance detection mode and the biometric detection mode. In the illuminance detection mode, the first light detector 1211-*ij*, the second light detector 1212-*ij* and the third light detector 1213-*ij* each may detect light signals of corresponding wavelength bands. In the biometric detection mode, the fourth light detector 1214-*ij* may detect a light signal of a corresponding wavelength band.

According to another embodiment, the first light detector 1211-*ij* may be designed to detect not only a light signal of a first wavelength band that corresponds to red (R), but also a light signal of a fifth wavelength band that is different from the first wavelength band. The second light detector 1212-*ij* may be designed to detect not only a light signal of a second wavelength band that corresponds to green (G), but also a light signal of a sixth wavelength band that is different from the second wavelength band. The third light detector 1213-*ij* may be designed to detect not only a light signal of a third wavelength band that corresponds to blue (B), but also a light signal of a seventh wavelength band that is different from the third wavelength band. In this case, the fourth light detector 1214-*ij* may be designed to detect a light signal of a fourth wavelength band that corresponds to white color or clear color. According to various embodiments, the fourth light detector 1214-*ij* may be designed to detect not only the light signal of the fourth wavelength band, but also a light signal of an eighth wavelength band that is different from the fourth wavelength band as well.

According to an embodiment, the fifth wavelength band, the sixth wavelength band, the seventh wavelength band and the eighth wavelength band may or may not at least partially overlap.

According to various embodiments, at least some of the fifth wavelength band, the sixth wavelength band, the seventh wavelength band and the eighth wavelength band may be wavelength bands for various detection modes that are different from the illuminance detection mode. For example, in the biometric detection mode, the light receiving unit 1210 may detect light signals of the fifth wavelength band, the sixth wavelength band, the seventh wavelength band and the eighth wavelength band.

According to an embodiment, in the biometric detection mode, the light receiving unit 1210 may detect a light signal of any one of the fifth wavelength band, the sixth wavelength band, the seventh wavelength band and the eighth wavelength band. According to various embodiments, in the biometric detection mode, the light receiving unit 1210 may detect light signals of several of the fifth wavelength band, the sixth wavelength band, the seventh wavelength band and the eighth wavelength band as well.

According to an embodiment, when at least one detection mode is selected, the control circuit 1230 may select and activate at least a part of the light receiving unit 1210.

According to an embodiment, in the illuminance detection mode, the light receiving unit 1210 may detect a light signal of a first wavelength band, and generate a first electrical signal. In the illuminance detection mode, the light receiving unit 1210 may detect a light signal of a second wavelength band, and generate a second electrical signal. In the illuminance detection mode, the light receiving unit 1210 may detect a light signal of a third wavelength band, and generate a third electrical signal. According to various embodiments, in the illuminance detection mode, the light receiving unit 1210 may detect a light signal of a fourth wavelength band, and generate a fourth electrical signal. In the illuminance detection mode, the light receiving unit 1210 may detect a light signal of a fifth wavelength band that is different from an illuminance detecting wavelength band, and generate a fifth electrical signal. In the illuminance detection mode, the light receiving unit 1210 may detect a light signal of a sixth wavelength band that is different from the illuminance detecting wavelength band, and generate a sixth electrical signal. In the illuminance detection mode, the light receiving unit 1210 may detect a light signal of a seventh wavelength band that is different from the illuminance detecting wavelength band, and generate a seventh electrical signal. In the illuminance detection mode, the light receiving unit 1210 may detect an light signal of a eighth wavelength band that is different from the illuminance detecting wavelength band, and generate an eighth electrical signal. In the illuminance detection mode, the control circuit 1230 may process the fifth electrical signal, the sixth electrical signal, the seventh electrical signal and the eighth electrical signal as invalid.

According to another embodiment, in the biometric detection mode, the light receiving unit 1210 may detect a light signal of a fifth wavelength band, and generate a fifth electrical signal. In the biometric detection mode, the light receiving unit 1210 may detect a light signal of a sixth wavelength band, and generate a sixth electrical signal. In the biometric detection mode, the light receiving unit 1210 may detect a light signal of a seventh wavelength band, and generate a seventh electrical signal. In the biometric detection mode, the light receiving unit 1210 may detect a light signal of an eighth wavelength band, and generate an eighth electrical signal. According to various embodiments, in the biometric detection mode, the light receiving unit 1210 may detect a light signal of a first wavelength band that is different from the biometric detecting wavelength band, and generate a first electrical signal. In the biometric detection mode, the light receiving unit 1210 may detect a light signal of a second wavelength band that is different from the biometric detecting wavelength band, and generate a second electrical signal. In the biometric detection mode, the light receiving unit 1210 may detect a light signal of a third wavelength band that is different from the biometric detecting wavelength band, and generate a third electrical signal. In the biometric detection mode, the light receiving unit 1210 may detect a light signal of a fourth wavelength band that is different from the biometric detecting wavelength band, and generate a fourth electrical signal. In the biometric detection mode, the control circuit 1230 may process the first electrical signal, the second electrical signal, the third electrical signal and the fourth electrical signal as invalid.

According to an embodiment, when a multi detection mode including the illuminance detection mode and the biometric detection mode is selected, the light receiving unit 1210 may detect light signals of illuminance detecting wavelength bands, and generate illuminance detecting electrical signals. In the multi detection mode, the light receiving unit 1210 may detect light signals of biometric detecting wavelength bands, and generate biometric detecting electrical signals. In the multi detection mode, the control circuit 1230 may process the illuminance detecting electrical signal and/or the biometric detecting electrical signal as valid.

Figure 13:
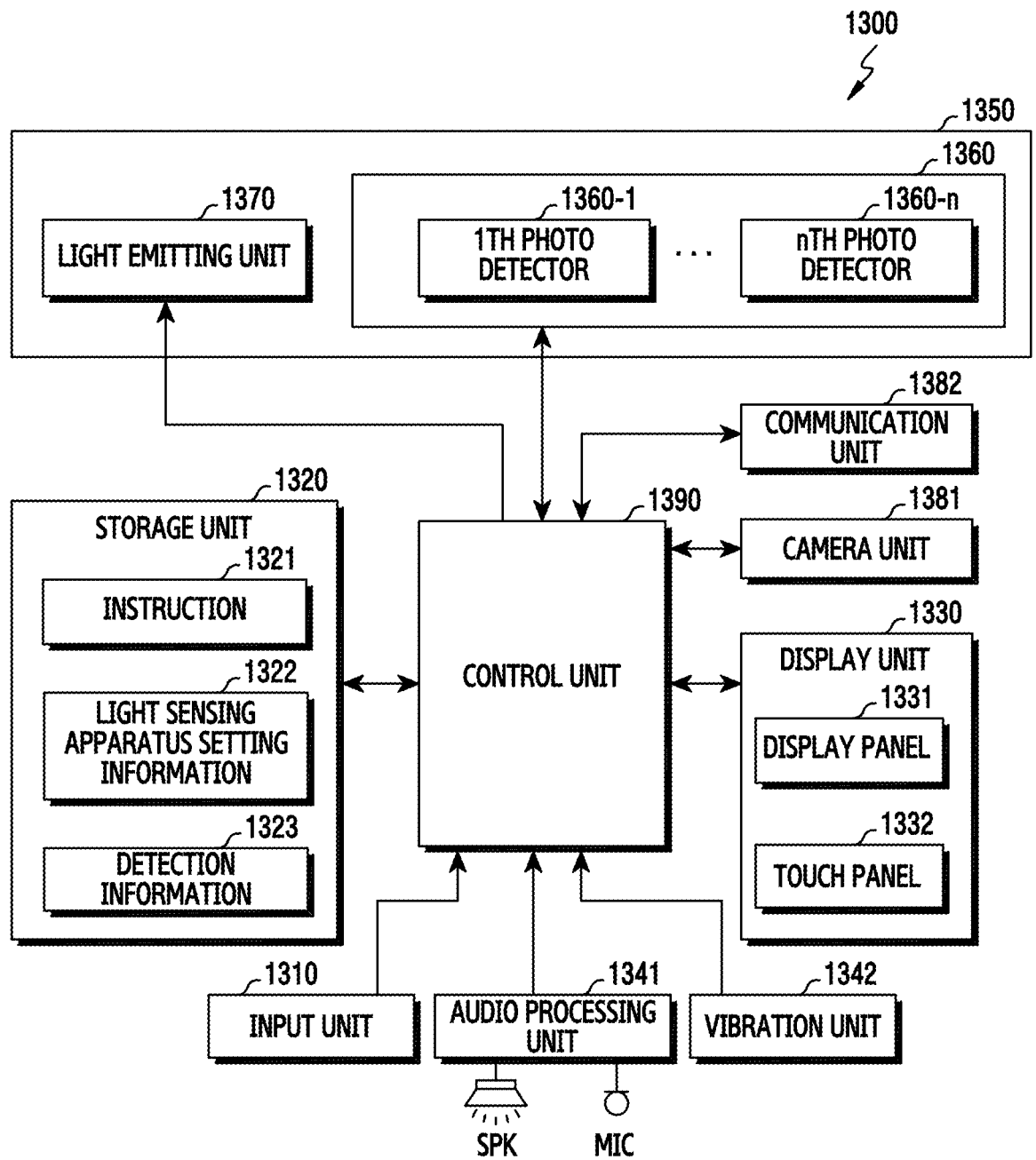
FIG. 13 is a block diagram of an electronic device that provides a spectrometric sensing function according to an embodiment of the present disclosure.

FIG. 13 is a block diagram of an electronic device that may provide a spectrometric sensing function according to an embodiment of the present disclosure. According to various embodiments, the electronic device 1300 may include the entire or a part of the electronic device 101 of FIG. 1, the electronic device 201 of FIG. 2 and/or the electronic device 400 of FIGS. 4A and 4B.

According to an embodiment, the electronic device 1300 may select at least one detection mode on the basis of an instruction 1321. On the basis of the instruction 1321, the electronic device 1300 may set a spectrometric sensing apparatus 1350 in accordance with the selected detection mode. For example, when a call application is executed, the electronic device 1300 may select a proximity detection mode and/or a biometric detection mode. The electronic device 1300 may adjust the light emitting unit 1370 of the spectrometric sensing apparatus 1350 and/or the light receiving unit 1360 thereof on the basis of spectrometric sensing apparatus setting information 1322 in accordance with the selected proximity detection mode and/or biometric detection mode.

According to an embodiment, when a detection mode is selected, the electronic device 1300 may acquire detection information through the spectrometric sensing apparatus 1350. The electronic device 1300 may output the acquired detection information through a screen of a display unit 1330. For example, the detection information may be information about a medical state of the user (e.g., skin moisture, skin melanin, skin temperature, heart rate, blood flow speed, etc. of the user body).

Referring to FIG. 13, the electronic device 1300 may include an input unit 1310, a storage unit 1320, the display unit 1330, the spectrometric sensing apparatus 1350 and a control unit 1390.

The input unit 1310 (e.g., the input device 250 of FIG. 2) may be configured to generate various input signals that are required for operation of the electronic device 1300. The input unit 1310 may include various input means such as a keyboard, a keypad, a key button, a touch button, etc. in accordance with the compatibility or non-compatibility of the electronic device 1300. According to an embodiment, the input unit 1310 may trigger various types of user inputs for the execution of the instruction 1321. Or, the input unit 1310 may trigger a user input for the spectrometric sensing apparatus setting information 1322.

The storage unit 1320 (e.g., the memory 230 of FIG. 2) may store various basic operating systems required for operation of the electronic device 1300, data corresponding to various user functions, an application program and algorithm and the like. According to an embodiment, the storage unit 1320 may store various instructions 1321. The storage unit 1320 may store the setting information 1322 of the spectrometric sensing apparatus 1350 for supporting a detection mode that is defined by the instruction 1321. The storage unit 1320 may store detection information 1323 that is detected through the spectrometric sensing apparatus 1350.

According to an embodiment, the instruction 1321 may include a selection routine for selecting detection modes of the spectrometric sensing apparatus 1350 on the basis of various types of triggers (e.g., predefined input generation, predefined application execution or the like) that are generated from the electronic device 1300. In accordance with various embodiments, the instruction 1321 may include a selection routine for selecting detection modes on the basis of various types of triggers received from external inputs as well. In accordance with various embodiments, the instruction 1321 may include a setting routine for setting the spectrometric sensing apparatus 1350 in accordance with the selected detection mode. In accordance with various embodiments, the instruction 1321 may include an acquisition routine for acquiring a signal for information that is detected through the spectrometric sensing apparatus 1350 in the selected detection mode. In accordance with various embodiments, the instruction 1321 may include a processing routine for processing a signal for the acquired detection information.

The display unit 1330 may be designed to provide various screen interfaces that are required for operation of the electronic device 1300. According to an embodiment, the display unit 1330 may include a touch screen that overlaps a display panel 1331 (e.g., the display 260 of FIG. 2) and a touch panel 1332 (e.g., the touch panel 252 of FIG. 2). The display panel 1331 may, for example, display various screens such as an image, a text, etc. that are based on the instruction 1321. The touch panel 1332 may be designed to receive, for example, various touch inputs for a screen that is displayed through the display panel 1331 on the basis of the instruction 1321.

According to an embodiment, the spectrometric sensing apparatus 1350 may include the light receiving unit 1360 and the light emitting unit 1370. The light receiving unit 1360 may include at least one light detector 1360-$i$, where $1 \le i \le n$. According to various embodiments, the light receiving unit 1360 may include the light receiving unit 460 of FIG. 5A, 5B, 5C, 6A, 6B, 6C, 7A, 7B, 7C, 7D or 7E, the light receiving unit 810 of FIG. 8 or the light receiving unit 1210 of FIGS. 12A and 12B, and its detailed description is omitted.

The light emitting unit 1370 may include at least one light emitter not illustrated. According to various embodiments, the light emitting unit 1370 may include the light emitting unit 470 of FIGS. 4A to 5B.

According to an embodiment, the light emitting unit 1370 may include a light emitter that may generate light of all wavelength bands, so that the light receiving unit 1360 may detect light signals from the reflected light. For example, the light emitting unit 1370 may be designed as a single light emitter. The single light emitter may be a light emitting element that may generate light of a broad wavelength band.

According to another embodiment, the light emitting unit 1370 may include a plurality of light emitters that may generate light of a plurality of wavelength bands respectively. For example, in a first detection mode, the control unit 1390 may select and activate a first light detector 1360-1 for detecting light of a first detecting wavelength band generated by the light emitting unit 1370. For another example, in a second detection mode, the control unit 1390 may select and activate a second light detector (not shown) for detecting light of a second detecting wavelength band generated by the light emitting unit 1370.

According to a further embodiments, the light emitting unit 1370 may be designed to selectively generate light of a corresponding wavelength band in accordance with the control of the control unit 1390 (e.g., the processor 120 of FIG. 1 or the processor 210 of FIG. 2). For example, in a first detection mode, the control unit 1390 may control the light emitting unit 1370 to generate light of a first detecting wavelength band. In a second detection mode, the control unit 1390 may control the light emitting unit 1370 to generate light of a second detecting wavelength band. According to various embodiments, in the biometric detection mode, the control circuit 1390 may control the light emitting unit 470 to generate light of a biometric detecting wavelength band, i.e. light in a wavelength band that is appropriate for biometric detection.

Figure 14:
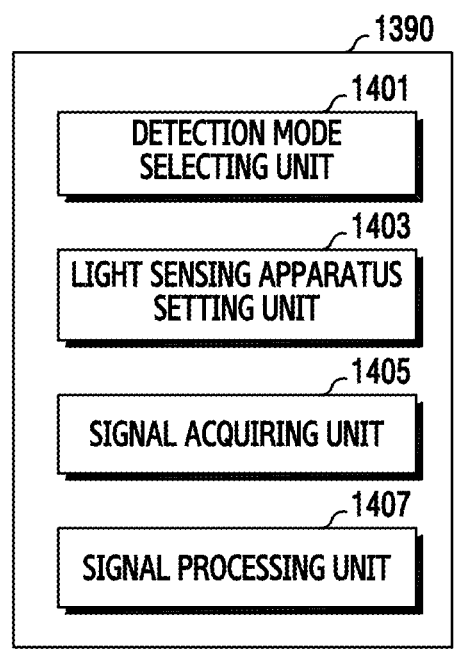
FIG. 14 is a block diagram illustrating in more detail a control unit according to an embodiment of the present disclosure.

The control unit 1390 (e.g., the processor 120 of FIG. 1 or the processor 210 of FIG. 2) may be configured to control various signal flow control, information gathering and output, and the like in order to support a spectrometric sensing function according to an embodiment. According to an embodiment, the control unit 1390 may, as illustrated in FIG. 14, include constituent elements (e.g., a detection mode selecting unit 1401, a spectrometric sensing apparatus setting unit 1403, a signal acquiring unit 1405 and a signal processing unit 1407).

According to an embodiment, the control unit 1390 may sense various types of triggers generated from the electronic device 1300 or various types of external triggers, and select at least one detection mode on the basis of the instruction 1321. According to various embodiments, on the basis of the instruction 1321, the control unit 1390 may set the spectrometric sensing apparatus 1350 in accordance with the selected detection mode. According to various embodiments, on the basis of the instruction 1321, the control unit 1390 may acquire a signal outputted through the spectrometric sensing apparatus 1350 in the selected detection mode. According to various embodiments, on the basis of the instruction 1321, the control unit 1390 may process a signal for the acquired detection information.

According to various embodiments, the electronic device 1300 may further include an audio processing unit 1341, a vibration unit 1342, a camera unit 1381 or a communication unit 1382.

The audio processing unit 1341 (e.g., the audio module 280 of FIG. 2) may output, through a speaker (SPK), various audio data for operation of the electronic device 1300, audio data received from an external device (e.g., the first external electronic device 102, the second external electronic device 104 or the server 106 in FIG. 1). According to an embodiment, the audio processing unit 1341 may output various sound effects or announcement sounds related to a spectrometric sensing function in accordance with the control of the control unit 1390. For example, when the biometric detection mode is selected, the audio processing unit 1341 may output, through the speaker (SPK), a voice notification that the biometric detection mode has been selected in accordance with the control of the control unit 1390. For example, in case where biometric information (e.g., skin moisture, skin melanin, etc.) is recognized in the biometric detection mode, the audio processing unit 1341 may output a synthesized voice for notifying the completion of biometric detection by the speaker (SPK) in accordance with the control of the control unit 1390. According to various embodiments, the various sound effects or announcement sounds related with the spectrometric sensing function may be changed by user configuration setting.

According to various embodiments, the audio processing unit 1341 may include an audio decoder (not shown) and a Digital to Analog Converter (DAC) (not shown). The audio decoder may convert audio data stored in the storage unit 1320 into a digital audio signal. The DAC may convert the digital audio signal converted by the audio decoder into an analog audio signal.

The audio processing unit 1341 may receive a voice signal through a microphone (MIC). For example, the audio processing unit 1341 may include an Analog to Digital Converter (ADC) (not shown). The ADC may convert an analog voice signal from the microphone (MIC) into a digital voice signal. According to an embodiment, the audio processing unit 1341 may receive various voice inputs related with spectrometric sensing functions in accordance with the control of the control unit 1390. For example, the audio processing unit 1341 may sense a voice input for a selection of the biometric detection mode through the microphone (MIC), and forward the sensed voice input to the control unit 1390.

The vibration unit 1342 may include at least one vibrator (not shown) that is disposed in the electronic device 1300. The vibration unit 1342 may activate a vibrator in various vibration patterns on the basis of various types of triggers generated from the electronic device 1300 in accordance with the control of the control unit 1390. According to various embodiments, the vibration unit 1342 may activate the vibrator in various vibration patterns on the basis of various types of external triggers in accordance with the control of the control unit 1390. For example, the external triggers may be received from an external device (e.g., the first external electronic device 102, the second external electronic device 104 or the server 106 in FIG. 1). According to an embodiment, the vibration unit 1342 may trigger a vibration related with a spectrometric sensing function in accordance with the control of the control unit 1390. For example, when the proximity detection mode and the biometric detection mode are selected, and the proximity distance sensed through the proximity detection mode is equal to or is less than a reference, the vibration unit 1342 may trigger a vibration for notifying biometric detection has started in accordance with the control of the control unit 1390.

The camera unit 1381 may be designed to activate a camera function in various modes in accordance with the control of the control unit 1390. According to an embodiment, the camera unit 1381 may operate in relation with a spectrometric sensing function in accordance with the control of the control unit 1390. For example, the camera unit 1381 may be designed such that the biometric detection mode is activated when the camera function is activated.

The communication unit 1382 (e.g., the communication module 220 of FIG. 2) may be configured to support a communication function of the electronic device 1300. To support the communication function (e.g., mobile communication function) of the electronic device 1300, the communication unit 1382 may be a mobile communication module. The communication unit 1382 may establish a communication channel with another mobile communication system, to support signal transmission/reception for execution of the mobile communication function of the electronic device 1300. For example, the communication unit 1382 may establish a voice service channel, an image service channel or a data service channel with the mobile communication system, and support transmission/reception of a specific signal according to the corresponding service channel. According to an embodiment, the communication unit 1382 may operate in relation with the spectrometric sensing function in accordance with the control of the control unit 1390. For example, biometric information detected in the biometric detection mode may be transmitted to an external device (e.g., server) through the communication unit 1382.

According to various embodiments, the electronic device 1300 may further include various modules in accordance with the form of provision thereof. For example, the electronic device 1300 may further include constituent elements not mentioned above, such as a short range communication module for short range communication, an interface for data transmission/reception of a wired communication scheme or a wireless communication scheme of the electronic device 1300, an Internet communication module for communicating with an Internet network to perform an Internet function, a digital broadcasting module for performing a function of digital broadcasting reception and playback and the like. Because these constituent elements are so diversely changed according to the convergence trend of a digital device, all of them may not be enumerated, but constituent elements of levels equivalent to those of the above mentioned constituent elements may be further included in the electronic device 1300. Undoubtedly, the electronic device 1300 according to various embodiments may exclude specific constituent elements from the above constituent elements or replace the same with other constituent elements in accordance with the form of provision thereof. This will be able to be easily understood by a person having ordinary skill in the art to which the disclosure pertains.

FIG. 14 is a block diagram illustrating in more detail the control unit 1390 according to an embodiment of the present disclosure.

Referring to FIG. 14, the control unit 1390 according to an embodiment may include the detection mode selecting unit 1401, the spectrometric sensing apparatus setting unit 1403, the signal acquiring unit 1405 and the signal processing unit 1407.

According to an embodiment, the detection mode selecting unit 1401 may sense various types of triggers generated from the electronic device 1300 or various types of external triggers, and select at least one detection mode. For example, the detection mode selecting unit 1401 may be set to activate a proximity detection mode during when the electronic device has an active phone call. The detection mode selecting unit 1401 may select the proximity detection mode during the call. For another example, the detection mode selecting unit 1401 may be set to activate the biometric detection mode when a proximity distance sensed through the proximity detection mode is equal to or is less than a reference. When the proximity distance sensed through the proximity detection mode is equal to or is less than a reference distance, the detection mode selecting unit 1401 may select the biometric detection mode. For further example, while a front camera is activated, the detection mode selecting unit 1401 may activate the biometric detection mode. While the front camera function is activated, the detection mode selecting unit 1401 may inactivate the biometric detection mode. For yet another example, the detection mode selecting unit 1401 may sense the execution of an application, and select at least one detection mode corresponding to the executed application. For still another example, the detection mode selecting unit 1401 may select a detection mode on the basis of various types of user inputs, a motion of the electronic device 1300, etc. Besides this, the detection mode selecting unit 1401 may select the detection mode in accordance with various types of triggers.

According to an embodiment, the spectrometric sensing apparatus setting unit 1403 may set the spectrometric sensing apparatus (1350 of FIG. 13) in accordance with the selected at least one detection mode. For example, the spectrometric sensing apparatus setting unit 1403 may select at least one light detector for the selected detection mode from the light receiving unit 1360, to activate the selected light detector.

According to an embodiment, the light emitting unit (1370 of FIG. 13) may be designed to selectively generate light of various wavelength bands in accordance with the control of the spectrometric sensing apparatus setting unit 1403 as well. For example, in the proximity detection mode, the spectrometric sensing apparatus setting unit 1403 may control the light emitting unit 1370 to generate light of a proximity detecting wavelength band, i.e. a wavelength band appropriate for proximity detection. For another example, in the gesture detection mode, the spectrometric sensing apparatus setting unit 1403 may control the light emitting unit 1370 to generate light of a gesture detecting wavelength band. For further example, in the biometric detection mode, the spectrometric sensing apparatus setting unit 1403 may control the light emitting unit 1370 to generate light of a biometric detecting wavelength band.

According to an embodiment, the light emitting unit (1370 of FIG. 13) may include a plurality of light emitters. And, the plurality of light emitters may generate light of mutually different wavelength bands. For example, one light emitter may generate light of a first wavelength band, and another one light emitter may generate light of a second wavelength band that is different from the first wavelength band. For another example, in the proximity detection mode, the spectrometric sensing apparatus setting unit 1403 may select and activate at least one light emitter that generates light of a proximity detecting wavelength band among the plurality of light emitters of the light emitting unit 1370. For further example, in the gesture detection mode, the spectrometric sensing apparatus setting unit 1403 may select and activate at least one light emitter that generates light of a gesture detecting wavelength band among the plurality of light emitters of the light emitting unit 1370. For yet another example, in the biometric detection mode, the spectrometric sensing apparatus setting unit 1403 may select and activate at least one light emitter that generates light of a biometric detecting wavelength band among the plurality of light emitters of the light emitting unit 1370.

According to an embodiment, the signal acquiring unit 1405 may acquire a signal that is outputted through the spectrometric sensing apparatus 1350 in the selected detection mode. For example, in the proximity or gesture detection mode, the spectrometric sensing apparatus (1350 of FIG. 13) may detect a light signal of a proximity or gesture detecting wavelength band, and generate and transmit an electrical signal to the signal acquiring unit 1405. For another example, in the illuminance detection mode, the spectrometric sensing apparatus 1350 may detect a light signal of an illuminance detecting wavelength band, and generate and transmit an electrical signal to the signal acquiring unit 1405. For further example, in the biometric detection mode, the spectrometric sensing apparatus 1350 may detect a light signal of a biometric detecting wavelength band, and generate and transmit an electrical signal to the signal acquiring unit 1405.

According to an embodiment, the signal processing unit 1407 may process a signal for detection information transmitted from the signal acquiring unit 1405. For example, when a first detection mode is selected, the spectrometric sensing apparatus 1350 may detect a light signal of a first wavelength band for the first detection mode, and generate and transmit a first electrical signal to the signal acquiring unit 1405. On the basis of the first detection mode, the signal processing unit 1407 may detect information from the first electrical signal, and process the detected information. The operation of processing the detected information may include the operation of displaying the detected information through a display unit (e.g., the display unit 1330 of FIG. 13), the operation of transmitting the detected information to an external device, etc. According to various embodiments, when the first detection mode is selected, the spectrometric sensing apparatus 1350 may further detect a light signal of a second wavelength band that is different from the first wavelength band for the first detection mode, and generate and transmit a second electrical signal to the signal acquiring unit 1405. In the first detection mode, the signal processing unit 1407 may process the second electrical signal as invalid.

According to an embodiment of the present disclosure, an electronic device may include a housing, a display within the housing and exposed through a surface of the housing, a light emitting unit and a light receiving unit within the housing, and a processor electrically coupled with the display, the light emitting unit and the light receiving unit. The light emitting unit may include at least one light source for outputting light of at least one wavelength band. The light receiving unit may include at least one region for receiving the light of the at least one wavelength band. The processor may control a function of the light emitting unit and/or the light receiving unit based on at least one mode. For example, the processor may control an operating wavelength band of the light emitting unit and/or the light receiving unit based on at least one mode.

According to an embodiment of the present disclosure, the processor may control the light emitting unit to selectively output light of a wavelength band that corresponds to the at least one mode.

According to an embodiment of the present disclosure, the light emitting unit may include a plurality of light sources for outputting light of mutually different wavelength bands respectively, and the processor may selectively activate at least one of the plurality of light sources based on the at least one mode.

According to an embodiment of the present disclosure, the processor may selectively activate at least a part of at least one region of the light receiving unit based on the at least one mode.

According to an embodiment of the present disclosure, the processor may acquire information related with the at least one mode based on the light received by the light receiving unit, and display the acquired information using the display.

According to an embodiment of the present disclosure, the electronic device may further include a communication module, and the processor may acquire information related with the at least one mode based on the light received by the light receiving unit, and transmit the acquired information to another electronic device through the communication module.

According to an embodiment of the present disclosure, the light receiving unit may include at least a part of one or more first regions for receiving light of a proximity detecting wavelength band, one or more second regions for receiving light of an illuminance detecting wavelength band, and/or one or more third regions for receiving light of a biometric detecting wavelength band.

According to an embodiment of the present disclosure, in a first mode, the light receiving unit may detect light of a first wavelength band for the first mode and light of a second wavelength band for a second mode that is different from the first mode. The light receiving unit may convert the light of the first wavelength band into a first electrical signal and the light of the second wavelength band into a second electrical signal, and may transmit the first electrical signal and the second electrical signal to the processor. The processor may process the second electrical signal as invalid.

According to an embodiment of the present disclosure, the light receiving unit may include at least one diode, and a filter disposed on an upper surface of each of the at least one diode. The filter may be adapted to filter light of at least one specific wavelength band.

According to an embodiment of the present disclosure, the surface of the housing may include one light transmission region for the light emitting unit and the light receiving unit, or include a first light transmission region for the light emitting unit, and a second light transmission region isolated from the first light transmission region and for the light receiving unit.

Figure 15:
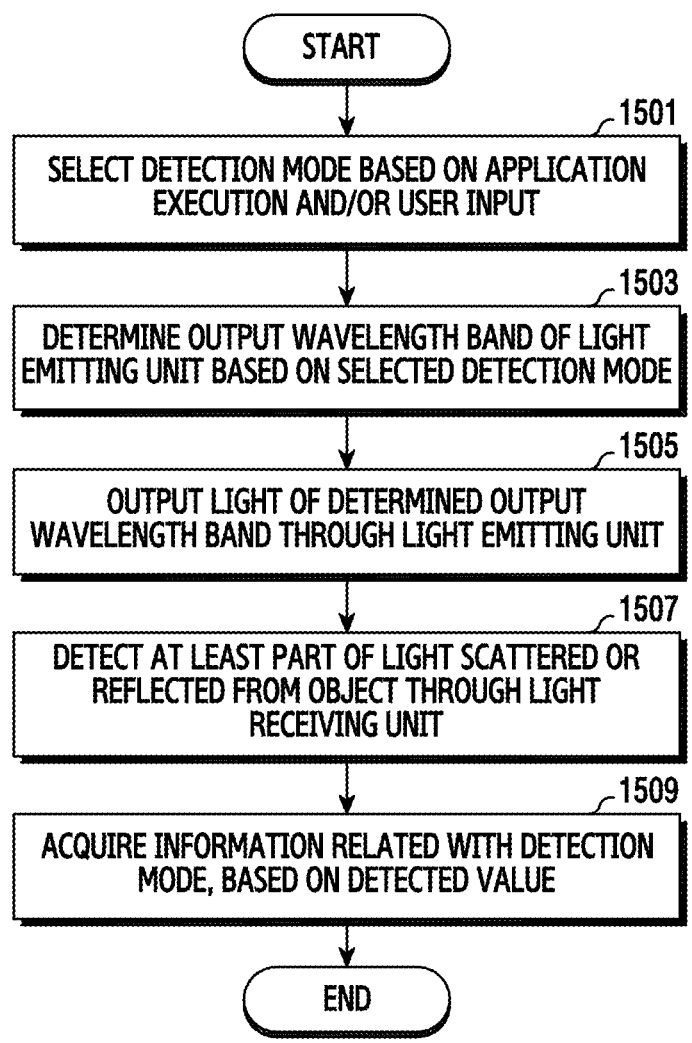
FIG. 15 is a flowchart illustrating an operation flow of a spectrometric sensing method according to an embodiment of the present disclosure.
Figure 16A:
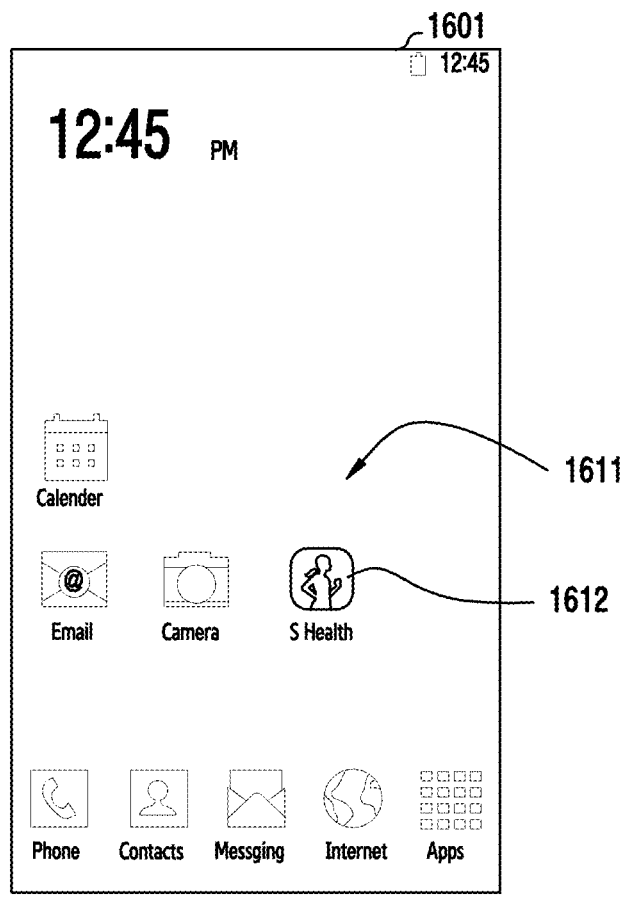
FIG. 16A and FIG. 16B are diagrams further explaining the operation flow of FIG. 15 according to various embodiments of the present disclosure.
Figure 16B:
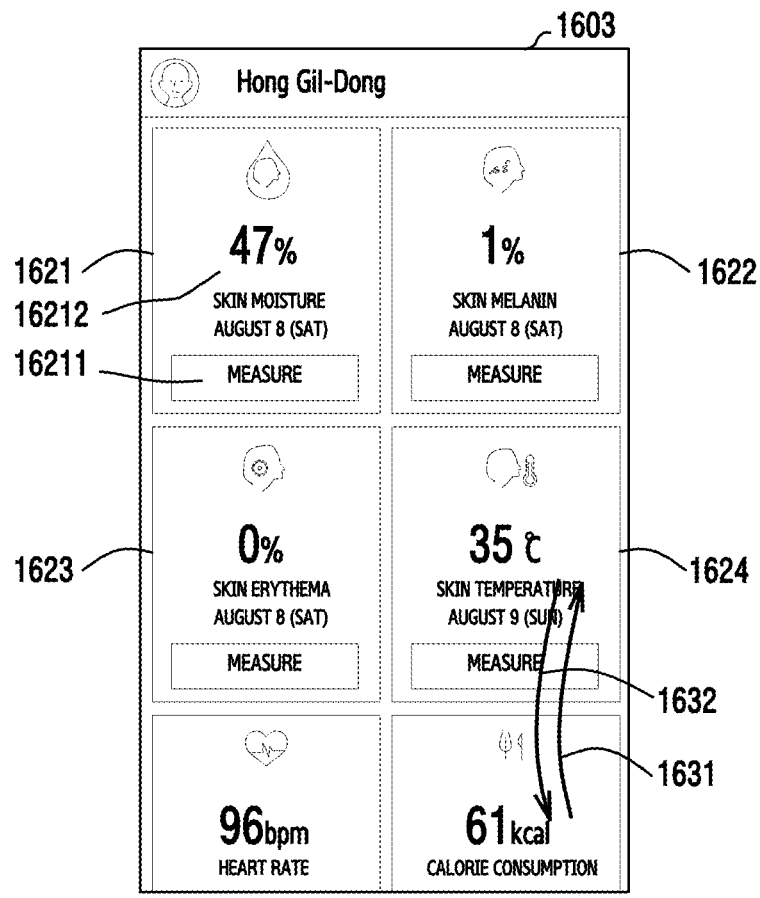

FIG. 15 is a flow chart illustrating an operation flow of a spectrometric sensing method according to an embodiment of the present disclosure. FIGS. 16A and 16B are diagrams further explaining the operation flow of FIG. 15 according to various embodiments of the present disclosure.

Referring to FIG. 15, in operation 1501, the control unit (1390 of FIG. 13) (e.g., the processor 120 of FIG. 1 or the processor 210 of FIG. 2) may select a detection mode based at least partly on the execution of an application and/or a user input.

In accordance with various embodiments of the present disclosure, referring to FIG. 16A, the electronic device (1300 of FIG. 13) may display a plurality of icons 1611 through a screen 1601. The plurality of icons 1611 may represent applications that are stored in the electronic device 1300. If it is sensed that an icon 1612 representing a health care application is selected among the plurality of icons 1611 by a user input (e.g., a touch input), the control unit 1390 may execute the health care application. Referring to FIG. 16B according to various embodiments, the control unit 1390 may display a screen 1603 (below, a 'detection function list screen') providing a list (below, a 'detection function list') of various detection functions (detection applications or detection application programs) in accordance with instructions of the executed health care application. The detection function list may be displayed through various types of GUI elements.

According to various embodiments, the control unit 1390 may set a display region of the detection function list screen 1603 as a scrollable region. In case where other list entries, more than the display is capable of displaying at one time, exist, the control unit 1390 may set the detection function list screen 1603 as a scrollable region. In case where a touch input 1631 or 1632 of a scheme in which one point is touched on the detection function list screen 1603, and the touch is dragged toward another point of a roughly vertical direction is sensed, the control unit 1390 may scroll to display the other list entries. According to various embodiments, in case where a touch input (not shown) in which one point is touched on the detection function list screen 1603, and the touch is dragged toward another point of a roughly horizontal direction is sensed, the control unit 1390 may scroll to display the other list entries as well.

According to various embodiments, the detection function list may include various list entries for various biometric detection functions. For example, the various list entries may include a list entry 1621 for a skin moisture detection function, a list entry 1622 for a skin melanin detection function, a list entry 1623 for a skin erythema detection function, a list entry 1624 for a skin temperature detection function or the like. The list entries may include other list entries (not shown) for other various detection functions, such as a list entry for a heart rate detection function, a list entry for a blood flow speed detection function, a list entry for a blood sugar detection function, etc.

If it is sensed that at least one list entry is selected from the detection function list by a user input, the control unit 1390 may execute a detection function corresponding to the selected at least one list entry. According to an embodiment, in case where the control unit 1390 displays the list entry 1621 for the skin moisture detection function, the control unit 1390 may provide a GUI element (below, a 'button') 16211 for receiving a user input for detection function execution, and an information display region 16212 for displaying a skin moisture detection value. Likewise, other list entries 1622, 1623 and 1624 may be also displayed in this form. For example, in case where it is sensed that the button 16211 of the list entry 1621 for the skin moisture detection function is selected by a user input (e.g., a single tap), the control unit 1390 may execute the skin moisture detection function.

The control unit 1390 may select at least one detection mode based on the execution of a detection function. For example, at execution of the skin moisture detection function, the control unit 1390 may select the skin moisture detection mode. At execution of the skin melanin detection function, the control unit 1390 may select the skin melanin detection mode. At execution of the skin erythema detection function, the control unit 1390 may select the skin erythema detection mode. The selection of the detection mode signifies the activation of the detection mode. Upon activating the detection mode, the control unit 1390 may perform operation 1503 to operation 1509.

In operation 1503, the control unit 1390 may determine an output wavelength band of a light emitting unit (or light source) (e.g., the light emitting unit 1370 of FIG. 13) based on the selected detection mode.

For example, in case where the skin moisture detection mode is selected in accordance with the execution of the skin moisture detection function, the control unit 1390 may use the wavelength band including the maximum sensitivity wavelength of 880 nm and/or the wavelength band including the maximum sensitivity wavelength of 970 nm as the output wavelength band of the light emitting unit 1370 in accordance with the skin moisture detection mode.

For another example, in case where the skin melanin detection mode is selected according to the execution of the skin melanin detection function, the control unit 1390 may use the wavelength band including the maximum sensitivity wavelength of 660 nm and/or the wavelength band including the maximum sensitivity wavelength of 880 nm as the output wavelength band of the light emitting unit 1370 in accordance with the skin melanin detection mode.

For further example, in case where the skin erythema detection mode is selected according to the execution of the skin erythema detection function, the control unit 1390 may use the wavelength band including the maximum sensitivity wavelength of 568 nm and/or the wavelength band including the maximum sensitivity wavelength of 880 nm as the output wavelength band of the light emitting unit 1370 in accordance with the skin erythema detection mode.

According to various embodiments, as described above, in executing a biometric detection function (e.g., the skin moisture detection function, the skin melanin detection function, the skin erythema detection function or the like), the control unit 1390 may also select the proximity detection mode in conjunction with the biometric detection function in operation 1503, may use the wavelength band including the maximum sensitivity wavelength of 950 nm as the output wavelength band of the light emitting unit 1370 in accordance with the proximity detection mode. The control unit 1390 may obtain the proximity distance through the operations 1505 to 1509. The control unit 1390 may judge if the obtained proximity distance is equal to or is less than a threshold (e.g. about 10 cm). If the proximity distance is equal to or is less than the threshold, the control unit 1390 returns to operation 1501, and selects at least one biometric detection mode based on the executed biometric detection function. According to various embodiments, in the returned operation 1501, the control unit 1390 may release the selection of the proximity detection mode. The control unit 1390 may determine at least one output wavelength band of the light emitting unit 1370 in accordance with the selected at least one biometric detection mode in operation 1503.

In operation 1505, the control unit 1390 may control the light emitting unit 1370 to output light of the determined output wavelength band. The light emitting unit 1370 may be designed to selectively generate light of various wavelength bands in accordance with the control of the control unit 1390.

According to an embodiment, the light emitting unit 1370 may be a single light emitting element. The control unit 1390 may control the light emitting unit 1370 to output light of a wavelength band corresponding to the activated detection mode from the single light emitting element. The single light emitting element may selectively generate light of a wavelength band corresponding to the activated detection mode in accordance with the control of the control unit 1390.

According to another embodiment, the light emitting unit 1370 may include a plurality of light emitters (or light sources) that generate light of mutually different wavelength bands. The control unit 1390 may selectively activate some light emitters that generate light of a wavelength band corresponding to the activated detection mode among the plurality of light emitters as well.

In operation 1507, the control unit 1390 may detect, through a light receiving unit (e.g., the light receiving unit 1360 of FIG. 13), at least a part of light that is scattered or reflected from the object where a detection for the selected detection mode is taking place. For example, in case where the biometric mode, the object may be the user.

For example, in at least one detection mode that is selected based on the executed a biometric detection function (e.g., the skin moisture detection function, the skin melanin detection function, the skin erythema detection function or the like), light of a corresponding wavelength band discharged from the light emitting unit 1370 may be shone on the user's skin, when the user is in the vicinity (e.g., within 10 cm) of the electronic device (1300 of FIG. 13). The light may be absorbed, scattered or reflected by the user's skin. The scattered or reflected light may be transmitted to the light receiving unit 1360. Then, the light receiving unit 1360 may generate an electrical signal (or detection value) for a biometric measurement (e.g., skin moisture, skin melanin, skin erythema or the like) from the scattered or reflected light, and transmit the electrical signal to the control unit 1390.

For another example, the proximity detection mode may be preferentially selected according to the execution of a biometric detection function (e.g., the skin moisture detection function, the skin melanin detection function, the skin erythema detection function or the like), and light of a proximity detecting wavelength band outputted from the light emitting unit 1370 may be discharged according to the selection of the proximity detection mode. In case where the user is in the vicinity (e.g., within 10 cm) of the electronic device 1300, the light of the proximity detecting wavelength band may be scattered or reflected by the user, and the scattered or reflected light may be transmitted to the light receiving unit 1360. The light receiving unit 1360 may generate an electrical signal for proximity from the introduced scattered or reflected light, and transmit the electrical signal to the control unit 1390. As stated above, the control unit 1390 may obtain the proximity distance through the operations 1505 to 1509. The control unit 1390 may judge if the obtained proximity distance is equal to or is less than a threshold (e.g. about 10 cm). If the proximity distance is equal to or is less than the threshold, the control unit 1390 returns to operation 1501, and selects at least one biometric detection mode based on the executed biometric detection function. According to various embodiments, in the returned operation 1501, the control unit 1390 may release the selection of the proximity detection mode. The control unit 1390 may determine at least one output wavelength band of the light emitting unit 1370 in accordance with the selected at least one biometric detection mode in operation 1503.

According to various embodiments, the control unit 1390 may selectively activate at least a part of the light receiving unit 1360 based on the selected detection mode.

In operation 1509, the control unit 1390 may acquire information related with the detection mode, based on a value detected through the light receiving unit 1360. For example, in the biometric detection mode (e.g., the skin moisture detection mode, the skin melanin detection mode, the skin erythema detection mode or the like), the control unit 1390 may receive an electronic signal (or a detection value) from the light receiving unit 1360, and analyze this using various programs, to acquire information about the user (e.g., skin moisture, skin melanin, skin erythema or the like).

According to various embodiments, the control unit 1390 may acquire information related with the detection mode, and output this through the display unit (1330 of FIG. 13). For example, in the skin moisture detection mode, the control unit 1390 may acquire information about skin moisture, and display this in the information display region 16212 on the detection function list screen 1603 of FIG. 16B.

According to various embodiments, the control unit 1390 may acquire information related with a detection mode, and transmit this to another electronic device (e.g., 102, 104 or 106 of FIG. 1). For example, in the skin melanin detection mode, the control unit 1390 may acquire information about skin melanin, and transmit this data to a server supporting a health care function.

According to various embodiments, when executing the biometric detection function (e.g., the skin moisture detection function, the skin melanin detection function, the skin erythema detection function or the like), the control unit 1390 may activate the proximity detection mode in conjunction with the biometric detection function. In the proximity detection mode, when information acquired through operation 1503 to operation 1509 satisfies a reference value (e.g., when the user is in the vicinity (e.g., 10 cm or less) of the electronic device 1300), the control unit 1390 may activate the biometric detection mode (e.g., the skin moisture detection mode, the skin melanin detection mode, the skin erythema detection mode or the like), and again perform operation 1503 to operation 1509 in the biometric detection mode. According to various embodiments, the operation flow of the spectrometric sensing method of FIG. 15 may be applied when the user is using the electronic device in a phone call, and this will be described in FIG. 17.

Figure 17:
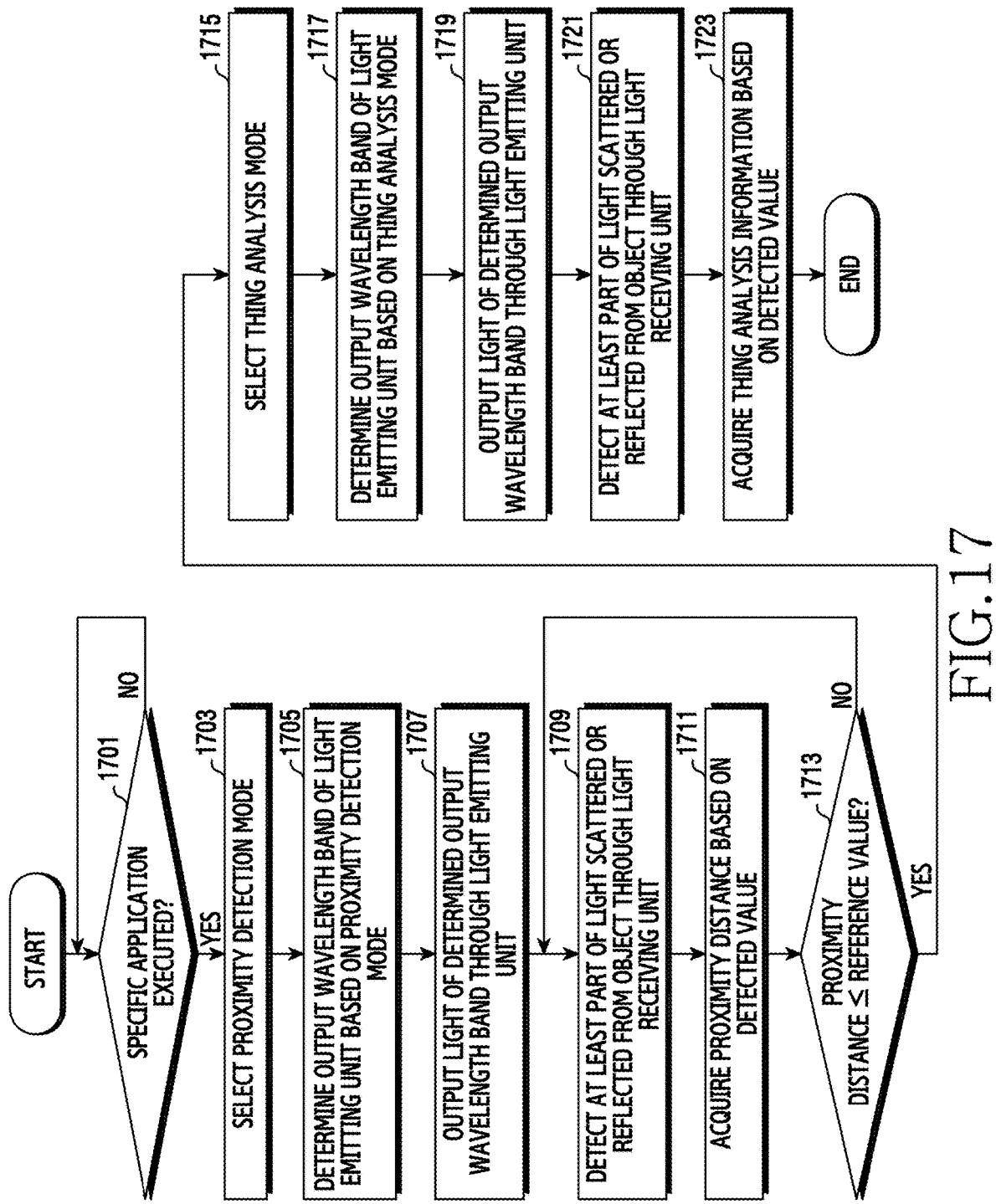
FIG. 17 is a flowchart illustrating an operation flow of a spectrometric sensing method according to an embodiment of the present disclosure.
Figure 18:
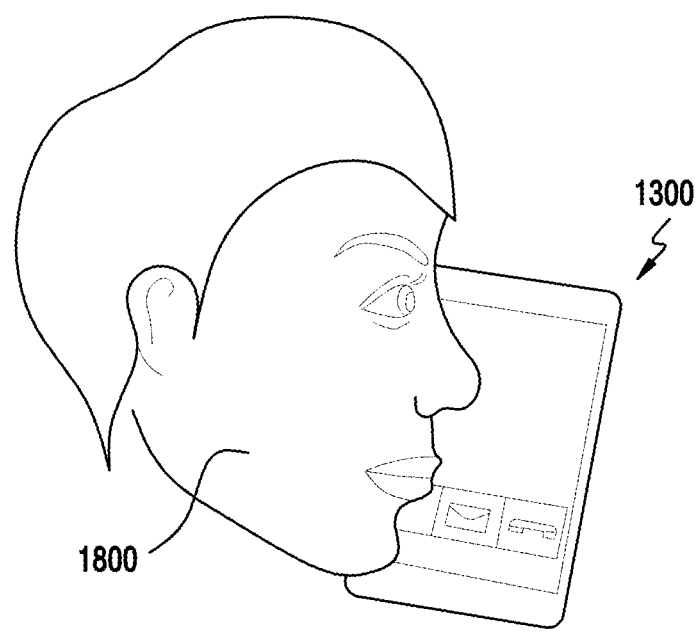
FIG. 18 is a diagram further explaining the operation flow of FIG. 17 according to an embodiment of the present disclosure.

FIG. 17 is a flowchart illustrating an operation flow of a spectrometric sensing method according to an embodiment of the present disclosure. FIG. 18 is a diagram further explaining the operation flow of FIG. 17 according to an embodiment of the present disclosure.

Referring to FIG. 17, in case where a control unit (e.g., 1390 of FIG. 13) executes a specific application in operation 1701, the control unit may perform operation 1703. The specific application may be various types of applications that require the electronic device 1300 close to the user body, such as a call application.

While the call application is executed, the electronic device 1300 may be close to the user's head. When the user makes request to call a phone number of an external device (e.g., 102 or 104 of FIG. 1), the control unit 1390 may execute an application for originating call. The electronic device 1300 may also receive a call from an external device (e.g., 102 or 104 of FIG. 1), and execute an application for incoming call.

According to an embodiment, the specific application in 1701 may also be an application for thing (e.g. the user's skin or body) analysis (below, a 'thing analysis application'). According to various embodiments, the thing analysis application may be an application for biometric detection (below, a 'biometric detection application'). For example, in case where one of the list entries 1621, 1622, 1623 and 1624 is selected by a user input on the detection function list screen 1603 of FIG. 16B, the control unit 1390 may execute the biometric detection application (or function) for the selected list entry. While the biometric detection application is executed, the electronic device 1300 may be positioned close to the user's skin for the sake of biometric detection (e.g., skin moisture detection, skin melanin detection, skin erythema detection or the like).

In operation 1703, the control unit 1390 may select the proximity detection mode based on the execution of the specific application.

In operation 1705, the control unit 1390 may determine an output wavelength band (e.g., a wavelength band including the maximum sensitivity wavelength of 950 nm) of a light emitting unit (e.g., 1370 of FIG. 13) based on the selected proximity detection mode.

In operation 1707, the control unit 1390 may control the light emitting unit 1370 to output light of the determined output wavelength band. The light emitting unit 1370 may be designed to selectively generate light of the determined wavelength band in accordance with the control of the control unit 1390.

In operation 1709, the control unit 1390 may detect, through a light receiving unit (e.g., the light receiving unit 1360 of FIG. 13), at least a part of light that is scattered or reflected from an object.

In operation 1711, the control unit 1390 may acquire the proximity distance related with the proximity detection mode, based on a value detected through the light receiving unit 1360. The acquired proximity distance may be a distance of the user in relation to the electronic device or the light receiving unit 1360. In the proximity detection mode, the control unit 1390 may analyze an electrical signal from the light receiving unit 1360 to acquire the proximity distance between an object (e.g. the user) and the spectrometric sensing apparatus (e.g., 450 of FIG. 4A or 1350 of FIG. 13). According to an embodiment, the proximity distance may be determined on the basis of a value (below, an 'ADC value") that is outputted from an ADC (not shown) electrically connected to the spectrometric sensing apparatus 1350. According to various embodiments, the ADC may be included in the spectrometric sensing apparatus 1350. When the object approaches the spectrometric sensing apparatus 1350, light (e.g., infrared rays) outputted from the light emitting unit 1370 may be reflected from the object and be transmitted to the light receiving unit 1360. The light received by the light receiving unit 1360 may be converted into a digital value by the ADC mounted in the electronic device (1300 of FIG. 13). The ADC value may be changed according to the distance between the spectrometric sensing apparatus 1350 and the object. For example, as the distance between the spectrometric sensing apparatus 1350 and the object decreases, the reflected light from the object and received by the light receiving unit 1360 may increase and accordingly, the ADC value may also increase. As the distance between the spectrometric sensing apparatus 1350 and the object increases, the reflected light from the object and received by the light receiving unit 1360 may decrease and accordingly, the ADC value may decrease.

In operation 1713, the control unit 1390 may judge if the acquired proximity distance is equal to or is less than a reference value (e.g., 10 cm). If the proximity distance is equal to or is less than the reference value, the control unit 1390 may perform operation 1715. If the proximity distance exceeds the reference value, the control unit 1390 returns to operation 1709. For example, referring to FIG. 18, while the call application is executed, if the electronic device 1300 is positioned in the vicinity (e.g., within 10 cm) of a user's head, operation 1715 may be performed.

In operation 1715, the control unit 1390 may select a thing analysis mode. For example, the thing analysis mode may include a biometric detection mode. For example, the biometric detection mode may be the skin moisture detection mode, the skin melanin detection mode, the skin erythema detection mode or the like for detecting the condition of the user's skin.

In operation 1717, the control unit 1390 may determine an output wavelength band of the light emitting unit (1370 of FIG. 13) based on the selected thing analysis mode. For example, in case where the skin moisture detection mode is selected, the control unit 1390 may determine the wavelength band including the maximum sensitivity wavelength of 880 nm and/or the wavelength band including the maximum sensitivity wavelength of 970 nm as the output wavelength band of the light emitting unit 1370. For another example, in case where the skin melanin detection mode is selected, the control unit 1390 may determine the wavelength band including the maximum sensitivity wavelength of 660 nm and/or the wavelength band including the maximum sensitivity wavelength of 880 nm as the output wavelength band of the light emitting unit 1370. For further example, in case where the skin erythema detection mode is selected, the control unit 1390 may determine the wavelength band including the maximum sensitivity wavelength of 568 nm and/or the wavelength band including the maximum sensitivity wavelength of 880 nm as the output wavelength band of the light emitting unit 1370.

In operation 1719, the control unit 1390 may control the light emitting unit 1370 to output light of the selected output wavelength band.

In operation 1721, the control unit 1390 may detect, through the light receiving unit (e.g., 1360 of FIG. 13), at least a part of light that is scattered or reflected from the thing (e.g. the user's skin). As in FIG. 18, if the electronic device 1300 is in the vicinity of the user's head 1800, the biometric detection mode may be activated. Thus, light of the appropriate wavelength band discharged from the light emitting unit (1370 of FIG. 13) may be shone on the user skin that is in the vicinity (e.g., within 10 cm) of the electronic device (1300 of FIG. 13). Then, the light may be absorbed, scattered or reflected by the user skin. The light scattered or reflected from the user skin may be received by the light receiving unit 1360. The light receiving unit 1360 may then generate an electrical signal (or a detection value) for a characteristic of the user's skin (e.g., the skin moisture, the skin melanin, the skin erythema or the like) from the scattered or reflected light, and forward the signal to the control unit 1390.

In operation 1723, the control unit 1390 may acquire thing analysis information related with the thing analysis mode, based on the electrical signal or the detection value from the light receiving unit 1360. For example, in a biometric detection mode (e.g., the skin moisture detection mode, the skin melanin detection mode, the skin erythema detection mode or the like), the control unit 1390 may receive the electronic signal (or the detection value) from the light receiving unit 1360, and analyze this using various programs, to acquire information about the living body (e.g., the skin moisture, the skin melanin, the skin erythema or the like).

Figure 19:
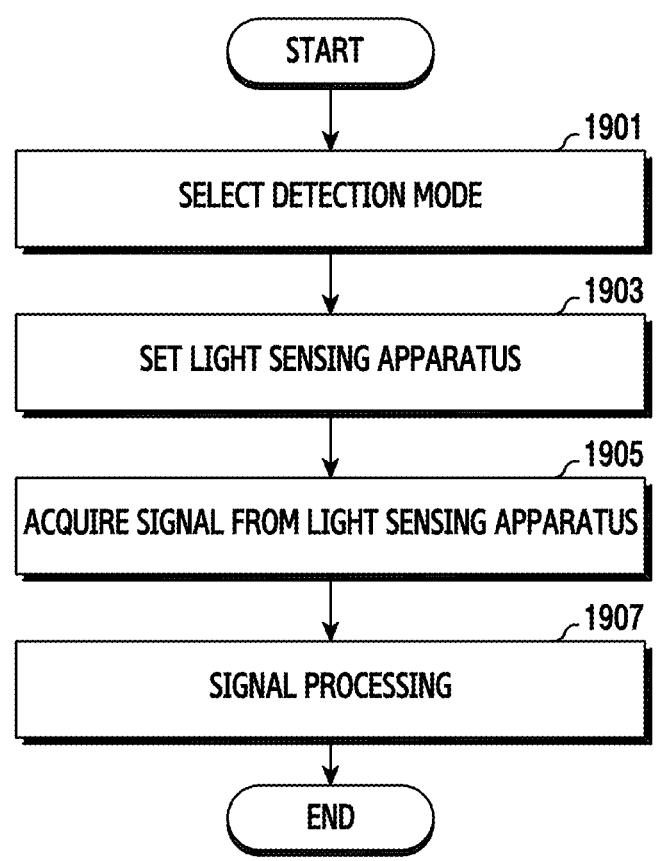
FIG. 19 is a flowchart illustrating an operation flow of a spectrometric sensing method according to an embodiment of the present disclosure.

FIG. 19 is a flowchart illustrating an operation flow of a spectrometric sensing method according to an embodiment of the present disclosure. FIGS. 20A, 20B, 20C, 21, 22, 23A, 23B, 24 and 25 are diagrams showing various methods of defining the activation or non-activation of a detection mode by user configuration setting in accordance with various embodiments of the present disclosure.

Referring to FIG. 19, in operation 1901, a control unit (e.g., 1390 of FIG. 13) may sense various types of triggers generated from an electronic device (e.g., 1300 of FIG. 13) or various types of external triggers, and select at least one detection mode.

Figure 20A:
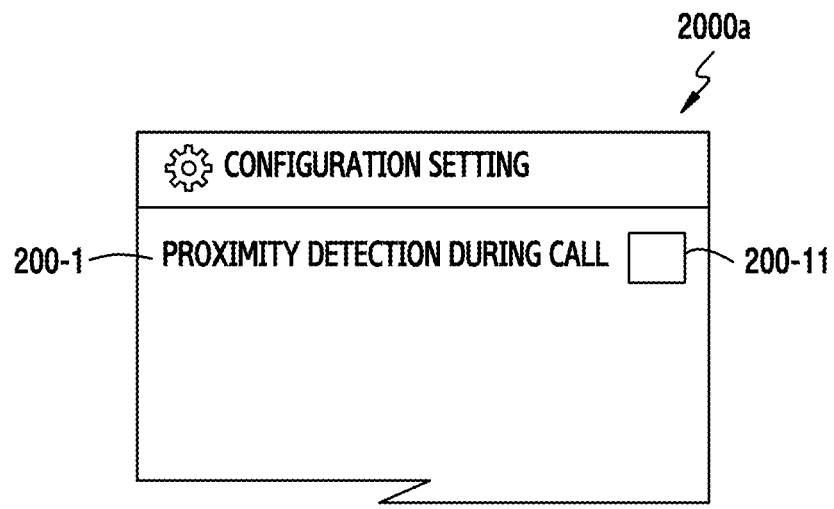
FIG. 20A, FIG. 20B, FIG. 20C, FIG. 21, FIG. 22, FIG. 23A, FIG. 23B, FIG. 24 and FIG. 25 are diagrams showing various methods of defining the activation or non-activation of a detection mode by user configuration setting in accordance with various embodiments of the present disclosure.
Figure 20B:
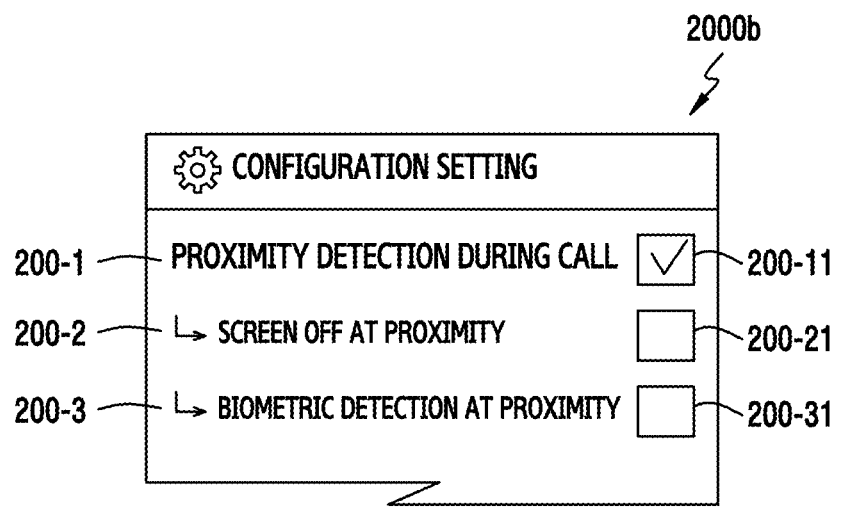
Figure 20C:
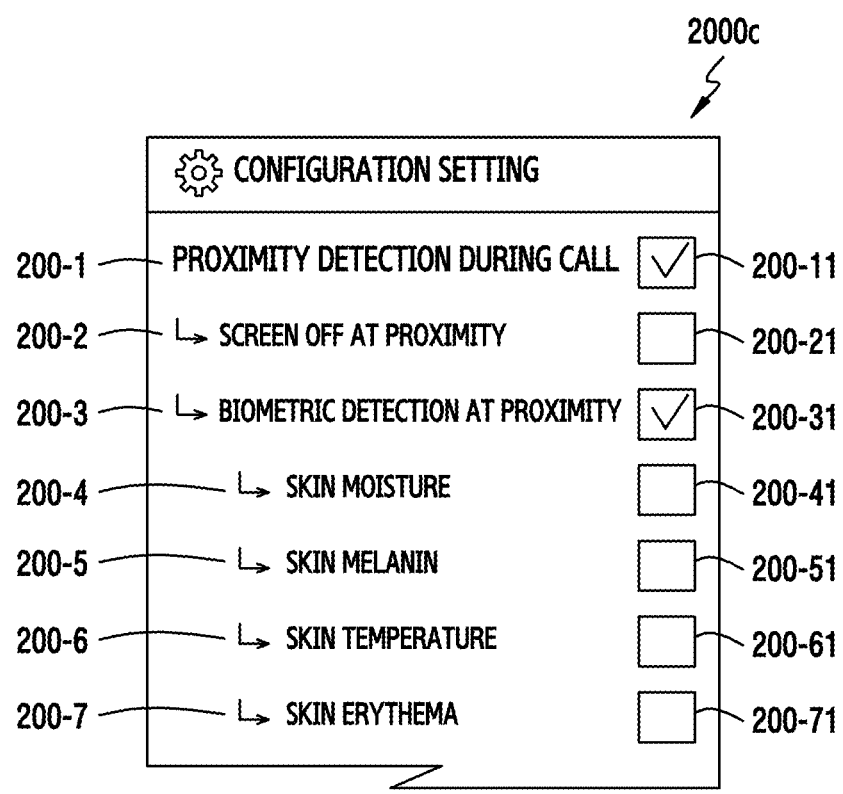

For example, FIGS. 20A, 20B and 20C illustrate screens for various configuration settings. A screen 2000a of FIG. 20A may display a first item 200-1 for setting for activating or inactivating the proximity detection mode during a call. The first item 200-1 may provide a check box 200-11. If the first item 200-1 is touched, a mark such as "V", "X" or the like is displayed in the check box 200-11, to indicate a selection of the first item 200-1. When checked, the configuration setting may be defined to activate the proximity detection mode during the call. If the first item 200-1 is again touched, the mark may disappear from the check box 200-11, to indicate the non-selection of the first item 200-1. In that case, the configuration setting may be defined so that the proximity detection mode is not activated during the call.

A screen 2000b of FIG. 20B may, if the first item 200-1 is selected, display additional selection items for activating or inactivating other modes when proximity is sensed in the proximity detection mode during a call. For example, one item 200-2 may be used for activating or inactivating the screen of the electronic device when proximity is sensed through the proximity detection mode during the call. In the alternative, another one item 200-3 may be used for activating or inactivating a biometric detection mode when proximity is sensed through the proximity detection mode during the call. The additional items 200-2 and 200-3 may also provide check boxes 200-21 and 200-31, respectively. According to an embodiment, when only the first item 200-1 is selected, the control unit 1390 may select the proximity detection mode during the call.

A screen 2000c of FIG. 20C may, if the third item 200-3 is selected, display additional items for selecting the type of a biometric detection mode. For example, the additional items may include a fourth item 200-4 for the skin moisture detection mode, a fifth item 200-5 for the skin melanin detection mode, a sixth item 200-6 for the skin temperature detection mode, a seventh item 200-7 for the skin erythema detection mode or the like. The additional items 200-4, 200-5, 200-6 and 200-7 may also provide check boxes 200-41, 200-51, 200-61 and 200-71, respectively. For example, when the first item 200-1, the third item 200-3 and the fourth item 200-4 are selected, the control unit 1390 may select the proximity detection mode during a call and, when proximity is sensed in the proximity detection mode, the control unit 1390 may select the skin moisture detection mode.

Figure 21:
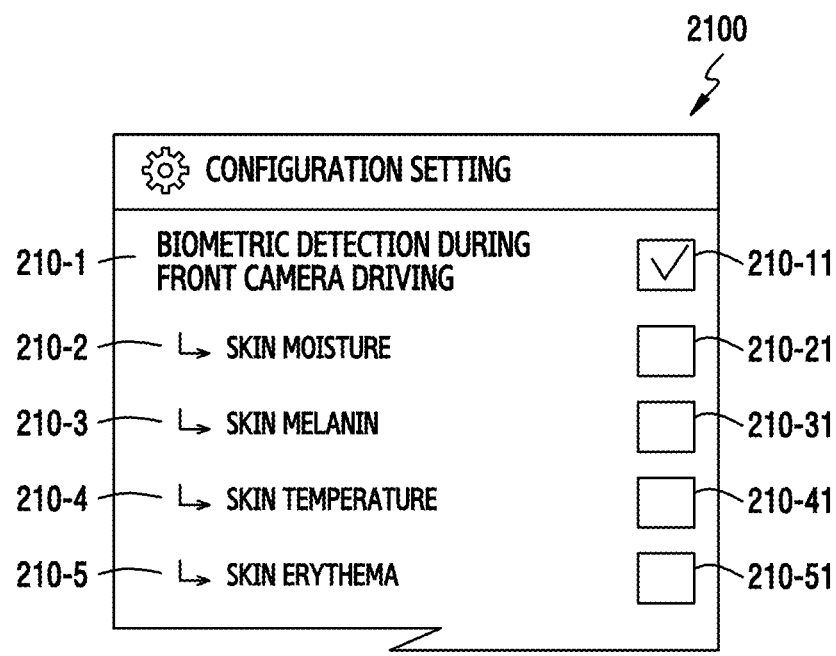

For another example, FIG. 21 illustrates a screen for configuration setting. A screen 2100 of FIG. 21 may display a first item 210-1 for activating or inactivating a biometric detection mode when the front camera is driven (i.e. activated). The first item 210-1 may provide a check box 210-11. If the first item 210-1 is selected, additional items for selecting the type of the biometric detection mode may be displayed. For example, the additional items may include a second item 210-2 for the skin moisture detection mode, a third item 210-3 for the skin melanin detection mode, a fourth item 210-4 for the skin temperature detection mode, a fifth item 210-5 for the skin erythema detection mode or the like. The additional items 210-2, 210-3, 210-4 and 210-5 may also provide check boxes 210-21, 210-31, 210-41 and 210-51, respectively. For example, when the first item 210-1, the second item 210-2 and the fourth item 210-4 are selected, the control unit 1390 may select the skin moisture detection mode and the skin temperature detection mode when the front camera is activated.

Figure 22:
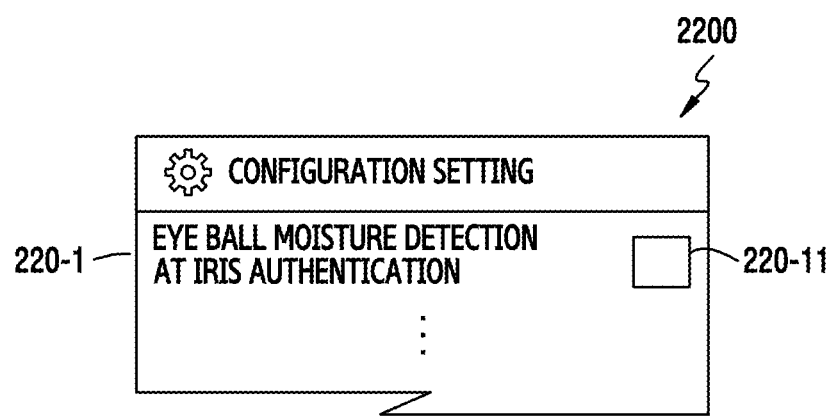

For further example, FIG. 22 illustrates a screen for configuration setting. A screen 2200 of FIG. 22 may display an item 220-1 for activating or inactivating an eyeball moisture detection mode during iris authentication. The item 220-1 may provide a check box 220-11. According to an embodiment, when the item 220-1 is selected, the control unit 1390 may select an eyeball moisture detection mode at the time of iris authentication, which may use the front camera of the electronic device. The iris authentication may be used for various security functions such as usage locking release, screen locking release, etc. of the electronic device (e.g. 1300 of FIG. 13).

Figure 23A:
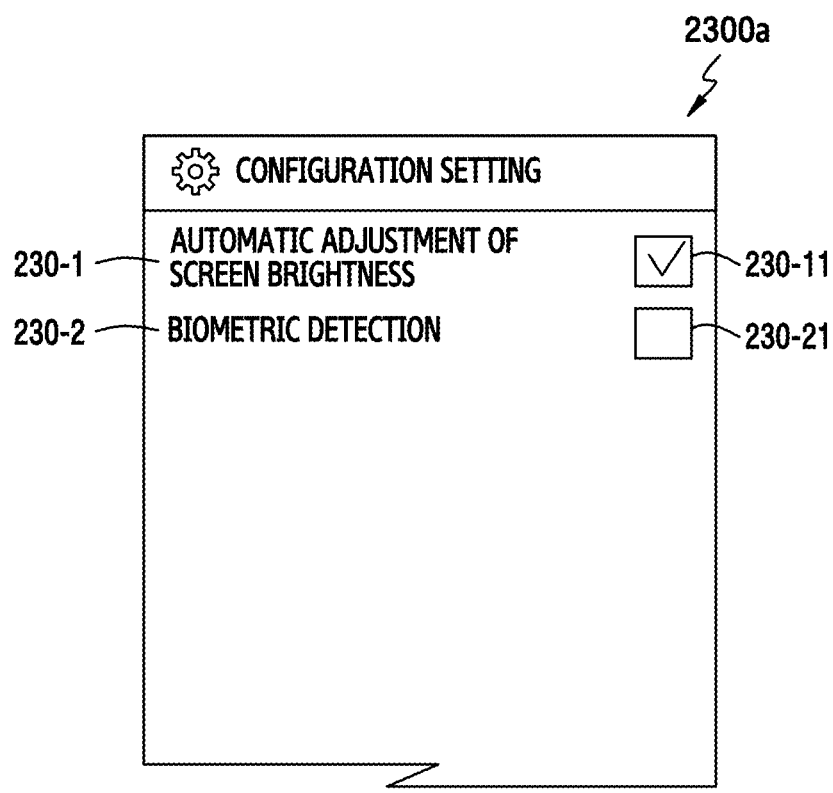
Figure 23B:
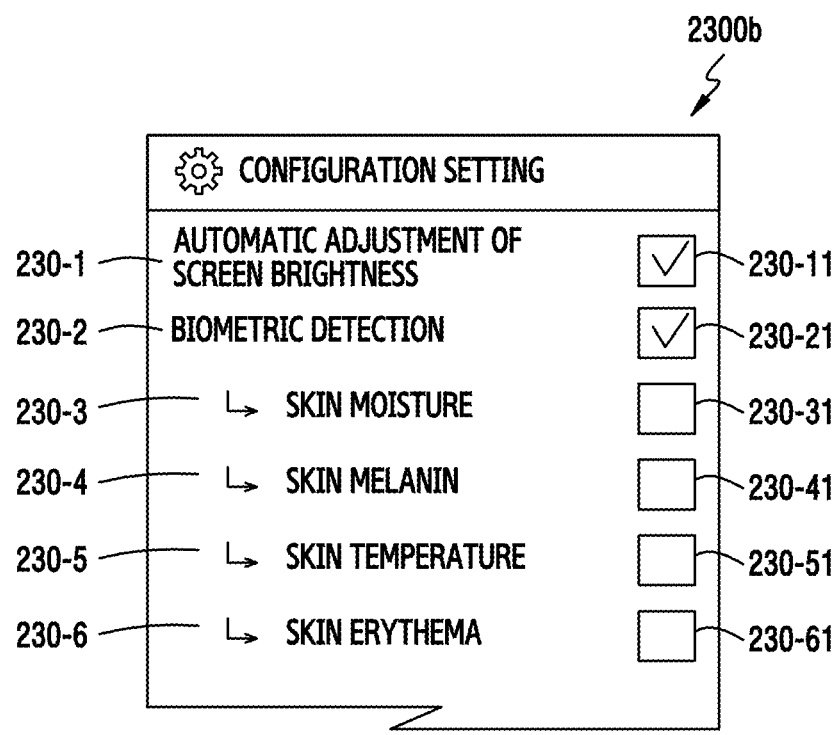

For yet another example, FIGS. 23A and 23B illustrate screens for configuration setting. A screen 2300a of FIG. 23A may display a first item 230-1 for activating or inactivating a function of automatically adjusting screen brightness using external illuminance. The screen 2300a of FIG. 23A may display a second item 230-2 for activating or inactivating a biometric detection mode. The first item 230-1 and the second item 230-2 may provide check boxes 230-11 and 230-21, respectively.

If the second item 230-2 is selected, additional items for selecting the type of the biometric detection mode may be displayed as in a screen 2300b of FIG. 23B. For example, the additional items may include a third item 230-3 for the skin moisture detection mode, a fourth item 230-4 for the skin melanin detection mode, a fifth item 230-5 for the skin temperature detection mode, a sixth item 230-6 for the skin erythema detection mode or the like. The additional items 230-3, 230-4, 230-5 and 230-6 may also provide check boxes 230-31, 230-41, 230-51 and 230-61, respectively. For example, when the first item 230-1, the third item 230-3 and the fourth item 230-4 are selected, the control unit 1390 may select the illuminance detection mode, the skin moisture detection mode and the skin melanin detection mode.

Figure 24:
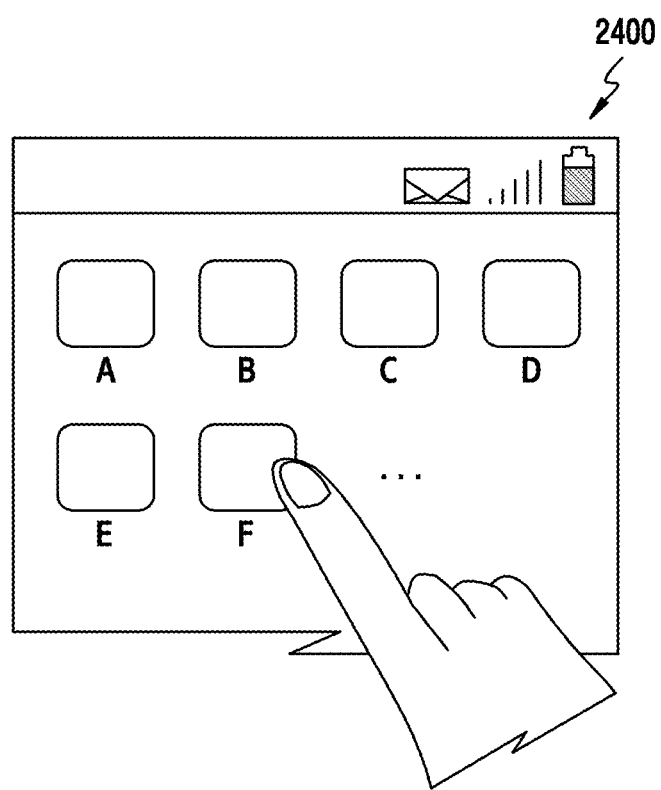

For still another example, FIG. 24 illustrates a screen 2400 of displaying icons (e.g., 'A', 'B', 'C', 'D', 'E', 'F', etc.) that represent a plurality of applications. When one of the many icons is selected by a user's touch input, the control unit 1390 may select at least one detection mode that corresponds to the application represented by the selected icon.

For still another example, if a predefined input signal is generated using at least one of a plurality of buttons (e.g., buttons of the electronic device 400 of FIGS. 4A and 4B) installed in the electronic device 1300, the control unit 1390 may select a detection mode corresponding to the input signal among a plurality of detection modes. For example, if the button is pressed a threshold time or longer, or is pressed continuously at a predefined number of times (e.g., two times), at least one detection mode according to this may be selected.

For still another example, if a predefined touch input or hovering input is generated through a screen of the electronic device 1300, the control unit 1390 may select a detection mode corresponding to the input signal among a plurality of detection modes. For example, if a gesture of tapping a screen continuously at a predefined number of times (e.g., three times) is performed, at least one detection mode according to this may be selected.

Figure 25:
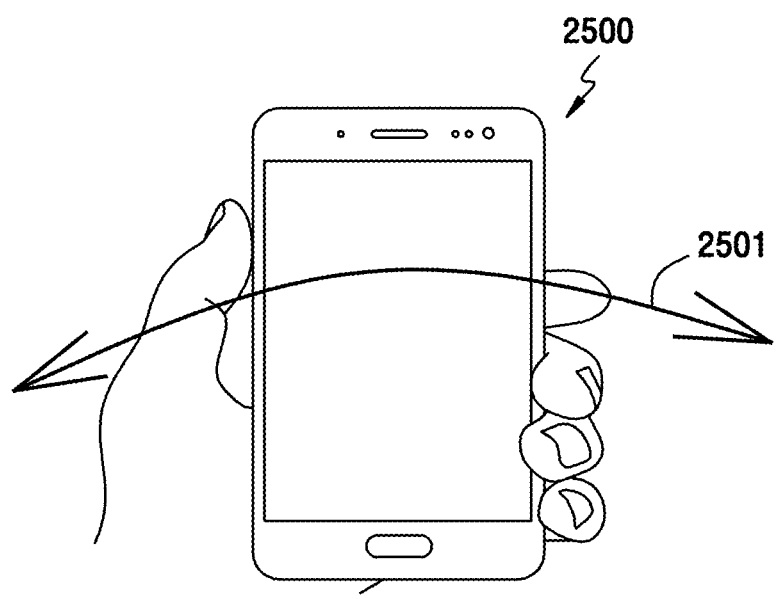

For still another example, referring to FIG. 25, if an input of moving the electronic device 2500 (e.g., the electronic device 400 of FIGS. 4A and 4B) in a predefined pattern takes place, the control unit 1390 may select a detection mode corresponding to the input among a plurality of detection modes. For example, if shaking the electronic device 2500 right and left (2501), at least one detection mode according to this may be selected.

In operation 1903, the control unit 1390 may set the spectrometric sensing apparatus 1350 in accordance with the selected at least one detection mode. According to an embodiment, the control unit 1390 may select at least one light detector for the selected detection mode from a light receiving unit (1360 of FIG. 13), and activate the selected light detector. The light emitting unit (e.g., 1370 of FIG. 13) may be designed to selectively generate light of a specific wavelength band in accordance with the control of the control unit 1390 as well. According to various embodiments, the light emitting unit 1370 may include a plurality of light emitters. And, the plurality of light emitters may generate light of mutually different wavelength bands. The control unit 1390 may select at least one light emitter for the selected detection mode from the light emitting unit 1370, and activate the selected light detector.

<Table 1>, <Table 2>, <Table 3> and <Table 4> below represent setting of the spectrometric sensing apparatus 1350 according to various embodiments.

Referring to <Table 1> below, the light emitting unit 1370 of the spectrometric sensing apparatus 1350 may include light emitters that are used in mutually different detection modes respectively. The light receiving unit 1360 of the spectrometric sensing apparatus 1350 may include light detectors that are used in mutually different detection modes respectively.

TABLE 1

| | Spectrometric sensing apparatus 1350 | |
|---|---|---|
| Detection modes | Light emitting unit 1370 | Light receiving unit 1360 |
| First detection mode | Light emitter for first wavelength band | First light detector |
| Second detection mode | Light emitter for second wavelength band | Second light detector |
| ... | ... | ... |
| Nth detection mode | Light emitter for Nth wavelength band | Nth light detector |

Referring to <Table 2> below, the light emitting unit 1370 of the spectrometric sensing apparatus 1350 may include light emitters that are used in mutually different detection modes respectively. The light receiving unit 1360 of the spectrometric sensing apparatus 1350 may include a light detector that is used in one or more detection modes (e.g., a multi detection mode).

TABLE 2

| | Spectrometric sensing apparatus 1350 | |
|---|---|---|
| Detection modes | Light emitting unit 1370 | Light receiving unit 1360 |
| First detection mode | Light emitter for first wavelength band | First light detector |
| ... | ... | |
| Nth detection mode | Light emitter for Nth wavelength band | |
| N + 1th detection mode | Light emitter for N + 1th wavelength band | Second light detector |
| ... | ... | |
| Mth detection mode | Light emitter for Mth wavelength band | |
| | ... | |

Referring to <Table 3> below, the light emitting unit 1370 of the spectrometric sensing apparatus 1350 may include a light emitter that may generate light of a multi wavelength band or a broad wavelength band. The light receiving unit 1360 of the spectrometric sensing apparatus 1350 may include light detectors that are used in mutually different detection modes respectively.

TABLE 3

| | Spectrometric sensing apparatus 1350 | |
|---|---|---|
| Detection modes | Light emitting unit 1370 | Light receiving unit 1360 |
| First detection mode | Light emitter for multi wavelength band or broad wavelength band | First light detector |
| ... | | ... |
| Nth detection mode | | Nth light detector |

Referring to <Table 4> below, the light emitting unit 1370 of the spectrometric sensing apparatus 1350 may include a light emitter that may generate light of a multi wavelength band or a broad wavelength band. The light receiving unit 1360 of the spectrometric sensing apparatus 1350 may include a light detector that is used in one or more detection modes (e.g., a multi detection mode).

TABLE 4

| | Spectrometric sensing apparatus 1350 | |
|---|---|---|
| Detection modes | Light emitting unit 1370 | Light receiving unit 1360 |
| First detection mode | Light emitter for multi wavelength band or broad wavelength band | First light detector |
| ... | | |
| Nth detection mode | | |
| N + 1th detection mode | | Second light detector |
| ... | | |

In operation 1905, the control unit 1390 may acquire a signal that is outputted through the spectrometric sensing apparatus 1350 in the selected detection mode. For example, in the proximity or gesture detection mode, the spectrometric sensing apparatus 1350 may detect a light signal of the proximity or gesture detecting wavelength bands, and generate and forward an electrical signal to the control unit 1390. Or, in the illuminance detection mode, the spectrometric sensing apparatus 1350 may detect a light signal of the illuminance detecting wavelength band, and generate and forward an electrical signal to the control unit 1390. Or, in the biometric detection mode, the spectrometric sensing apparatus 1350 may detect a light signal of the biometric detecting wavelength band, and generate and forward an electrical signal to the control unit 1390.

In operation 1907, the control unit 1390 may process the signal acquired from the spectrometric sensing apparatus 1350. For example, when a first detection mode is selected, the spectrometric sensing apparatus 1350 may detect a light signal of a first wavelength band for the first detection mode, and generate and transmit a first electrical signal to the control unit 1390. While in the first detection mode, the control unit 1390 may detect information from the first electrical signal, and process the detected information. The operation of processing the detected information may include the operation of displaying the detected information through a display unit (e.g., 1330 of FIG. 13), the operation of transmitting the detected information to an external device (e.g., a server supporting a health care function, etc.), etc. In the alternative, when the first detection mode is selected, the spectrometric sensing apparatus 1350 may further detect an light signal of a second wavelength band that is different from the first wavelength band for the first detection mode, and generate and forward a second electrical signal to the control unit 1390. In the first detection mode, the control unit 1390 may process the second electrical signal as invalid.

According to an embodiment of the present disclosure, a method for operating an electronic device may include selecting a detection mode based on the execution of an application and/or a user input, determining an output wavelength band of a light emitting unit based on the selected detection mode, outputting light of the determined output wavelength band via the light emitting unit, detecting, via a light receiving unit, at least a part of the outputted light scattered or reflected from an object, and acquiring information related with the selected detection mode based on the light detected by the light receiving unit.

According to an embodiment of the present disclosure, outputting the light of the determined output wavelength band via the light emitting unit may further include controlling the light emitting unit to selectively output the light of the determined output wavelength band.

According to an embodiment of the present disclosure, outputting the light of the determined output wavelength band via the light emitting unit may further include selectively activating at least one light source capable of outputting the light of the determined output wavelength band among a plurality of light sources comprised in the light emitting unit.

According to an embodiment of the present disclosure, detecting the at least part of the scattered or reflected light via the light receiving unit may further include selectively activating at least a part of the light receiving unit, based on the selected detection mode.

According to an embodiment of the present disclosure, the application may comprise a call related application or a biometric detection related application.

According to an embodiment of the present disclosure, the selected detection mode may be a proximity detection mode, and information related with the proximity detection mode may include a proximity distance between the object and the electronic device.

According to an embodiment of the present disclosure, the method may further include, if the proximity distance is equal to or is less than a reference value, selecting a mode for biometric detection based on the execution of the application, a user configuration setting, and/or a user input.

According to an embodiment of the present disclosure, the selected detection mode may be a mode for biometric detection, and information related with the biometric detection mode may include information about a user skin state.

According to an embodiment of the present disclosure, the method of operating the electronic device may further comprise displaying the acquired information through a screen of the electronic device.

According to an embodiment of the present disclosure, the method of operating the electronic device may further comprise transmitting the acquired information to another electronic device.

According to various embodiments of the present disclosure, a method for operating an electronic device may include selecting a proximity detection mode at execution of a specific application, determining an output wavelength band of a light emitting unit based on the proximity detection mode, outputting light of the determined output wavelength band through the light emitting unit, detecting at least a part of the outputted light scattered or reflected from the user body through a light receiving unit based on the proximity detection mode, and acquiring a proximity distance between the user body and the electronic device from the light detected by the light receiving unit based on the proximity detection mode. If the proximity distance is equal to or is less than a reference value, the method may further include selecting a biometric detection mode, determining an output wavelength band of the light emitting unit based on the biometric detection mode, outputting light of the determined output wavelength band through the light emitting unit, detecting at least a part of the outputted light scattered or reflected from the user body using the light receiving unit, and acquiring biometric information about the user body from the light detected by the light receiving unit.

A spectrometric sensing apparatus in an electronic device and a method thereof according to various embodiments of the present disclosure may, for example, provide a spectrometric sensing function even without expanding the size of the electronic device (i.e. without adding a separate spectrometric sensing sensor). This is accomplished by modifying a partial region of a proximity sensing optical sensor unit or a partial region of an illuminance sensing optical sensor unit to include one or more other optical sensor units for detecting (e.g., spectrometric sensing) light signals of various wavelength bands.

A spectrometric sensing apparatus in an electronic device and a method thereof according to various embodiments of the present disclosure may improve a user's convenience and utilization of services that require spectrometric sensing, by performing the spectrometric sensing through one surface of the electronic device that also includes the display. A spectrometric sensing apparatus in an electronic device and a method thereof according to various embodiments of the present disclosure may also provide various types of services such as biometric recognition services for measuring states of the user's skin.

Meanwhile, the aforementioned embodiments of the present disclosure may be composed as a program that is executable in a computer, and may be implemented in a generic digital computer that operates the program using a computer-readable recording media. Also, a structure of data used in the aforementioned embodiment of the present disclosure may be recorded in the computer-readable recording media through various means. The computer-readable recording medium includes a storage medium such as a magnetic storage medium (for example, a Read Only Memory (ROM), a floppy disc, a hard disc, etc.) and an optical reading medium (for example, a Compact Disc-ROM (CD-ROM), a Digital Versatile Disc (DVD), etc.).

The above-described embodiments of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein.

Hitherto, the present disclosure has been described aiming at preferred embodiments of the present disclosure. A person having ordinary skill in the art to which the present disclosure pertains would be able to understand that the present disclosure may be implemented in a modified form within a scope not departing from the intrinsic characteristic of the present disclosure. Therefore, disclosed embodiments should be taken into consideration in a descriptive aspect, not in a restrictive aspect. The scope of the present disclosure is presented in the appended claims, not in the aforementioned description, and all differences within a scope equivalent thereto will have to be construed as being included in the present disclosure.

What is claimed is:

1. An electronic device comprising:
   a housing;
   a display within the housing, and exposed through a surface of the housing;
   a light emitting unit and a light receiving unit within the housing; and
   a processor electrically coupled with the display, the light emitting unit and the light receiving unit,
   wherein the light emitting unit comprises at least one light source for outputting light of at least one wavelength band,
   the light receiving unit comprises at least one region for receiving the light of the at least one wavelength band, and
   the processor is configured to:
      control at least one function of the light emitting unit and/or the light receiving unit based on at least one mode, and
      control the light emitting unit to selectively output light of a wavelength band that corresponds to the at least one mode.

2. The electronic device of claim 1, wherein the light emitting unit comprises a plurality of light sources, each light source outputs light of mutually different wavelength bands, and the processor is further configured to selectively activate at least one of the plurality of light sources based on the at least one mode.

3. The electronic device of claim 1, wherein the processor is further configured to selectively activate at least one region of the light receiving unit based on the at least one mode.

4. The electronic device of claim 1, wherein the at least one mode comprises:
   a mode for detecting proximity of an object using light of a wavelength band including a wavelength of 950 nanometers (nm),
   a mode for detecting a user skin moisture using light of wavelength bands including a wavelength of 880 nm or 970 nm,
   a mode for detecting a user skin melanin using light of wavelength bands including a wavelength of 660 nm or 880 nm, or
   a mode for detecting a user skin erythema using light of wavelength bands including a wavelength of 568 nm or 880 nm.

5. The electronic device of claim 1, wherein the processor is further configured to:
   acquire information related with the at least one mode based on the light received by the light receiving unit, and
   display the acquired information using the display.

6. The electronic device of claim 1, further comprising a communication module, and wherein the processor is further configured to:
   acquire information related with the at least one mode based on the light received by the light receiving unit, and
   transmit the acquired information to another electronic device through the communication module.

7. The electronic device of claim 1, wherein the light receiving unit comprises:
   one or more first regions for receiving light of a proximity detecting wavelength band,
   one or more second regions for receiving light of an illuminance detecting wavelength band, and/or
   one or more third regions for receiving light of a biometric detecting wavelength band.

8. The electronic device of claim 1, wherein in a first mode:
   the light receiving unit detects light of a first wavelength band for the first mode and light of a second wavelength band for a second mode different from the first mode,
   the light receiving unit coverts the light of the first wavelength band into a first electrical signal and the light of the second wavelength band into a second electrical signal,
   the light receiving unit transmits the first electrical signal and the second electrical signal to the processor, and
   the processor is further configured to process the second electrical signal as invalid.

9. The electronic device of claim 1, wherein the light receiving unit comprises:
   at least one diode; and
   a filter disposed on an upper surface of the at least one diode, and adapted to filter light of at least one specific wavelength band.

10. The electronic device of claim 1, wherein the surface of the housing comprises:
   one light transmission region for the light emitting unit and the light receiving unit, or
   a first light transmission region for the light emitting unit and a second light transmission region isolated from the first light transmission region for the light receiving unit.

* * * * *